(12) United States Patent
Vanlandschoot et al.

(10) Patent No.: US 11,098,113 B2
(45) Date of Patent: Aug. 24, 2021

(54) IMMUNOGLOBULIN SINGLE VARIABLE DOMAINS DIRECTED AGAINST MACROPHAGE MIGRATION INHIBITORY FACTOR

(71) Applicants: VIB VZW, Ghent (BE); Vrije Universiteit Brussel, Brussels (BE)

(72) Inventors: Peter Vanlandschoot, Bellem (BE); Ines Cabrito, Oporto (PT); Benoît Stijlemans, Kampenhout (BE); Amanda Sparkes, Mechelen (BE); Jo Van Ginderachter, Ninove (BE); Patrick De Baetselier, Berchem (BE)

(73) Assignees: VIB VZW, Ghent (BE); Vrije Universiteit Brussel, Brussels (BE)

( * ) Notice: Subject to any disclaimer, the term of this patent is extended or adjusted under 35 U.S.C. 154(b) by 87 days.

(21) Appl. No.: 16/333,730

(22) PCT Filed: Sep. 15, 2017

(86) PCT No.: PCT/EP2017/073302
§ 371 (c)(1),
(2) Date: Mar. 15, 2019

(87) PCT Pub. No.: WO2018/050833
PCT Pub. Date: Mar. 22, 2018

(65) Prior Publication Data
US 2019/0309056 A1 Oct. 10, 2019

Related U.S. Application Data

(60) Provisional application No. 62/394,927, filed on Sep. 15, 2016.

(51) Int. Cl.
*C07K 16/24* (2006.01)
*C07K 16/18* (2006.01)
*A61K 39/00* (2006.01)

(52) U.S. Cl.
CPC .............. *C07K 16/24* (2013.01); *C07K 16/18* (2013.01); *A61K 2039/505* (2013.01); *C07K 2317/22* (2013.01); *C07K 2317/31* (2013.01); *C07K 2317/33* (2013.01); *C07K 2317/34* (2013.01); *C07K 2317/35* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01); *C07K 2319/00* (2013.01); *C07K 2319/31* (2013.01); *Y02A 50/30* (2018.01)

(58) Field of Classification Search
None
See application file for complete search history.

(56) References Cited

U.S. PATENT DOCUMENTS

| 6,030,615 | A | 2/2000 | Bucala et al. | |
|---|---|---|---|---|
| 2014/0120115 | A1* | 5/2014 | Zierow | C07K 16/24 424/173.1 |

FOREIGN PATENT DOCUMENTS

| WO | 0164749 A2 | 9/2001 |
|---|---|---|
| WO | 2007134538 A1 | 11/2007 |
| WO | 2009086920 A1 | 7/2009 |
| WO | WO 2009/086920 A1 * | 7/2009 |
| WO | 2011073180 A1 | 6/2011 |
| WO | 2013010955 A1 | 1/2013 |
| WO | 2014037419 A1 | 3/2014 |
| WO | WO 2014/037419 A1 * | 3/2014 |

OTHER PUBLICATIONS

Paul, Fundamental Immunology, Raven Press, New York, 1993, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6): 1075-1084).*
Chen et al. (J Mol Biol. 1999; 293:865-881).*
Sparkes et al., 2018, FASEB J 32:3411-3422.*
Desmyter et al: "Camelid nanobodies: killing two birds with one stone", Current Opinion in Structural Biology, vol. 32, Jun. 1, 2015 (Jun. 1, 2015), pp. 1-8, XP055417841, GB ISSN: 0959-440X, DOI: 10.1016/j.sbi.2015.01.001
Desmyter et al: "Three Camelid VHH Domains in Complex with Porcine Pancreatic [alpha]-Amylase : Inhibition and Versatility of Binding Topology", Journal of Biological Chemistry, vol. 277, No. 26, Apr. 17, 2002 (Apr. 17, 2002), pp. 23645-23650, XP055417338, ISSN: 0021-9258, DOI: 10.1074/jbc.M202327200.
Dumoulin M et al: "Single-domain antibody fragments with high conformational stability", Protein Science, Wiley, US, vol. 11, No. 3, Mar. 1, 2002 (Mar. 1, 2002 ), pp. 500-515, XP002296277, ISSN: 0961-8368, DOI: 10.1110/PS.34602.
Kerschbaumer et al: "Neutralization of Macrophage Migration Inhibitory Factor (MIF) by Fully Human Antibodies Correlates with Their Specificity for the -Sheet Structure of MIF", Journal of Biological Chemistry, vol. 287, No. 10, Jan. 11, 2012 (Jan. 11, 2012 ), pp. 7446-7455, XP055050382, ISSN: 0021-9258, DOI: 10.1074/jbc.M111.329664.
PCT International Search Report and Written Opinion, Application No. PCT/EP2017/073302, dated Jan. 31, 2018, 32 pgs.

(Continued)

*Primary Examiner* — Elizabeth C. Kemmerer
(74) *Attorney, Agent, or Firm* — Patent Law Works, LLP

(57) ABSTRACT

The present invention relates to immunoglobulin single variable domains that bind MIF and more in particular to polypeptides that comprise or essentially consist of one or more such immunoglobulin single variable domains; to nucleic acids encoding such polypeptides; to methods for preparing such polypeptides; to compositions and in particular to pharmaceutical compositions that comprise such polypeptides, for prophylactic, therapeutic or diagnostic purposes.

11 Claims, 8 Drawing Sheets

Figure 2:
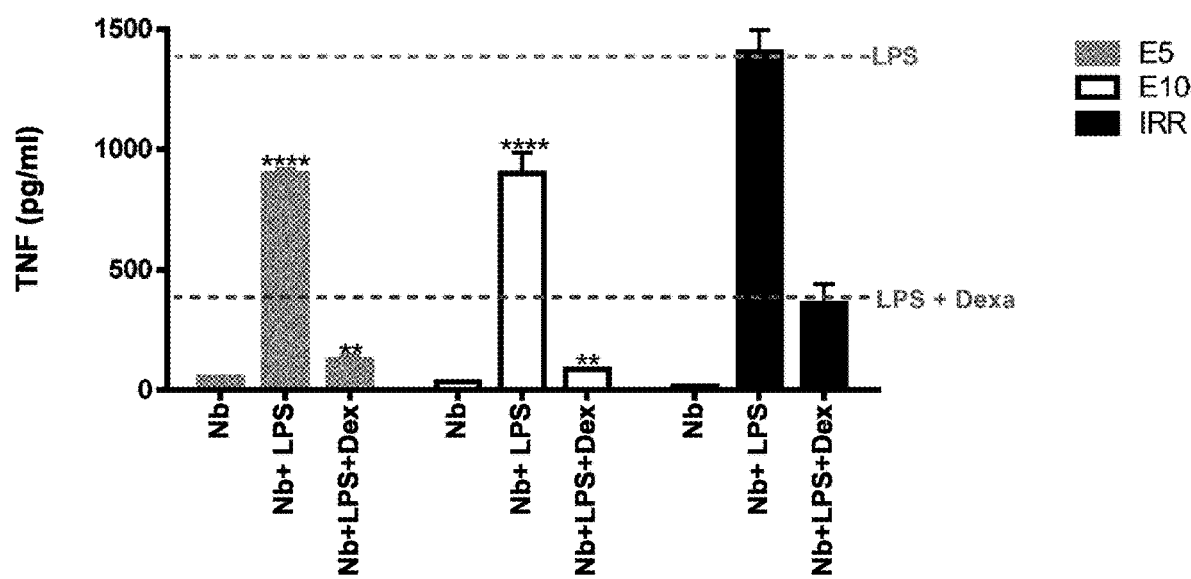

Specification includes a Sequence Listing.

(56) References Cited

OTHER PUBLICATIONS

Tarasuk et al: "Human single-chain variable fragment antibody inhibits macrophage migration inhibitory factor tautomerase activity", International Journal of Molecular Medicine, vol. 33, No. 3, Mar. 1, 2014 (Mar. 1, 2014), pp. 515-522, XP055416421, GR ISSN: 1107-3756, DOI: 10.3892/ijmm.2014.1622.

Wang et al: "Nanobody-derived nanobiotechnology tool kits for diverse biomedical and biotechnology applications", International Journal of Nanomedicine, vol. Volume 11, Jul. 1, 2016 (Jul. 1, 2016), pp. 3287-3303, XP055417843, Auckland, NZ ISSN: 1176-9114, DOI: 10.2147/IJN.S107194.

Zhang et al: "Characterization, epitope identification and mechanisms of the anti-septic capacity of monoclonal antibodies against macrophage migration inhibitory factor", International Immunopharmacology, Elsevier, Amsterdam, NL, vol. 11, No. 9, Apr. 25, 2011 (Apr. 25, 2011), pp. 1333-1340, XP028265421, ISSN:1567-5769, DOI: 10.1016/J.INTIMP.2011.04.017 [retrieved on May 3, 2011].

* cited by examiner

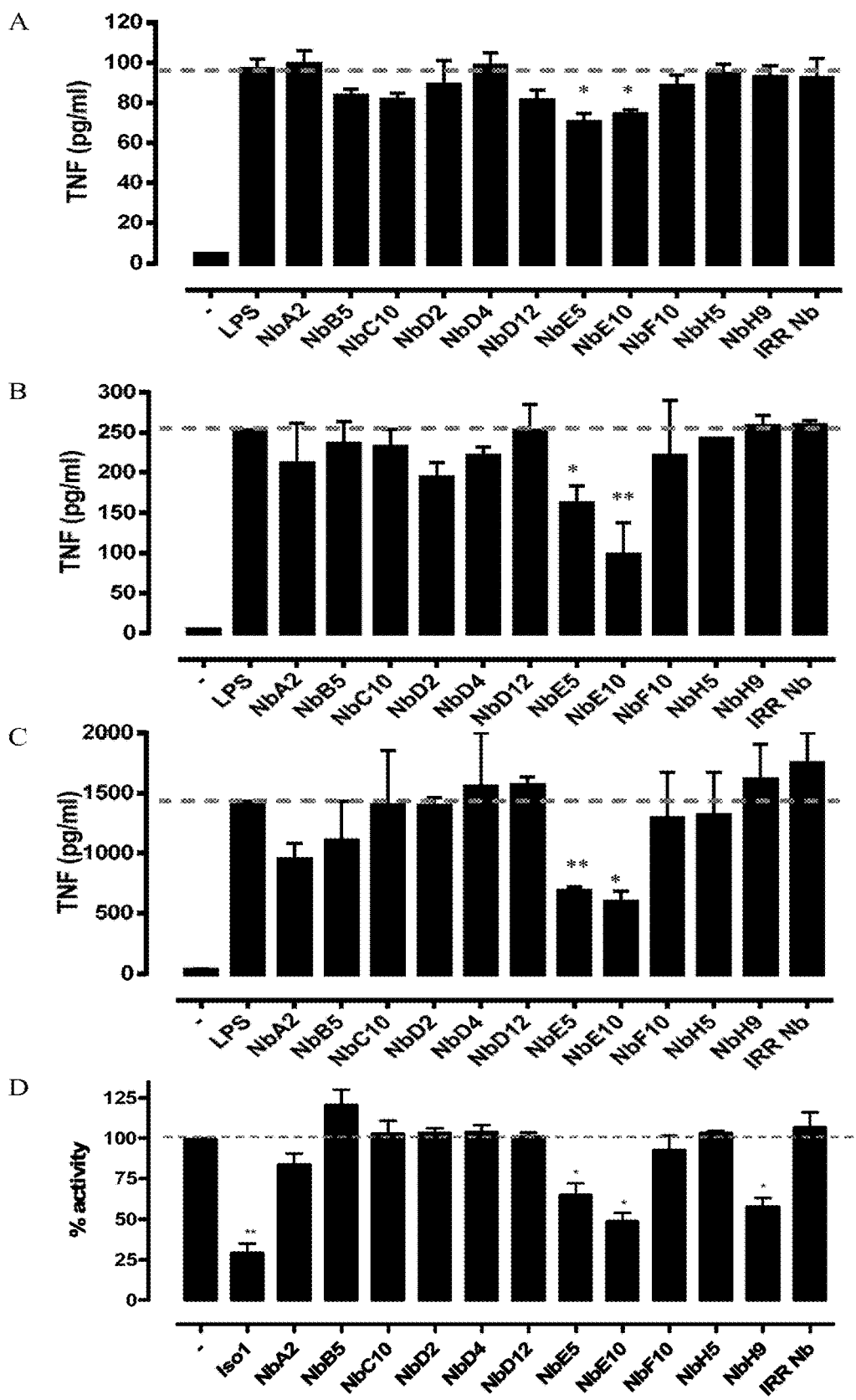
Figure 1: Inhibition of MIF's biological activities by anti-MIF ISVDs

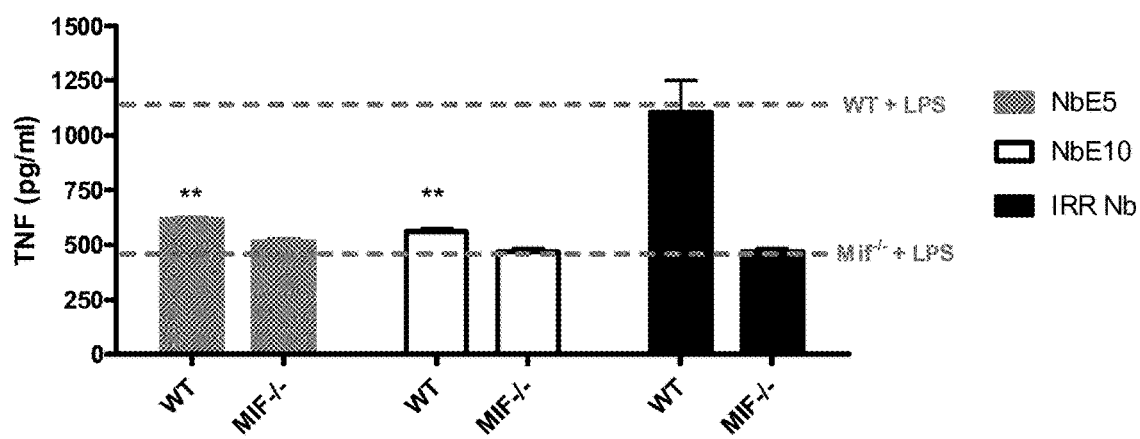
Figure 1E: Anti-MIF ISVD E5 (NbE5) and ISVD E10 (NbE10) can inhibit TNF secretion of LPS-stimulated macrophages from WT mice to levels seen in MIF-deficient mice.

| Peptide | A2 | B5 | C10 | D2 | D4 | D12 | E5 | E10 | F10 | H5 | H9 |
|---|---|---|---|---|---|---|---|---|---|---|---|
| I | ++ | - | - | - | - | - | - | - | - | - | - |
| II | ++ | +/- | - | + | + | +/- | + | +/- | - | - | - |
| III | - | +/- | - | +/- | +/- | +/- | + | + | +/- | +/- | + |
| IV | - | - | - | - | - | - | + | + | - | - | + |
| V | - | - | +/- | - | - | - | - | - | +/- | - | - |
| VI | - | - | +/- | - | - | - | - | - | - | - | - |

Figure 7

IMMUNOGLOBULIN SINGLE VARIABLE DOMAINS DIRECTED AGAINST MACROPHAGE MIGRATION INHIBITORY FACTOR

RELATED APPLICATIONS

This application is a national stage filing under 35 U.S.C. § 371 of International Patent Application Serial No. PCT/EP2017/073302, filed Sep. 15, 2017, which claims the benefit under 35 U.S.C. § 119(e) of U.S. Provisional Application Ser. No. 62/394,927, filed Sep. 15, 2016, the contents of each of which are incorporated herein by reference in its entirety.

FIELD OF THE INVENTION

The present invention relates to MIF binders, such as immunoglobulin single variable domains that bind Macrophage Migration Inhibitory Factor and more in particular to polypeptides, that comprise or essentially consist of one or more such immunoglobulin single variable domains (also referred to herein as "ISVD(s) of the invention", and "polypeptides of the invention", respectively).

The invention also relates to nucleic acids encoding such polypeptides (also referred to herein as "nucleic acid(s) of the invention"); to methods for preparing such polypeptides; to host cells expressing or capable of expressing such polypeptides; to compositions, and in particular to pharmaceutical compositions, that comprise such polypeptides, nucleic acids and/or host cells; and to uses of polypeptides, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

BACKGROUND

Persistence, deregulation or overproduction of pro-inflammatory mediators can culminate into a wide variety of acute and chronic inflammatory diseases. The treatment is usually non-curative and aimed at suppressing inflammatory end-organ damage.

Macrophage Migration Inhibitory Factor (MIF) was identified as a key pro-inflammatory cytokine, based on elevated serum concentration in animals and patients with severe sepsis/endotoxic shock. Indeed, MIF serum concentration correlates with disease severity (1-2). Moreover, MIF was found to override the protective effects of glucocorticoids (3). Hence, MIF was implied in initiating and prolonging inflammatory responses in a wide variety of disease processes including autoimmune diseases, metabolic disorders, systemic infections as well as sepsis. Although MIF's precise function is still not known, despite being identified already in 1966, strategies to inhibit MIF's deleterious effects might be of therapeutic potential.

MIF is a 12.3 kDa small cytokine with chemokine-like properties. It is ubiquitously expressed in various tissues in mammals and its structure is highly conserved with about 90% sequence homology between mouse and human species (4). MIF consists of 115 amino acids, but the N-terminal methionine residue is post-translationally removed after ribosomal synthesis in essentially all cells and organisms. Crystallographic studies showed that MIF is as a homotrimer consisting of three monomers each having two antiparallel α-helices and a four-stranded β-sheet. Two additional, short β-strands can be detected in each monomer which interact with the β-sheet of the adjacent subunits (5). However, different studies revealed MIF to be able to exist as monomer, dimer, trimer, or even higher-order oligomers, which is potentially concentration-dependent. Although the biologically relevant "active" oligomerization state of MIF is still elusive (5-7), it is likely that the MIF homotrimer is not the only biologically active form (8). MIF mediates most of its biological activities through its primary transmembrane surface receptor, CD74 (the class II invariant chain that exhibits a highly structured trimerization domain) present on MHC-II expressing cells. MIF also mediates chemotactic effects by binding to the chemokine receptors CXCR2, CXCR4 and CXCR7. While the interaction sites between MIF and CXCR2 are well documented (9) and the interaction site between MIF and CXCR4 has recently been discovered (59), the interaction site between MIF and CXCR7 still needs to be identified.

MIF is a ubiquitously expressed, pleiotropic, pro-inflammatory cytokine that controls metabolic and inflammatory processes at the level of innate and adaptive immunity (4). In mammals, MIF exhibits a thiol-protein oxidoreductase activity, which is attributed to a thioredoxin-like CXXC motif (10), and a keto-enol tautomerase activity (i.e. catalyzing the tautomerization of D-dopachrome, hydroxylenylpyruvate and phenylpyruvate) for the function of which the N-terminal conserved proline (Pro1) is thought to be important (4, 11, 13). Yet, it is unclear whether MIF's enzymatic activity has any biological relevance in mammals, rather it is most likely vestigial with the enzymatic active site playing a structural role in protein-protein interactions. Indeed, it was shown that the region encompassing the tautomerization site also makes critical contacts with MIF's receptor CD74, whereby modification of Pro1 or its replacement with glycine abolishes tautomerase activity and impairs receptor binding (14).

Although the mechanism by which MIF asserts its biological activity has yet to be fully understood, MIF is considered an attractive target to alleviate metabolic, systemic, autoimmune, and inflammation-associated disorders (15-17). Current research efforts have focused on small molecule approaches that target MIF's unique tautomerase active site or on anti-MIF antibodies that neutralize MIF's activity (60).

Anti-MIF antibodies reduced inflammation in experimental animal models of glomerulonephritis, arthritis and allograft rejection, confirming a role for MIF in the regulation of inflammatory processes (cf. 4, 18-19). Calandra et al. (20) describes that a mouse anti-MIF antibody would protect TNF knockout mice from lethal peritonitis induced by cecal ligation and puncture (CLP).

Tarasuk et al. (21) describes a human single chain variable antibody fragment which would inhibit MIF's tautomerase activity. Tarasuk et al. (21) is silent on in vivo effects, if any.

Kerschbaumer et al. (22) describes the generation of a diverse panel of fully human mAbs against MIF. Neutralization of MIF was only achieved by mAbs against two specific epitopic regions, i.e. amino acids 50-68 and amino acids 86-102. However, most mAbs against these regions were not able to exert protective effects.

Recent disappointments in the application of biologically based therapies, such as in anti-TNFα or anti-CD20 antibodies to SLE, the high cost of production, parenteral administration of Ab-based therapies and the loss of efficacy that may arise from anti-idiotype responses revived the interest in the small-molecule approach.

One of the oldest and best characterized small molecule MIF inhibitors is ISO-1 ((S,R)-3-(4-hydroxyphenyl)-4,5-dihydro-5-isoxazole acetic acid methyl ester), which inhibits MIF's tautomerase activity in vitro, and which was also shown to be protective in vivo (23). However, in spite of promising results with ISO-1, the route and dose of administration and in vivo toxicity suggest that ISO-1 is not suitable for human use (24). Moreover, its selectivity for MIF remains to be established.

Other small molecule MIF inhibitors belong to the fluorosubstituted phenylpyruvic acid class. N-acetyl-p-benzoquinone, an acetaminophen metabolite, its synthetic derivatives and the acetylenic compound 2-oxo-4-phenyl-3-butynoate were potent in vitro inhibitors of the phenyl pyruvate tautomerase activity of MIF. Some oxygen heterocycles, such as coumarines and chromenes, have also drawn attention as MIF inhibitors. The α,β-unsaturated carbonyl compounds constitute another large novel class of potential MIF inhibitors.

Although, the small molecule inhibitors such as ISO-1 as well as monoclonal antibodies (mAbs) against MIF or DNA-based MIF vaccination strategies have been shown to attenuate inflammation in animal models of sepsis (20, 22, 61, 62), these approaches require either repetitive or high dosing due to the rapid clearance of the molecules or the repeated injection of very large amounts of humanized Abs, which are prone to generating undesirable local and systemic side-reactions (43).

In addition, most of these small molecules are designed to inhibit the tautomerase activity of MIF. However, it seems questionable that the tautomerase activity is important for mediating all of MIFs biological effects. Indeed, none of the small molecule MIF inhibitors is clinically validated.

There is a need for compounds that modulate the activity of MIF. More particularly, there is a need for MIF inhibitors, especially there is a need for more efficient MIF inhibitors.

SUMMARY OF THE INVENTION

The present invention provides MIF inhibitors with particular, unexpected functional properties.

Based on extensive screening, characterization and combinatory strategies, the present inventors surprisingly observed that polypeptides comprising immunoglobulin single variable domains binding MIF showed improved properties for modulating MIF activity (compared to the MIF binders described in the prior art).

More specifically, the present inventors surprisingly observed that the polypeptide based MIF inhibitors of the present invention had in vivo anti-MIF activity, even lacking an Fc-region, which is in contrast to the prior art antibodies. It is well established that conventional antibodies exert their effects via binding and an Fc-mediated activation of immune cells and induction of cytokines via FcγR interaction on these cells. This results in effector functions, such as Fc-mediated antibody-dependent cellular cytotoxicity (ADCC) and complement-dependent cytotoxicity (CDC). When targeting inflammatory diseases in humans, however, the absence of an antibody-mediated activation of immune cells and induction of cytokines via FcγR interaction on these cells can be advantageous.

Also, in contrast to the prior art (22), the present inventors also identified anti-MIF ISVDs that inhibited both, MIF's tautomerase activity as well as MIF's in vivo activity. Further in contrast to the prior art (22), anti-MIF ISVDs were identified that bind to MIF-derived linear binding regions (e.g. amino acids 35-68) and also reduced MIF's tautomerase activity.

The ISVDs of the invention furthermore demonstrated a significant improved protective effect in vitro when conjugated to Alb-binders. This effect was wholly unexpected. Moreover, this improved effect was also passed on in acute in vivo sepsis models, in which extension of the compound's half-life appears less relevant.

This is the first report of a bioengineered, small biologic MIF inhibitor that prevents lethal endotoxemia when administered as a single injection. Hence, ISVDs with their structural and pharmacologic advantages over currently available inhibitors may be effective tools to interfere with MIF-mediated pro-inflammatory effects and improve prognosis of sepsis patients as an adjunctive therapeutic strategy. Additionally, they could also find applications in a wide array of other MIF-mediated inflammatory diseases.

Accordingly, the present invention relates to an immunoglobulin single variable domain (ISVD) that specifically binds to Macrophage Migration Inhibitory Factor (MIF), preferably to human MIF (SEQ ID NO: 89) or polymorphic variants or isoforms thereof and/or mouse MIF (SEQ ID NO: 91) or polymorphic variants or isoforms thereof and/or rhesus MIF (SEQ ID NO: 90) or polymorphic variants or isoforms thereof. Said ISVD preferably consists essentially of a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation.

The present invention also relates to an ISVD as described herein, wherein said ISVD has an on rate constant (Kon) for binding to said MIF selected from the group consisting of at least about $10^2$ $M^{-1}$ $s^{-1}$, at least about $10^3$ $M^{-1}$ $s^{-1}$, at least about $10^4$ $M^{-1}$ $s^{-1}$, at least about $10^5$ $M^{-1}$ $s^{-1}$, at least about $10^6$ $M^{-1}$ $s^{-1}$, $10^7$ $M^{-1}$ $s^{-1}$, at least about $10^8$ $M^{-1}$ $s^{-1}$, at least about $10^9$ $M^{-1}$ $s^{-1}$, and at least about $10^{10}$ $M^{-1}$ $s^{-1}$, preferably as measured by surface plasmon resonance, and/or wherein said ISVD has an off rate constant (Koff) for binding to said MIF selected from the group consisting of at most about $10^{-3}$ $s^{-1}$, at most about $10^{-4}$ $s^{-1}$, at most about $10^{-5}$ $s^{-1}$, at most about $10^{-6}$ $s^{-1}$, at most about $10^{-7}$ $s^{-1}$, at most about $10^{-8}$ $s^{-1}$, at most about $10^{-9}$ $s^{-1}$, and at most about $10^{-10}$ $s^{-1}$, also preferably as measured by surface plasmon resonance, and/or wherein said ISVD binds to said MIF with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such as less than 10 pM, again, wherein the KD is preferably determined by SPR, such as, for instance as determined by Proteon.

The present invention also relates to an ISVD as described herein, wherein said ISVD essentially consists of 4 framework regions (FR1 to FR4, respectively) and 3 complementarity determining regions (CDR1 to CDR3, respectively), in which: (i) CDR1 is chosen from the group consisting of: (a) SEQ ID NOs: 23-33; and (b) amino acid sequences that have 4, 3, 2, or 1 amino acid(s) difference with the amino acid sequence of SEQ ID NO: 23 or with any of SEQ ID NOs: 23-33; and/or (ii) CDR2 is chosen from the group consisting of: (c) SEQ ID NOs: 45-55; and (d) amino acid sequences that have 4, 3, 2, or 1 amino acid(s) difference with the amino acid sequence of SEQ ID NO: 45 or with any of SEQ ID NOs: 45-55; and/or (iii) CDR3 is chosen from the group consisting of: (e) SEQ ID NOs: 67-77; and (f) amino acid sequences that have 3, 2, or 1 amino acid(s) difference with the amino acid sequence of SEQ ID NO: 67 or with any of SEQ ID NOs: 67-77.

The present invention also relates to an ISVD as described herein, wherein said ISVD essentially consists of 4 framework regions (FR1 to FR4, respectively) and 3 complementarity determining regions (CDR1 to CDR3, respectively), in which CDR1 is chosen from the group consisting of (a) SEQ ID NO: 23; and (b) amino acid sequences that have 1, 2, 3 or 4 amino acid difference(s) with SEQ ID NO: 23, wherein at position 2 the R has been changed into F; at position 3 the T has been changed into S; at position 4 the L has been changed into I, S, F or A; at position 5 the S has been changed into R; at position 6 the N has been changed into S, T or I; at position 7 the S has been changed into Y, Q, H or V; and/or at position 8 the I has been changed into F, A, V or T; and/or in which CDR2 is chosen from the group consisting of (a) SEQ ID NO: 45; and (b) amino acid sequences that have 1, 2, 3 or 4 amino acid difference(s) with SEQ ID NO: 45, wherein at position 2 the N has been changed into G or S; at position 3 the W has been changed into F or N; at position 4 the S has been changed into G, N or K; at position 5 the G has been changed into Y or F; at position 6 the T has been changed into S or G; at position 7 the S has been changed into M, T, V or L; and/or at position 8 the R has been changed into P or T; and/or in which CDR3 is chosen from the group consisting of (a) SEQ ID NO: 67; and (b) amino acid sequences that have 1, 2 or 3 amino acid difference(s) with SEQ ID NO: 67, wherein at position 1 the A has been changed into S or V; at position 2 the A has been changed into K; at position 3 the R has been changed into G; at position 4 the S has been changed into G, I or P or is absent; at position 5 the S has been changed into A, L, G, D or V or is absent; at position 6 the T has been changed into G, N or R or is absent; a G is introduced between position 6 and 7 of SEQ ID NO: 67; at position 7 the M has been changed into Q or G or is absent; at position 8 the S has been changed into L, Q T, I or R or is absent; at position 9 the A has been changed into T, E, D, P, V or N or is absent; at position 10 the T has been changed into N, Y or F or is absent; at position 11 the D has been changed into T; and/or at position 12 the Y has been changed into F or S.

The present invention also relates to an ISVD as described herein, wherein said ISVD is chosen from the group of ISVs, wherein: CDR1 is chosen from the group consisting of SEQ ID NOs: 23, 24, 25, 26, 27, 28, 29, 30, 31, 32 and 33; CDR2 is chosen from the group consisting of SEQ ID NOs: 45, 46, 47, 48, 49, 50, 51, 52, 53, 54, and 55; and CDR3 is chosen from the group consisting of SEQ ID NOs: 67, 68, 69, 70, 71, 72, 73, 74, 75, 76 and 77, preferably wherein CDR1 is SEQ ID NO: 23, CDR2 is SEQ ID NO: 45, and CDR3 is SEQ ID NO: 67; CDR1 is SEQ ID NO: 24, CDR2 is SEQ ID NO: 46, and CDR3 is SEQ ID NO: 68; CDR1 is SEQ ID NO: 25, CDR2 is SEQ ID NO: 47, and CDR3 is SEQ ID NO: 69; CDR1 is SEQ ID NO: 26, CDR2 is SEQ ID NO: 48, and CDR3 is SEQ ID NO: 70; CDR1 is SEQ ID NO: 27, CDR2 is SEQ ID NO: 49, and CDR3 is SEQ ID NO: 71; CDR1 is SEQ ID NO: 28, CDR2 is SEQ ID NO: 50, and CDR3 is SEQ ID NO: 72; CDR1 is SEQ ID NO: 29, CDR2 is SEQ ID NO: 51, and CDR3 is SEQ ID NO: 73; CDR1 is SEQ ID NO: 30, CDR2 is SEQ ID NO: 52, and CDR3 is SEQ ID NO: 74; CDR1 is SEQ ID NO: 31, CDR2 is SEQ ID NO: 53, and CDR3 is SEQ ID NO: 75; CDR1 is SEQ ID NO: 32, CDR2 is SEQ ID NO: 54, and CDR3 is SEQ ID NO: 76; and CDR1 is SEQ ID NO: 33, CDR2 is SEQ ID NO: 55, and CDR3 is SEQ ID NO: 77; preferably wherein said ISVD has been chosen from the group consisting of SEQ ID NOs 1-11.

The present invention also relates to an ISVD as described herein, wherein said ISVD essentially consists of 4 framework regions (FR1 to FR4, respectively) and 3 complementarity determining regions (CDR1 to CDR3, respectively), in which: (i) CDR1 is chosen from the group consisting of: (a) SEQ ID NOs: 28-31; and (b) amino acid sequences that have 2 or 1 amino acid(s) difference with the amino acid sequence of SEQ ID NO: 28; and/or (ii) CDR2 is chosen from the group consisting of: (c) SEQ ID NOs: 50-53; and (d) amino acid sequences that have 2 or 1 amino acid(s) difference with the amino acid sequence of SEQ ID NO: 50; and/or (iii) CDR3 is chosen from the group consisting of: (e) SEQ ID NOs: 72-75; and (f) amino acid sequences that have 2 or 1 amino acid(s) difference with the amino acid sequence of SEQ ID NO: 72; preferably in which CDR1 is chosen from the group consisting of (a) SEQ ID NO: 28; and (b) amino acid sequences that have 1, or 2 amino acid difference(s) with SEQ ID NO: 28, wherein at position 7 the Q has been changed into H; and/or at position 8 the V has been changed into T; and/or in which CDR3 is chosen from the group consisting of (a) SEQ ID NO: 72; and (b) amino acid sequences that have 1 or 2 amino acid difference(s) with SEQ ID NO: 72, wherein at position 7 the I has been changed into T; and/or at position 8 the T has been changed into P.

The present invention also relates to an ISVD as described herein, wherein said ISVD essentially consists of 4 framework regions (FR1 to FR4, respectively) and 3 complementarity determining regions (CDR1 to CDR3, respectively), in which: (i) CDR1 is chosen from the group consisting of: (a) SEQ ID NOs: 25-26; and (b) amino acid sequences that have 2, or 1 amino acid(s) difference with the amino acid sequence of SEQ ID NO: 25; and/or (ii) CDR2 is chosen from the group consisting of: (c) SEQ ID NOs: 47-48; and (d) amino acid sequences that have 2 or 1 amino acid(s) difference with the amino acid sequence of SEQ ID NO: 47; and/or (iii) CDR3 is chosen from the group consisting of: (e) SEQ ID NOs: 69-70; and (f) amino acid sequences that have 4, 3, 2, or 1 amino acid(s) difference with the amino acid sequence of SEQ ID NO: 69; preferably, in which CDR1 is chosen from the group consisting of (a) SEQ ID NO: 25; and (b) amino acid sequences that have 1, or 2 amino acid difference(s) with SEQ ID NO: 25, wherein at position 4 the F has been changed into S; and/or at position 6 the S has been changed into T; and/or in which CDR3 is chosen from the group consisting of (a) SEQ ID NO: 69; and (b) amino acid sequences that have 1, 2, 3 or 4 amino acid difference(s) with SEQ ID NO: 69, wherein at position 1 the V has been changed into S; at position 6 the T has been changed into N; at position 8 the D has been changed into E; and/or at position 11 the Y has been changed into F.

The present invention also relates to an ISVD as described herein, wherein said ISVD essentially consists of 4 framework regions (FR1 to FR4, respectively) and 3 complementarity determining regions (CDR1 to CDR3, respectively), in which: CDR1 comprises SEQ ID NO: 23, CDR2 comprises SEQ ID NO: 45, and CDR3 comprises SEQ ID NO: 67, preferably wherein CDR1 is SEQ ID NO: 23; and/or CDR2 is SEQ ID NO: 45; and/or CDR3 is SEQ ID NO: 67.

The present invention also relates to an ISVD as described herein, wherein said ISVD cross-blocks the binding of a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to MIF.

The present invention also relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to MIF, and which competes for binding to MIF with the ISVD as described herein.

The present invention also relates to an ISVD as described herein, wherein said ISVD inhibits an inflammatory immune response by more than about 10%, such as 20%, 30%, or 40% or even more than 50%, such as more than 60%, such as 70%, 80%, or even more than 90% such as 100%; and/or wherein said ISVD inhibits tautomerase activity by more than about 10%, such as 20%, 30%, or 40% or even more than 50%, such as more than 60%, such as 70%, 80%, or even more than 90% such as 100%. and/or wherein said ISVD inhibits TNF-induction, preferably as assessed by an LPS stimulation assay by more than about 10%, such as 20%, 30%, or 40% or even more than 50%, such as more than 60%, such as 70%, 80%, or even more than 90% such as 100%; and/or wherein said ISVD inhibits TNF-secretion by more than about 10%, such as 20%, 30%, or 40% or even more than 50%, such as more than 60%, such as 70%, 80%, or even more than 90% such as 100%; and/or wherein said ISVD inhibits a MIF activity by more than about 10%, such as 20%, 30%, or 40% or even more than 50%, such as more than 60%, such as 70%, 80%, or even more than 90% such as 100%. and/or wherein said ISVD inhibits inflammation by more than about 10%, such as 20%, 30%, or 40% or even more than 50%, such as more than 60%, such as 70%, 80%, or even more than 90% such as 100%.

The present invention also relates to a polypeptide comprising at least one ISVD as described herein, preferably at least two ISVDs as described herein, wherein said at least two ISVDs can be the same or different. Said at least two ISVDs are independently chosen from the group consisting of SEQ ID NOs: 1-11, preferably wherein each of said at least two ISVDs are represented by SEQ ID NO: 1.

The present invention also relates to a polypeptide as described herein, comprising at least one further ISVD, such as a polypeptide comprising SEQ ID NO: 121. Preferably, the polypeptide is chosen from the group consisting of SEQ ID NOs: 119-122.

The present invention also relates to a polypeptide as described herein, wherein said polypeptide further comprises a serum protein binding moiety or serum protein; preferably wherein said serum protein binding moiety binds serum albumin. Even more preferably wherein said serum protein binding moiety is an ISVD binding serum albumin, which preferably consists essentially of 4 framework regions (FR1 to FR4, respectively) and 3 complementarity determining regions (CDR1 to CDR3 respectively), in which CDR1 is SFGMS (SEQ ID NO: 116), CDR2 is SISGSGSDTLYADSVKG (SEQ ID NO: 117) and CDR3 is GGSLSR (SEQ ID NO: 118). Preferably, said ISVD binding serum albumin comprises Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92 or Alb223 [SEQ ID NOs: 103-115 and 123-124]. The present invention also relates to a polypeptide as described herein, wherein said serum protein binding moiety is a non-antibody based polypeptide. The present invention also relates to a polypeptide as described herein, further comprising PEG.

The present invention also relates to a polypeptide as described herein, wherein said ISVDs are directly linked to each other or are linked via a linker, for instance wherein a first ISVD and/or a second ISVD and/or possibly a third ISVD and/or possibly said ISVD binding serum albumin are linked via a linker. Preferably, the linker is chosen from the group consisting of linkers of 5GS, 7GS, 9GS, 10GS, 15GS, 18GS, 20GS, 25GS, 30GS, 35GS, poly-A, [SEQ ID NOs: 92-102], 8GS, 40GS, G1 hinge, 9GS-G1 hinge, llama upper long hinge region, and G3 hinge [SEQ ID NOs: 125-130].

The present invention also relates to a compound or construct that comprises or essentially consists of an ISVD as described herein and/or a polypeptide as described herein, and which further comprises one or more other groups, residues, moieties or binding units, optionally linked via one or more peptidic linkers; preferably in which said one or more other groups, residues, moieties or binding units is chosen from the group consisting of a polyethylene glycol molecule, serum proteins or fragments thereof, binding units that can bind to serum proteins, an Fc portion, and small proteins or peptides that can bind to serum proteins.

The present invention also relates to a nucleic acid encoding an ISVD as described herein, a polypeptide as described herein, or a compound or construct as described herein.

The present invention also relates to an expression vector comprising a nucleic acid as described herein.

The present invention also relates to a host or host cell comprising a nucleic acid as described herein, or an expression vector as described herein.

The present invention also relates to a method for producing an ISVD as described herein or a polypeptide as described herein, said method at least comprising the steps of: a) expressing, in a suitable host cell or host organism or in another suitable expression system, a nucleic acid sequence as described herein; optionally followed by: b) isolating and/or purifying the ISVD as described herein, or the polypeptide as described herein.

The present invention also relates to a composition comprising at least one ISVD as described herein, a polypeptide as described herein, a compound or construct as described herein, or a nucleic acid as described herein. Preferably, said composition is a pharmaceutical composition. Even more preferably, said composition further comprises at least one pharmaceutically acceptable carrier, diluent or excipient and/or adjuvant, and optionally comprises one or more further pharmaceutically active polypeptides and/or compounds.

The present invention also relates to a composition as described herein, an ISVD as described herein, a polypeptide as described herein, and/or a compound or construct as described herein for use as a medicament, preferably for use in preventing or treating sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections.

The present invention also relates to a method for preventing or treating sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections, wherein said method comprises administering, to a subject in need thereof, a pharmaceutically active amount of at least a composition, an ISVD, a polypeptide, or a compound or construct as described herein to a person in need thereof.

The present invention also relates to the use of an immunoglobulin, a polypeptide, a compound or construct, or a composition as described herein, in the preparation of a pharmaceutical composition for treating or preventing sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections.

The present invention also relates to a kit comprising an ISVD, a polypeptide, a nucleic acid, a vector, a host cell, a composition and/or a pharmaceutical composition as as described herein, preferably with instructions for use.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety.

FIGURE LEGENDS

FIG. 1: Inhibition of MIF's biological activities by anti-MIF ISVDs (indicated as "Nb"). Anti-MIF ISVDs were found to reduce TNF secretion from LPS (10 ng/well) stimulated THP-1 monocytic cells (A), human PBMC's (B) and RAW 2647.7 macrophages (C). Briefly, cells were treated with 500 nM of each anti-MIF ISVD and an irrelevant ISVD was used as a negative control. After 18 hours of incubation, cell culture supernatants were collected for the determination of TNF concentration. Data is shown as the mean±SEM. Statistical analysis was performed by comparing TNF levels of ISVD-treated LPS-stimulated cells to levels of untreated LPS-stimulated cells. The dotted line represents TNF levels (cut-off level) of mice stimulated with LPS alone. D) Inhibition of MIF D-dopachrome tautomerase activity by anti-MIF ISVDs. ISO-1 was used as positive control. The activity was determined by the semi-continuous reduction in signal (tautomerization) measured at $OD_{450nm}$ in the presence and absence of anti-MIF ISVDs. The % activity was expressed in relationship to the tautomerase activity of rmMIF alone. The dotted line represents 100% activity (i.e. when only MIF was used). Data is shown as the mean±SEM and representative of 3 independent experiments (n=2) (*: p<0.05, **: p<0.01). (E) Anti-MIF ISVD E5 and ISVD E10 can inhibit TNF secretion of LPS-stimulated macrophages from WT mice to levels of MIF-deficient mice. The potential of the anti-MIF ISVDs to reduce TNF production was compared between peritoneal exudate cells (PECs/PEMs) from C57BL/6 wild-type (WT) and MIF-deficient (Mif$^{-/-}$) mice following LPS (10 ng/well) stimulation. Briefly, cells were treated with 500 nM of each anti-MIF ISVDs and an irrelevant ISVD was used as a negative control. After 18 hours of incubation, cell culture supernatants were collected for determination of the TNF concentration. Data is shown as the mean±SEM. Statistical analysis was performed by comparing TNF levels of ISVD-treated LPS-stimulated cells to levels of untreated LPS-stimulated cells. The upper and lower red line represents TNF levels (cut-off level) of PECS from WT and Mif$^{-/-}$ mice, respectively, stimulated with LPS alone.

FIG. 2 shows that anti-MIF ISVDs (indicated as "Nb") can override MIF's anti-immunosuppressive effects of glucocorticoids. RAW264.7 cells were treated with 10 ng of LPS, with or without 500 nM of anti-MIF ISVD and/or 10 nM dexamethasone ("Dexa" or "Dex"). After 18 h of incubation, cell culture supernatants were collected for determination of TNF concentration. Data is shown as the mean±SEM. Statistical analysis was performed by comparing TNF levels of anti-MIF ISVD-treated cells to when LPS was added in the presence of dexamethasone and an irrelevant ISVD (IRR) or of TNF as compared to when LPS was added in the absence of anti-MIF ISVDs. The bottom dotted line represents TNF levels (cut-off-level) of cells stimulated with LPS in the presence of dexamethasone and an irrelevant ISVD. The top dotted line represents TNF levels (cut-off level) of cells stimulated with LPS in the absence of Dexa. Data is representative of 3 independent experiments±SEM, (n=2) and *: p<0.05, : p<0.01 or **: p<0.0001.

Figure 3:
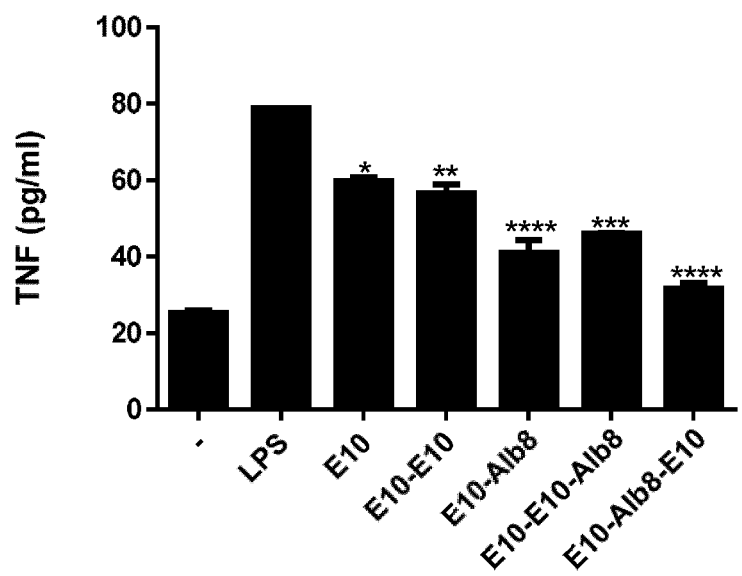

FIG. 3 shows that anti-MIF E10 constructs can inhibit TNF secretion from LPS stimulated macrophages. Peritoneal exudates cells (PECs) from naive mice were treated with 1.67 µM of anti-MIF ISVD E10 constructs. After 18 hours of incubation, cell culture supernatants were collected for determination of the TNF concentration. Data are representative of 2 independent experiments (n=2) and shown as the mean±SEM. Statistical analysis was performed by comparing the induction of TNF of LPS stimulated cells in the presence of anti-MIF constructs to that of LPS alone stimulated cells. *: p<0.05, : p<0.01, *: p<0.001 or ****: p<0.0001

Figure 4A:
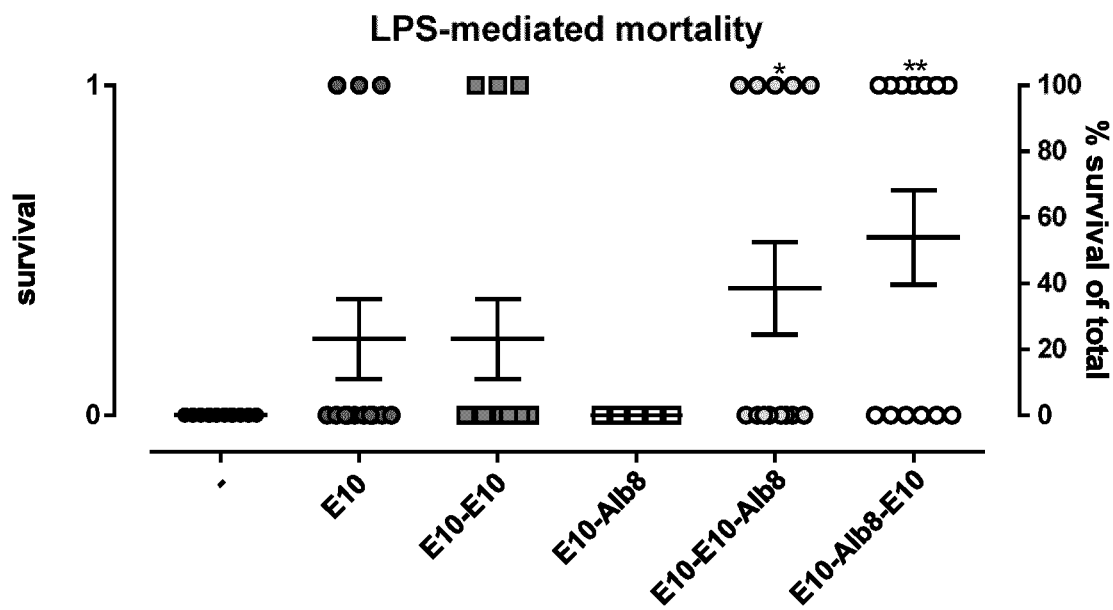
Figure 4B:
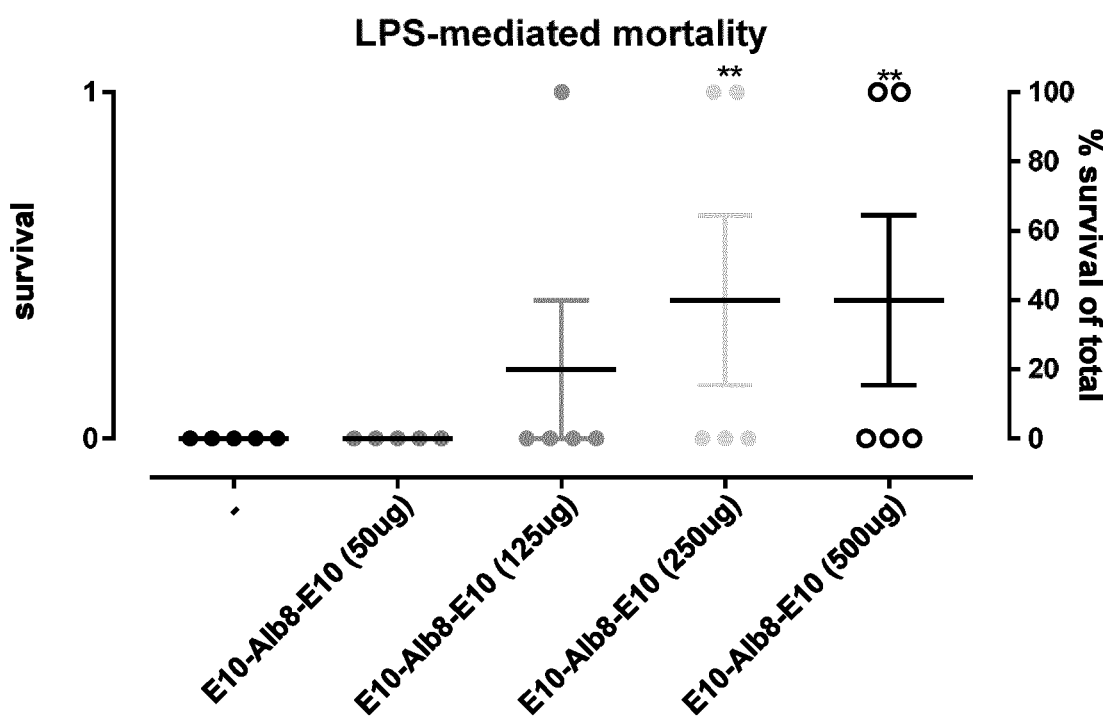

FIGS. 4A and 4B show that a half-life extended anti-MIF ISVD E10 construct is protective in a mouse model of endotoxemia. A) C57BL/6 mice were given a single injection of 12.5 mg/kg LPS alone or in combination with 25 mg/kg of MIF inhibitor E10 constructs and monitored for survival. Data is representative of 3 independent experiments (n=13). B) Dose kinetics of MIF inhibitor E10-Alb8-E10, whereby C57BL/6 mice were given a single co-injection of 12.5 mg/kg LPS and 25 mg/kg, 12.5 mg/kg, 6.25 mg/kg, or 2.5 mg/kg of the MIF inhibitor E10-Alb8-E10 construct and monitored for survival. Hereby, mice surviving 72 hours post LPS injection correspond to 1 and mice that died correspond to 0. Of note, mice surviving 72 hours post LPS injection recovered completely. For each group the % survival is depicted. Data is representative of 2 independent experiments (n=5) and shown as the mean±SEM *: p<0.05, **: p<0.01.

Figure 5:
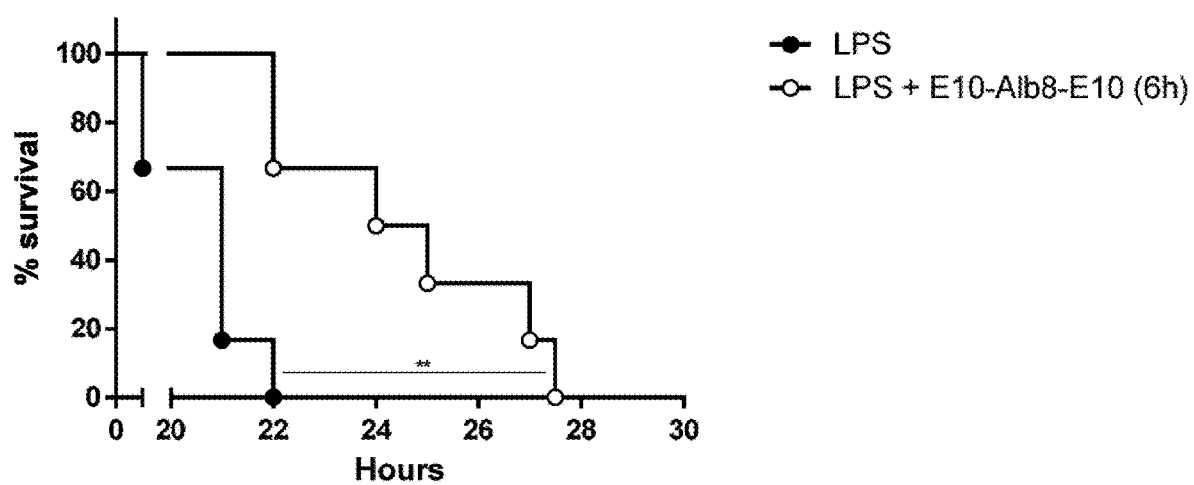

FIG. 5 shows that a half-life extended anti-MIF ISVD E10 construct given therapeutically attenuates endotoxemia. C57BL/6 mice were given a single lethal injection of 12.5 mg/kg LPS alone (filled circles) or followed by 25 mg/kg of MIF inhibitor E10-Alb8-E10 given 6 hours post LPS injection (open circles). Data is representative of 2 independent experiments (n=5) and shown as the mean±SEM (**: p<0.01).

Figure 6:
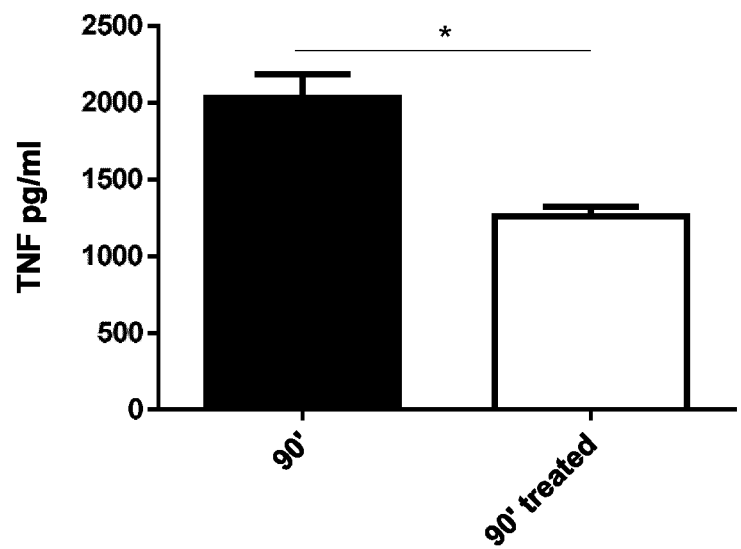

FIG. 6 shows that the MIF inhibitor E10-Alb8-E10 reduced peak serum TNF levels in endotoxin-treated mice. C57BL/6 mice were given a single injection of 12.5 mg/kg LPS alone or in combination with 25 mg/kg of MIF inhibitor E10-Alb8-E10 and 90 minutes later mice were sacrificed and serum tested in a TNF ELISA. Data is representative of 2 independent experiments and expressed as means±SEM (n=3). (*: p-value<0.05).

FIG. 7 shows the binding of anti-MIF ISVDs to different MIF peptides. Overlapping MIF peptides were biotinylated and coupled to a streptavidin biosensor using the BLItz® system. Binding of all available MIF ISVDs was assessed using the BLItz® system. Results are designated as signal ISVD-signal PBS, whereby delta values between 0.025-0.25 nm was designated as (+) and 0.25-1.50 nm as (++). The maximal signal obtained was 1.50 nm.

DETAILED DESCRIPTION

Definitions

Unless indicated or defined otherwise, all terms used have their usual meaning in the art, which will be clear to the skilled person. Reference is for example made to the standard handbooks, such as Sambrook et al. (Molecular Cloning: A Laboratory Manual (2nd.Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, Calif., 1981); Roitt et al. (Immunology (6th. Ed.) Mosby/Elsevier, Edinburgh, 2001), Roitt et al. (Roitt's Essential Immunology (10$^{th}$ Ed.) Blackwell Publishing, U K, 2001), and Janeway et al. (Immunobiology (6th Ed.) Garland Science Publishing/Churchill Livingstone, N.Y., 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews: Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

A nucleic acid sequence or amino acid sequence is considered to be "(in) essentially isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatography technique, such as polyacrylamide-gel electrophoresis.

The term "genetic fusion" as used herein refers to the coupling of individual nucleic acids, e.g. encoding ISVDs, via amide bonds, in which a nucleotide sequence encoding an ISVD is coupled via its 3'-terminus nucleic acid via a phosphodiester bond to the 5'-terminus nucleic acid of another nucleotide sequence encoding an ISVD, if appropriate via (nucleic acid) linkers of various lengths, e.g. a nucleotide sequence encoding an ISVD is coupled via its 3'-terminus nucleic acid via a phosphodiester bond to the 5'-terminus nucleic acid of a linker sequence, which is coupled via its 3'-terminus nucleic acid via a phosphodiester bond to the 5'-terminus nucleic acid of another nucleotide sequence encoding an ISVD (i.e. the ISVDs and optionally the linkers are genetically fused). Genetic fusion can be performed according to standard recombinant DNA protocols (supra), or as described in the Examples section, e.g. Garaicoechea et al. (2008, J Virol. 82: 9753-9764).

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". For instance, when a nucleotide sequence, amino acid sequence or polypeptide is said to "comprise" another nucleotide sequence, amino acid sequence or polypeptide, respectively, or to "essentially consist of" another nucleotide sequence, amino acid sequence or polypeptide, this may mean that the latter nucleotide sequence, amino acid sequence or polypeptide has been incorporated into the first mentioned nucleotide sequence, amino acid sequence or polypeptide, respectively, but more usually this generally means that the first mentioned nucleotide sequence, amino acid sequence or polypeptide comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" or "consist essentially of" and the like is meant that the polypeptide used herein either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins. Amino acid residues will be indicated according to the standard three-letter or one-letter amino acid code. Reference is made to Table A-2 on page 48 of WO 08/020079. Those amino acid sequences containing D-amino acids are not intended to be embraced by this definition. Any amino acid sequence that contains post-translationally modified amino acids may be described as the amino acid sequence that is initially translated using the symbols shown in this Table A-2 with the modified positions; e.g., hydroxylations or glycosylations, but these modifications shall not be shown explicitly in the amino acid sequence. Any peptide or protein that can be expressed as a sequence modified linkages, cross links and end caps, non-peptidyl bonds, etc., is embraced by this definition.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro or in vivo by recombinant methods as known in the art.

An amino acid sequence (such as an immunoglobulin single variable domain, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation $DG=RT \cdot \ln(K_D)$ (equivalently $DG=-RT \cdot \ln(K_A)$), where R equals the gas constant, T equals the absolute temperature and ln denotes the natural logarithm.

The $K_D$ for biological interactions which are considered meaningful (e.g. specific) are typically in the range of $10^{-12}$ M (0.001 nM) to $10^{-5}$ M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1} s^{-1}$. The on-rate may vary between $10^2 M^{-1} s^{-1}$ to about $10^7 M^{-1} s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^6 s^{-1}$ (near irreversible complex with a $t_{1/2}$ of multiple days) to $1 s^{-1}$ ($t_{1/2}=0.69$ s).

Specific binding of an antigen-binding protein, such as an ISVD, to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex.

The GYROLAB® immunoassay system provides a platform for automated bioanalysis and rapid sample turnaround (Fraley et al. 2013, Bioanalysis 5: 1765-74).

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules.

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as a dimer or polypeptide of the invention) molecule can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the immunoglobulin single variable domains, and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ liter/mol) is generally considered to indicate non-specific binding. Preferably, a monovalent immunoglobulin single variable domain of the invention will bind to the desired antigen with an affinity less than 500 nM, preferably less than 200 nM, more preferably less than 10 nM, such as less than 500 pM, such as e.g., between 10 and 5 nM or less. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

Another approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D = IC_{50}/(1 + c_{ref}/K_{Dref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half maximal inhibitory concentration ($IC_{50}$) is a measure of the effectiveness of a compound in inhibiting a biological or biochemical function, e.g. a pharmacological effect. This quantitative measure indicates how much of the MIF inhibitor (e.g. an ISVD or polypeptide of the invention) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). The $IC_{50}$ of a drug can be determined by constructing a dose-response curve and examining the effect of different concentrations of antagonist such as the MIF inhibitor of the invention (e.g. an ISVD or polypeptide of the invention) on reversing agonist activity. $IC_{50}$ values can be calculated for a given antagonist such as the MIF inhibitor of the invention (e.g. an ISVD or polypeptide of the invention) by determining the concentration needed to inhibit half of the maximum biological response of the agonist.

The term half maximal effective concentration ($EC_{50}$) refers to the concentration of a compound which induces a response halfway between the baseline and maximum after a specified exposure time. In the present context it is used as a measure of a MIF inhibitor's, such as a polypeptide's, ISVD's or Nanobody's potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the KD as accurate as possible. In other words, the $EC_{50}$ values may then be considered as KD values. The term "average KD" relates to the average KD value obtained in at least 1, but preferably more than 1, such as at least 2 experiments. The term "average" refers to the mathematical term "average" (sums of data divided by the number of items in the data).

It is also related to $IC_{50}$ which is a measure of a compound's inhibition (50% inhibition). For competition binding assays and functional antagonist assays $IC_{50}$ is the most common summary measure of the dose-response curve. For agonist/stimulator assays the most common summary measure is the $EC_{50}$. The inhibitor constant, Ki, is an indication of how potent an inhibitor is; it is the concentration required to produce half maximum inhibition. The absolute inhibition constant $K_i$ can be calculated by using the Cheng-Prusoff equation:

$$K_i = \frac{IC50}{\frac{[L]}{K_D} + 1}$$

in which [L] is the fixed concentration of the ligand.

A MIF inhibitor (such as a polypeptide, an immunoglobulin, an antibody, an immunoglobulin single variable domain, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-MIF).

A MIF inhibitor, such as an immunoglobulin single variable domain and/or polypeptide is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 2357768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gin; (c) polar, positively charged residues: His, Arg and Lys; (d) large aliphatic, nonpolar residues: Met, Leu, lie, Val and Cys; and (e) aromatic residues: Phe, Tyr and Trp. Particularly preferred conservative substitutions are as follows: Ala into Gly or into Ser; Arg into Lys; Asn into Gin or into His; Asp into Glu; Cys into Ser; Gin into Asn; Glu into Asp; Gly into Ala or into Pro; His into Asn or into Gin; Ile into Leu or into Val; Leu into Ile or into Val; Lys into Arg, into Gin or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.

The "amino acid difference" can be any one, two, three or maximal four substitutions, deletions or insertions, or any combination thereof, that either improve the properties of the MIF binder of the invention such polypeptide and/or ISVD of the invention or that at least do not detract too much from the desired properties or from the balance or combination of desired properties of the polypeptide of the invention. In this respect, the resulting MIF binder of the invention such polypeptide and/or ISVD of the invention should at least bind MIF with the same, about the same, or a higher affinity compared to the polypeptide comprising the one or more CDR sequences without the one, two, three or maximal four substitutions, deletions or insertions, said affinity as e.g. measured by surface plasmon resonance (SPR).

For example, and depending on the host organism used to express the MIF binder of the invention such polypeptide and/or ISVD of the invention, such deletions and/or substitutions may be designed in such a way that one or more sites for post-translational modification (such as one or more glycosylation sites) are removed, as will be within the ability of the person skilled in the art.

A "Nanobody family", "VHH family" or "family" as used in the present specification refers to a group of Nanobodies and/or VHH sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as the MIF binders of the invention, including immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

The terms "(cross)-block", "(cross)-blocked", "(cross)-blocking", "competitive binding", "(cross)-compete", "(cross)-competing" and "(cross)-competition" are used interchangeably herein to mean the ability of a MIF binder, such as an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which a MIF binder, immunoglobulin, antibody, immunoglobulin single variable domain, polypeptide or other binding agent is able to interfere with the binding of another to the target, and therefore whether it can be said to cross-block according to the invention, can be determined using competition binding assays. Particularly suitable quantitative cross-blocking assays are described in the Examples and include e.g. a fluorescence-activated cell sorting (FACS) binding assay with MIF expressed on cells. The extent of (cross)-blocking can be measured by the (reduced) channel fluorescence.

The following generally describes a suitable FACS assay for determining whether a MIF binder, such as an immunoglobulin, antibody, immunoglobulin single variable domain, polypeptide or other binding agent cross-blocks or is capable of cross-blocking according to the invention. It will be appreciated that the assay can be used with any of the MIF binders, such as the immunoglobulins, antibodies, immunoglobulin single variable domains, polypeptides or other binding agents described herein. The FACS instrument (e.g. FACS Canto; Becton Dickinson) is operated in line with the manufacturer's recommendations.

To evaluate the "(cross)-blocking" or "(cross)-com petition" between two binding agents (such as e.g. two polypeptides, immunoglobulin single variable domains and/or Nanobodies) for binding MIF, a FACS competition experiment can be performed using transfected cells overexpressing human MIF and the parental cells as background cell line. Different detection reagents can be used including e.g. monoclonal ANTI-FLAG® M2 antibody (Sigma-Aldrich, cat #F1804), monoclonal anti-C-myc antibody (Sigma-Aldrich, cat #WH0004609M2), monoclonal ANTI-HIS TAG antibody (Sigma-Aldrich, cat #SAB1305538), each labeled differently. A wide range of fluorophores can be used as labels in flow cytometry (see more at: http://www.thefcn.org/flow-fluorochromes). Fluorophores, or simply "fluors", are typically attached to the MIF binder (such as, e.g., the antibody, polypeptide, immunoglobulin single variable domains, or Nanobody) that recognizes MIF or to the antibody that is used as detection reagent. Various conjugated antibodies are available, such as (without being limiting) for example antibodies conjugated to Alexa Fluor®, DyLight®, Rhodamine, PE, FITC, and Cy3. Each fluorophore has a characteristic peak excitation and emission wavelength. The combination of labels which can be used will depend on the wavelength of the lamp(s) or laser(s) used to excite the fluorophore and on the detectors available.

A cross-blocking immunoglobulin, antibody, immunoglobulin single variable domain, polypeptide or other binding agent according to the invention can be determined according to routine procedures, known the person skilled in the art. For instance, a cross-blocking immunoglobulin, antibody, immunoglobulin single variable domain, polypeptide or other binding agent according to the invention is one which will bind to the MIF in a FACS cross-blocking assay such that during the assay and in the presence of a second immunoglobulin, antibody, immunoglobulin single variable domain, polypeptide or other binding agent the recorded fluorescence is between 80% and 0.1% (e.g. 80% to 4%) of the maximum fluorescence (measured for the separate labelled immunoglobulin, antibody, immunoglobulin single variable domain, polypeptide or other binding agent), specifically between 75% and 0.1% (e.g. 75% to 4%) of the maximum fluorescence, and more specifically between 70% and 0.1% (e.g. 70% to 4%) of maximum fluorescence (as just defined above). Other methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 7).

An amino acid sequence is said to be "cross-reactive" for two different antigens or antigenic determinants (such as e.g., serum albumin from two different species of mammal, such as e.g., human serum albumin and cyno serum albumin, such as e.g., MIF from different species of mammal, such as e.g., human MIF, rhesus MIF, mouse MIF if it is specific for (as defined herein) these different antigens or antigenic determinants.

The term "Macrophage migration inhibitory factor" (EC: 5.3.2.1), hereinafter referred to as "MIF" is also known as Glycosylation-inhibiting factor (GIF); L-dopachrome isomerase; L-dopachrome tautomerase; and Phenylpyruvate tautomerase. MIF is preferably human MIF ("hMIF") represented by UniProt accession number P14174-1 (SEQ ID NO: 89), rhesus MIF represented by UniProt accession number Q6DN04-1 (SEQ ID NO: 90), and/or mouse MIF ("mMIF") represented by UniProt accession number P34884-1 (SEQ ID NO: 91).

In the context of the present invention, "modulating" or "to modulate" generally means reducing or inhibiting an activity or effect of MIF and in particular human MIF (SEQ ID NO: 89) and/or mouse MIF (SEQ ID NO: 91), as measured using a suitable in vitro, cellular or in vivo assay (such as those mentioned herein). In particular, reducing or inhibiting an activity or effect of MIF and in particular human MIF (SEQ ID NO: 89) and/or mouse MIF (SEQ ID NO: 91), as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of MIF and in particular human MIF (SEQ ID NO: 89) and/or mouse MIF (SEQ ID NO: 91) in the same assay under the same conditions but without the presence of the polypeptide of the invention.

Modulating may for example involve reducing or inhibiting the binding of MIF to one of its substrates or receptors such as CD74, CXCR2, CXCR4, CXCR7 and/or ACKR3, and/or competing with other ligands. Alternatively, modulating may involve inhibiting or reducing internalization, inducing internalization in order to reduce binding to a MIF receptor, inhibiting or reducing CD74 level, inhibiting or reducing tautomerase activity, inhibiting or reducing (the stimulation of) a variety of inflammatory mediators, such as, e.g., IL-12, IL-17, IL-23, TNF, as well as IL-1β, IL-6, CCL2 and TGF-β and as such reducing signaling, and thus may inhibit a MIF dependent activity and/or effect, such as e.g. CD74 activation and/or chemotaxis via CXCR2, CXCR4 and/or CXCR7. In particular, binding of MIF ISVDs is sufficient to modulate MIF, its biological or pharmacological activity, and/or the biological pathways or signaling in which MIF is involved.

In the context of the present invention, "enhancing" or "to enhance" generally means increasing, potentiating or stimulating the activity of MIF, as measured using a suitable in vitro, cellular or in vivo assay (such as those mentioned herein). In particular, increasing or enhancing the activity of MIF, as measured using a suitable in vitro, cellular or in vivo assay (such as those mentioned herein), by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%, compared to the activity of MIF in the same assay under the same conditions but without the presence of the polypeptide of the invention.

A "synergistic effect" of two compounds is one in which the effect of the combination of the two agents is greater than the sum of their individual effects and is preferably statistically different from the controls and the single drugs.

A "MIF associated disease, disorder or condition" refers to a disease or symptom associated with the disease that is treatable by preventing, inhibiting, reducing or decreasing MIF activity, e.g. via the use of a MIF inhibitor as described herein. Exemplary MIF associated diseases, disorders or conditions include, but are not limited to, sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infection.

As used herein, the term "potency" is a measure of the biological activity of an agent, such as a MIF binder, e.g. a polypeptide, ISVD or Nanobody. Potency of an agent can be determined by any suitable method known in the art, such as for instance as described in the experimental section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, cell killing assays, reporter gene assays (e.g. NF-κB luciferase reporter assay), Tcell activation assay, cell surface receptor binding assays and assays to measure expression of known markers of activation or cytokine secretion, Phosphorylation of AKT assays, T/B and myeloid cell activation assays, cell surface receptor binding assays, chemotaxis assays, internalization assays, Glucocorticoid overriding assays, and assays to measure expression of known markers of activation or cytokine secretion, all well known in the art. In addition, also protein based assays allow obtaining more insight into the potency of the molecule to block/bind to its target, including but not limited to tautomerase assays, Fluorescence polarization assays, BiaCore, Crystallography, Chromatography, sedimentation velocity analytical ultracentrifugation, stability assays such as thermofluor, and Calorimetry). Finally, also validation of the MIF binder's potency in in vivo imaging applications including but not limited to computer tomography (CT), magnet resonance imaging (MRI), color Doppler ultrasound (US), single photon emission computed tomography (SPECT) and positron emission tomography (PET), allows obtaining more insight into their clinical potential as next generation of clinical modalities, all well known in the art.

In contrast, the "efficacy" of the polypeptide of the invention measures the maximum strength of the effect itself, at saturating polypeptide concentrations. Efficacy indicates the maximum response achievable from the MIF binder of the invention, such as e.g. the polypeptide and/or ISVD of the invention. It refers to the ability of a MIF binder to produce the desired (therapeutic) effect. The efficacy of a MIF binder of the invention can be evaluated using in vivo models, such as the mouse model of endotoxemia (for instance as set out in the Examples section).

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the standard handbooks, such as Kenneth et al (Chemical Stability of Pharmaceuticals: A Handbook for Pharmacists, John Wiley & Sons Inc, 1986) and M Gibaldi and D Perron ("Pharmacokinetics", Marcel Dekker, 2nd Rev. Edition, 1982). The terms "increase in half-life" or "increased half-life" are also as defined in paragraph o) on page 57 of WO 08/020079 and in particular refer to an increase in the t½-beta, either with or without an increase in the t½-alpha and/or the AUC or both.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1—CDR1—FR2—CDR2—FR3—CDR3—FR4. It is the immunoglobulin variable domain(s) that confer specificity to an antibody for the antigen by carrying the antigen-binding site.

The term "immunoglobulin single variable domain" (abbreviated as "ISVD" or "ISV"), interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "VH domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for VH domains given by Kabat et al. ("Sequence of proteins of immunological interest", US Public Health Services, NIH Bethesda, Md., Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of VH domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for VH domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dubel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human VH sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeable) for the preparation of a MIF binder, e.g. a polypeptide, which may optionally contain one or more further immunoglobulin single variable domains that can serve as a binding unit (i.e., against the same or another epitope on MIF and/or against one or more other antigens, proteins or targets than MIF).

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprise three immunoglobulin single variable domains, optionally linked via two linker sequences; whereas a "tetravalent" polypeptide may comprise four immunoglobulin single variable domains, optionally linked via three linker sequences; whereas a "pentavalent" polypeptide may comprise five immunoglobulin single variable domains, optionally linked via four linker sequences; whereas a "hexavalent" polypeptide may comprise six immunoglobulin single variable domains, optionally linked via five linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen (i.e., MIF) and at least one binding unit is directed against a second antigen (i.e., different from MIF) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., MIF) and at least one further immunoglobulin single variable domain directed against a second antigen (i.e., different from MIF), whereas a "trispecific" polypeptide of the invention is a polypeptide that comprises at least one immunoglobulin single variable domain directed against a first antigen (i.e., MIF), at least one further immunoglobulin single variable domain directed against a second antigen (i.e., different from MIF) and at least one further immunoglobulin single variable domain directed against a third antigen (i.e., different from both MIF and the second antigen); etc.

"Multiparatopic polypeptides", such as e.g.,"biparatopic polypeptides" or "triparatopic polypeptides", comprise or essentially consist of two or more binding units that each have a different paratope (as will be further described herein).

The present invention provides MIF binders, such as polypeptides and/or ISVDs (also referred to herein as "MIF binders of the invention" and "polypeptides of the invention" and "ISVDs of the invention", respectively) that have specificity for and/or that bind MIF, preferably human MIF and/or mouse MIF. MIF, which is also known as glycosylation-inhibiting factor (GIF), L-dopachrome isomerase, or phenylpyruvate tautomerase, is a protein that in humans is encoded by the MIF gene, which maps on chromosome Chr 22: 23.89-23.9 Mb. The MIF binders of the invention, such as the ISVDs and/or polypeptides of the invention preferably bind to human MIF (SEQ ID NO: 89; cf. UniProt accession number P14174), mouse MIF (SEQ ID NO: 91; cf. UniProt accession number P34884), rhesus MIF (SEQ ID NO: 90; UniProt accession number Q6DN04-1), and/or polymorphic variants or isoforms thereof.

MIF is a key player in the inflammatory response and contributes to several biological functions, including the control of cell cycle (through activation of ERK1/2), sensing of pathogen stimuli (e.g. upregulation of TLR4 expression), recruitment of immune cells (neutrophils, monocytes) and prevention of p53-mediated apoptosis of macrophages. MIF is released by activated cells, such as B/T-lymphocytes and myeloid cells (macrophages, monocytes, dendritic cells, neutrophils) as well as endothelial cells and platelets, and its activity is characterized by inter alia up-regulating the pro-inflammatory activity of these cells, including the stimulation of a variety of inflammatory mediators, such as IL-12, IL-17, IL-23, TNF, as well as IL-1β, IL-6, TGF-β and CCL2 (12, 63, 64, 65). Though MIF's pro-inflammatory effects are crucial for an effective host defense, elevated MIF levels can also contribute to the development of organ dysfunction and deleterious sequelae.

The MIF binders of the invention, such as the ISVDs and/or polypeptides of the invention, are preferably MIF inhibitors and may decrease MIF mediated signaling, e.g. inhibiting release of IL-12, IL-17, IL-23, TNF, IL-1β, IL-6, TGF-β and/or CCL2. Accordingly, the MIF binders (e.g. ISVDs and/or polypeptides) provided by the present invention can be used in a variety of therapeutic applications, such as in the treatment of a variety of acute and chronic MIF associated diseases, disorders and/or conditions, as will be further defined herein.

Based on extensive screening, characterization and combinatory strategies, the present inventors surprisingly observed that the MIF binders of the present invention (e.g. ISVDs and polypeptides comprising immunoglobulin single variable domains binding MIF) showed improved properties for modulating MIF activity (compared to the MIF binders described in the prior art).

More specifically, the present inventors surprisingly observed that the amino acid based MIF binders of the present invention had in vivo anti-MIF activity, even lacking an Fc-region. This is in contrast to the prior art antibodies, of which the activity is at least partly dependent on Fc-effector functions.

Binding of the MIF binders of the invention, such as the ISVDs and/or polypeptides of the invention, to MIF can be measured in various binding assays, commonly known in the art. Typical assays include (without being limiting) Fluorescent ligand binding assays, Radioligand binding assays, Surface plasmon resonance (SPR), Plasmon-wave-guide resonance (PWR), SPR imaging for affinity-based biosensors, Whispering gallery microresonator (WGM), Resonant waveguide grating (RWG), Biolayer Interferometry Biosensor (BIB) assays, Nuclear magnetic resonance (NMR), X-ray crystallography, Thermal denaturation assays (TDA), Isothermal titration calorimetry (ITC) and Whole cell ligand-binding assays such as Surface acoustic wave (SAW) biosensor and RWG biosensor assays. A preferred assay for measuring binding of the MIF binders of the invention, such as the ISVDs and/or polypeptides of the invention, to MIF is SPR, such as e.g. the SPR as described in the examples, wherein binding of the MIF binders of the invention, such as the ISVDs and/or polypeptides of the invention, to MIF was determined, wherein MIF was immobilized on a solid substrate. Some preferred KD values for binding of the MIF binders of the invention, such as the ISVDs and/or polypeptides of the invention, to MIF will become clear from the further description and examples herein.

In an embodiment of the invention, the MIF binders of the invention, such as the ISVDs and/or polypeptides of the invention, have an on rate constant (Kon) for binding to said MIF selected from the group consisting of at least about $10^2$ $M^{-1}$ $s^{-1}$, at least about $10^3$ $M^{-1}$ $s^{-1}$, at least about $10^4$ $M^{-1}$ $s^{-1}$, at least about $10^5$ $M^{-1}$ $s^{-1}$, at least about $10^6$ $M^{-1}$ $s^{-1}$, $10^7$ $M^{-1}$ $s^{-1}$, at least about $10^8$ $M^{-1}$ $s^{-1}$, at least about $10^9$ $M^{-1}$ $s^{-1}$, and at least about $10^{10}$ $M^{-1}$ $s^{-1}$, preferably as measured by surface plasmon resonance.

In an embodiment of the invention, the MIF binders of the invention, such as the ISVDs and/or polypeptides of the invention, have an off rate constant (Koff) for binding to said MIF selected from the group consisting of at most about $10^3$ $s^{-1}$, at most about $10^{-4}$ $s^{-1}$, at most about $10^{-5}$ $s^{-1}$, at most about $10^{-6}$ $s^{-1}$, at most about $10^7$ $s^{-1}$, at most about $10^{-8}$ $s^{-1}$, at most about $10^{-9}$ $s^{-1}$, and at most about $10^{-10}$ $s^{-1}$, preferably as measured by surface plasmon resonance.

In an embodiment of the invention, the MIF binders of the invention, such as the ISVDs and/or polypeptides of the invention, bind to said MIF with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such as less than 10 pM. Preferably, the KD is determined by SPR, for instance as determined by Proteon.

The $EC_{50}$ of the MIF binders of the invention, such as the ISVDs and/or polypeptides of the invention, can also be determined, such as, for example by a FACS assay as known in the art. Preferably, the polypeptides and ISVDs of the present invention may have $EC_{50}$ values in binding human MIF of $10^{-8}$ M or lower, more preferably of $10^{0.9}$ M or lower, or even of $10^{-10}$ M or lower, such as $10^{-11}$ M. For example, in such FACS binding assay, the MIF binders of the invention, such as the ISVDs and/or polypeptides of the invention, may have $EC_{50}$ values in binding human MIF between $10^{-11}$ M and $10^{-8}$ M, such as between $10^{0.9}$ M and $10^{-8}$ M, between $10^{-10}$ M and $10^{-9}$ M or between $10^{-11}$ M and $10^{-10}$ M.

The MIF binders of the invention, such as the ISVDs and/or polypeptides of the invention, bind MIF and can modulate the activity of MIF. Preferably, the MIF binders of the present invention decrease or inhibit, such as reducing or preventing, an activity of MIF. More particularly, the MIF binders of the present invention may inhibit the immune and inflammatory response of T-cells and B-cells, and/or the release of cytokines such as e.g. IL-12, IL-17, IL-23, TNF, IL-13, IL-6 and/or TGF-β as well as the chemokine CCL2. Modulation of MIF activity can be determined by a variety of assays, including but not limited to proliferation assays, cytotoxicity assays, cell killing assays, reporter gene assays, surface receptor binding or chemotaxis assays and assays to measure expression of known markers of activation or cytokine secretion, which are all well known in the art. For example, any one of several conventional assays for monitoring cytokine production (such as TNF) as a measure of inflammation can be used as described in the Examples section. One can also employ immunofluorescence and flow cytometry to monitor cytokine production on a cellular basis, and to monitor cell surface markers that reflect cellular activation states. A host of such markers are known, detecting antibodies are broadly commercially available, and the markers are well known in the art.

In an embodiment the present invention relates to a MIF binder (such as an ISVD or polypeptide of the invention), wherein said MIF binder inhibits an inflammatory immune response by more than about 10%, such as 20%, 30%, or 40% or even more than 50%, such as more than 60%, such as 70%, 80%, or even more than 90% such as 100%.

In an embodiment the present invention relates to a MIF binder (such as an ISVD or polypeptide of the invention), wherein said MIF binder inhibits tautomerase activity by more than about 10%, such as 20%, 30%, or 40% or even more than 50%, such as more than 60%, such as 70%, 80%, or even more than 90% such as 100%.

In an embodiment the present invention relates to a MIF binder (such as an ISVD or polypeptide of the invention), wherein said MIF binder inhibits a MIF activity by more than about 10%, such as 20%, 30%, or 40% or even more than 50%, such as more than 60%, such as 70%, 80%, or even more than 90% such as 100%.

In an embodiment the present invention relates to a MIF binder (such as an ISVD or polypeptide of the invention), wherein said MIF binder inhibits inflammation by more than about 10%, such as 20%, 30%, or 40% or even more than 50%, such as more than 60%, such as 70%, 80%, or even more than 90% such as 100%.

In some embodiments, the polypeptides of the invention decrease TNF production in an LPS induced TNF activation assay, as described in Examples 1.4 and 3.

In an embodiment the present invention relates to a MIF binder (such as an ISVD or polypeptide of the invention), wherein said MIF binder inhibits TNF-induction, preferably as assessed by an LPS stimulation assay by more than about 10%, such as 20%, 30%, or 40% or even more than 50%, such as more than 60%, such as 70%, 80%, or even more than 90% such as 100%.

In an embodiment the present invention relates to a MIF binder (such as an ISVD or polypeptide of the invention), wherein said MIF binder inhibits TNF-secretion by more than about 10%, such as 20%, 30%, or 40% or even more than 50%, such as more than 60%, such as 70%, 80%, or even more than 90% such as 100%.

Therapeutic effects of the MIF binders of the invention, such as the ISVDs and/or polypeptides of the invention, can further be evaluated in in vivo models, such as e.g. in mice, rats, pigs and/or primates, for instance in a mouse model of endotoxemia as described in Example 5.

Accordingly, the present invention also relates to MIF binders of the invention, such as the ISVDs and/or polypeptides of the invention, wherein the binding of said MIF binder to said MIF ameliorates, prevents, inhibits and/or treats a MIF associated disease, disorder or condition, such as sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections.

The present invention provides stretches of amino acid residues that are particularly suited for binding MIF. In particular, the invention provides stretches of amino acid residues which bind MIF and wherein the binding of said stretches to said MIF modulates an activity or effect of MIF, preferably decreases, inhibits, reduces, prevents an effect or an activity of MIF (as described above). These stretches of amino acid residues may be present in, and/or may be incorporated into a MIF binder of the invention, such as the ISVD and/or polypeptide of the invention, in particular in such a way that they form (part of) the antigen binding site of the MIF binder. These stretches of amino acid residues have been generated as CDR sequences of heavy chain antibodies or $V_{HH}$ sequences that were raised against MIF. These stretches of amino acid residues are also referred to herein as "CDR sequence(s) of the invention" (i.e., as "CDR1 sequence(s) of the invention", "CDR2 sequence(s) of the invention" and "CDR3 sequence(s) of the invention", respectively).

It should however be noted that the invention in its broadest sense is not limited to a specific structural role or function that these stretches of amino acid residues may have in an MIF binder of the invention, such as an ISVD and/or polypeptide of the invention, as long as these stretches of amino acid residues allow the MIF binder of the invention, such as the ISVD and/or polypeptide of the invention, to bind to MIF with a certain affinity and potency (as defined herein). Thus, generally, the invention in its broadest sense provides a MIF binder of the invention, such as an ISVD and/or polypeptide of the invention that are capable of binding to MIF with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire MIF binder of the invention, such as the ISVD and/or polypeptide of the invention, forms a binding domain and/or binding unit that is capable of binding to MIF. It should however also be noted that the presence of only one such CDR sequence in a MIF binder of the invention, such as an ISVD and/or polypeptide of the invention, may by itself already be sufficient to provide the MIF binder of the invention, such as the ISVD and/or polypeptide of the invention, the capacity of binding to MIF; reference is for example made to the so-called "Expedite fragments" as described in WO 03/050531.

In particular, a MIF binder of the invention, such as an ISVD and/or polypeptide of the invention, may be a MIF binder of the invention, such as an ISVD and/or polypeptide of the invention, that comprises one antigen binding site, wherein said antigen binding site comprises at least one stretch of amino acid residues that is chosen from the group consisting of the CDR1 sequences, CDR2 sequences and CDR3 sequences as described in Table 8 (or any suitable combination thereof). In a preferred aspect, however, the MIF binder of the invention, such as the ISVD and/or polypeptide of the invention, comprises more than one, such as two or more stretches of amino acid residues chosen from the group consisting of the CDR1 sequences of the invention, the CDR2 sequences of the invention and/or the CDR3 sequences of the invention. Preferably, the MIF binder of the invention, such as the ISVD and/or polypeptide of the invention, comprises three stretches of amino acid residues chosen from the group consisting of the CDR1 sequences of the invention, the CDR2 sequences of the invention and the CDR3 sequences of the invention, respectively. The combinations of CDRs that are mentioned herein as being preferred for the MIF binder of the invention, such as the ISVD and/or polypeptide of the invention, are listed in Table 8.

In a preferred embodiment, the present invention relates to a MIF binder of the invention, such as an ISVD and/or polypeptide of the invention, essentially consisting of 4 framework regions (FR1 to FR4, respectively) and 3 complementarity determining regions (CDR1 to CDR3, respectively), wherein:
 CDR1 is chosen from the group consisting of SEQ ID NOs: 23, 24, 25, 26, 27, 28, 29, 30, 31, 32 and 33;
 CDR2 is chosen from the group consisting of SEQ ID NOs: 45, 46, 47, 48, 49, 50, 51, 52, 53, 54, and 55; and
 CDR3 is chosen from the group consisting of SEQ ID NOs: 67, 68, 69, 70, 71, 72, 73, 74, 75, 76 and 77.

In a preferred embodiment, the present invention relates to a MIF binder of the invention, such as an ISVD and/or polypeptide of the invention, essentially consisting of 4 framework regions (FR1 to FR4, respectively) and 3 complementarity determining regions (CDR1 to CDR3, respectively), wherein:
 CDR1 is SEQ ID NO: 23, CDR2 is SEQ ID NO: 45, and CDR3 is SEQ ID NO: 67;
 CDR1 is SEQ ID NO: 24, CDR2 is SEQ ID NO: 46, and CDR3 is SEQ ID NO: 68;
 CDR1 is SEQ ID NO: 25, CDR2 is SEQ ID NO: 47, and CDR3 is SEQ ID NO: 69;
 CDR1 is SEQ ID NO: 26, CDR2 is SEQ ID NO: 48, and CDR3 is SEQ ID NO: 70;
 CDR1 is SEQ ID NO: 27, CDR2 is SEQ ID NO: 49, and CDR3 is SEQ ID NO: 71;
 CDR1 is SEQ ID NO: 28, CDR2 is SEQ ID NO: 50, and CDR3 is SEQ ID NO: 72;
 CDR1 is SEQ ID NO: 29, CDR2 is SEQ ID NO: 51, and CDR3 is SEQ ID NO: 73;
 CDR1 is SEQ ID NO: 30, CDR2 is SEQ ID NO: 52, and CDR3 is SEQ ID NO: 74;
 CDR1 is SEQ ID NO: 31, CDR2 is SEQ ID NO: 53, and CDR3 is SEQ ID NO: 75;
 CDR1 is SEQ ID NO: 32, CDR2 is SEQ ID NO: 54, and CDR3 is SEQ ID NO: 76; or
 CDR1 is SEQ ID NO: 33, CDR2 is SEQ ID NO: 55, and CDR3 is SEQ ID NO: 77;

In a preferred embodiment, the present invention relates to a MIF binder, such as an ISVD, wherein said ISVD has been chosen from the group consisting of SEQ ID NOs: 1-11.

It should be further noted that the invention is not limited as to the origin of the MIF binder of the invention, such as the ISVD and/or polypeptide of the invention, (or of the nucleic acid of the invention used to express it), nor as to the way that the MIF binder of the invention, such as the ISVD and/or polypeptide of the invention, or nucleic acid of the invention is (or has been) generated or obtained. Thus, the MIF binder of the invention, such as the ISVD and/or polypeptide of the invention, may be naturally occurring ISVDs (from any suitable species) or synthetic or semi-synthetic ISVDs and/or polypeptides.

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat. Biotech., 23: 1257, 2005), and binding moieties based on DNA or RNA including but not limited to DNA or RNA aptamers (Ulrich et al. Comb. Chem. High Throughput Screen 9: 619-32, 2006).

In the MIF binder of the invention, such as the ISVD and/or polypeptide of the invention, the CDRs may be linked to further amino acid sequences and/or may be linked to each other via amino acid sequences, in which said amino acid sequences are preferably framework sequences or are amino acid sequences that act as framework sequences, or together form a scaffold for presenting the CDRs.

According to a preferred, but non-limiting embodiment, the MIF binders of the invention, such as the ISVDs and/or polypeptides of the invention, comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the MIF binders of the invention, such as the ISVDs and/or polypeptides of the invention, have the structure FR1-CDR1-FR2-CDR2-FR3-CDR3-FR4, in which CDR1, CDR2 and CDR3 are as defined herein for the MIF binders of the invention, such as the ISVDs and/or polypeptides of the invention, and FR1, FR2, FR3 and FR4 are framework sequences. In such a MIF binder of the invention, such as an ISVD and/or polypeptide of the invention, the framework sequences may be any suitable framework sequence, and examples of suitable framework sequences will be clear to the skilled person, for example on the basis of the standard handbooks and the further disclosure and prior art mentioned herein.

Accordingly, a MIF binder of the invention, such as an ISVD and/or polypeptide of the invention, essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 23-33; and
    (b) amino acid sequences that have 4, 3, 2, or 1 amino acid(s) difference with the amino acid sequence of SEQ ID NO: 23 or with any of SEQ ID NOs: 23-33; and/or
  (ii) CDR2 is chosen from the group consisting of:
    (c) SEQ ID NOs: 45-55; and
    (d) amino acid sequences that have 4, 3, 2, or 1 amino acid(s) difference with the amino acid sequence of SEQ ID NO: 45 or with any of SEQ ID NOs: 45-55; and/or
  (iii) CDR3 is chosen from the group consisting of:
    (e) SEQ ID NOs: 67-77; and
    (f) amino acid sequences that have 3, 2, or 1 amino acid(s) difference with the amino acid sequence of SEQ ID NO: 67 or with any of SEQ ID NOs: 67-77.

A comparison of the CDRs of the MIF binders of the invention, such as the ISVDs and/or polypeptides of the invention, revealed a number of permissible amino changes in the CDRs, while retaining MIF binding. The sequence variability in the CDRs of all clones against the CDRs of E10, which was used as reference, is depicted in the Table 1.

Accordingly, the present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which CDR1 is chosen from the group consisting of
  (a) SEQ ID NO: 23; and
  (b) amino acid sequences that have 1, 2, 3 or 4 amino acid difference(s) with SEQ ID NO: 23, wherein
    at position 2 the R has been changed into F;
    at position 3 the T has been changed into S;
    at position 4 the L has been changed into I, S, F or A;
    at position 5 the S has been changed into R;
    at position 6 the N has been changed into S, T or I;
    at position 7 the S has been changed into Y, Q, H or V; and/or
    at position 8 the I has been changed into F, A, V or T; and/or
in which CDR2 is chosen from the group consisting of
  (a) SEQ ID NO: 45; and
  (b) amino acid sequences that have 1, 2, 3 or 4 amino acid difference(s) with SEQ ID NO: 45, wherein
    at position 2 the N has been changed into G or S;
    at position 3 the W has been changed into F or N;
    at position 4 the S has been changed into G, N or K;
    at position 5 the G has been changed into Y or F;
    at position 6 the T has been changed into S or G;
    at position 7 the S has been changed into M, T, V or L; and/or
    at position 8 the R has been changed into P or T, and/or
in which CDR3 is chosen from the group consisting of
  (a) SEQ ID NO: 67; and
  (b) amino acid sequences that have 1, 2 or 3 amino acid difference(s) with SEQ ID NO: 67, wherein
    at position 1 the A has been changed into S or V;
    at position 2 the A has been changed into K;
    at position 3 the R has been changed into G;
    at position 4 the S has been changed into G, I or P or is absent;
    at position 5 the S has been changed into A, L, G, D or V or is absent;
    at position 6 the T has been changed into G, N or R or is absent;
    a G is introduced between position 6 and 7 of SEQ ID NO: 67;
    at position 7 the M has been changed into Q or G or is absent;
    at position 8 the S has been changed into L, Q, T, I or R or is absent;
    at position 9 the A has been changed into T, E, D, P, V or N or is absent;
    at position 10 the T has been changed into N, Y or F or is absent;
    at position 11 the D has been changed into T; and/or
    at position 12 the Y has been changed into F or S.

Based on differences in amino acid sequences of the complementarity determining regions (CDRs), the MIF binders of the invention, such as the ISVDs and/or polypeptides of the invention, could further be separated into seven different families (Families I-VII, as depicted in Tables 4-6). Corresponding alignments are provided in Table 8. Each family is represented by one clone, except for Family III which was represented by 4 clones, and Family V, which was represented by 2 clones.

In an embodiment, the present invention relates to MIF binders of family Ill. Accordingly, the present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 28-31; and
    (b) amino acid sequences that have 2 or 1 amino acid(s) difference with the amino acid sequence of SEQ ID NO: 28; and/or
  (ii) CDR2 is chosen from the group consisting of:
    (c) SEQ ID NOs: 50-53; and
    (d) amino acid sequences that have 2 or 1 amino acid(s) difference with the amino acid sequence of SEQ ID NO: 50; and/or
  (iii) CDR3 is chosen from the group consisting of:
    (e) SEQ ID NOs: 72-75; and
    (f) amino acid sequences that have 2 or 1 amino acid(s) difference with the amino acid sequence of SEQ ID NO: 72.

In a particularly preferred embodiment, the present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which CDR1 is chosen from the group consisting of
(a) SEQ ID NO: 28; and
(b) amino acid sequences that have 1, or 2 amino acid difference(s) with SEQ ID NO: 28, wherein
at position 7 the Q has been changed into H; and/or
at position 8 the V has been changed into T;
and/or
in which CDR3 is chosen from the group consisting of
(a) SEQ ID NO: 72; and
(b) amino acid sequences that have 1 or 2 amino acid difference(s) with SEQ ID NO: 72, wherein
at position 7 the I has been changed into T; and/or
at position 8 the T has been changed into P.

In an embodiment, the present invention relates to MIF binders of family V. Accordingly, the present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 25-26; and
(b) amino acid sequences that have 2, or 1 amino acid(s) difference with the amino acid sequence of SEQ ID NO: 25; and/or
(ii) CDR2 is chosen from the group consisting of:
(c) SEQ ID NOs: 47-48; and
(d) amino acid sequences that have 2 or 1 amino acid(s) difference with the amino acid sequence of SEQ ID NO: 47; and/or
(iii) CDR3 is chosen from the group consisting of:
(e) SEQ ID NOs: 69-70; and
(f) amino acid sequences that have 4, 3, 2, or 1 amino acid(s) difference with the amino acid sequence of SEQ ID NO: 69.

In a particularly preferred embodiment, the present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which CDR1 is chosen from the group consisting of
(a) SEQ ID NO: 25; and
(b) amino acid sequences that have 1, or 2 amino acid difference(s) with SEQ ID NO: 25, wherein
at position 4 the F has been changed into S; and/or
at position 6 the S has been changed into T;
and/or
in which CDR3 is chosen from the group consisting of
(a) SEQ ID NO: 69; and
(b) amino acid sequences that have 1, 2, 3 or 4 amino acid difference(s) with SEQ ID NO: 69, wherein
at position 1 the V has been changed into S;
at position 6 the T has been changed into N;
at position 8 the D has been changed into E; and/or
at position 11 the Y has been changed into F.

The Examples demonstrate that exemplary MIF binder E10 was particularly useful. The present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which CDR1 is SEQ ID NO: 23, and/or in which CDR2 is SEQ ID NO: 45, and/or in which CDR3 is SEQ ID NO: 67. In particular, the present invention relates to a MIF binder of the invention, such as an ISVD and/or polypeptide of the invention, wherein said MIF binder of the invention, such as the ISVD and/or polypeptide of the invention, comprises or essentially consists of 4 framework regions (FR1 to FR4, respectively) and 3 complementarity determining regions (CDR1 to CDR3, respectively), in which: CDR1 comprises SEQ ID NO: 23, CDR2 comprises SEQ ID NO: 45, and CDR3 comprises SEQ ID NO: 67.

In a preferred aspect, the present invention provides a MIF binder of the invention, such as an ISVD and/or polypeptide of the invention, which is selected from any of SEQ ID NOs: 1-11.

The invention further relates to MIF binders, such as polypeptides and/or immunoglobulin single variable domains directed against MIF that bind the same epitope as is bound by any of the MIF binder of the invention, such as the ISVDs and/or polypeptides of the invention, more particularly SEQ ID NOs: 1-11.

In a particular aspect, the invention relates to a MIF binder, such as a polypeptides and/or immunoglobulin single variable domains directed against MIF that bind the same epitope as is bound by any of the MIF binders of the invention, such as the ISVDs and/or polypeptides of the invention, that belong to Family VII, Family V, Family I, Family II, Family III, Family IV and Family VI, more particularly SEQ ID NOs: 1-11.

The Examples demonstrate that clones A2, E5 and E10, which bind to the same epitopic region, are particularly suited for reducing TNFα secretion from LPS stimulated macrophages and inhibiting MIF D-dopachrome tautomerase activity (cf. FIGS. 1C and 1D). Without being bound by any theory, the inventors hypothesized that inhibition of these combined effects were effected via binding to a specific epitopic region.

In an aspect, the invention relates to a MIF binder, such as a polypeptide and/or immunoglobulin single variable domain directed against MIF that bind the same epitope as is bound by any one of the MIF binders of the invention, such as the ISVDs and/or polypeptides of the invention, that belong to Family VII, more particularly SEQ ID NO: 1.

The present invention relates to a MIF binder of the invention, such as a polypeptide or ISVD of the invention, wherein said MIF binder cross-blocks the binding of a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to MIF.

The present invention also relates to polypeptides and/or immunoglobulin single variable domains directed against MIF that cross-block the binding to MIF of at least one of the MIF binders of the invention, such as the ISVDs and/or polypeptides of the invention, preferably SEQ ID NOs: 1-11 and/or that are cross-blocked from binding to MIF by at least one of the MIF binders of the invention, such as an ISVD and/or polypeptide of the invention, preferably SEQ ID NOs: 1-11.

The present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to MIF, and which competes for binding to MIF with the MIF binder of the invention such as an ISVD or polypeptide according to the invention.

Representative MIF binders of the present invention having the CDRs described above are shown in Table 8.

In one aspect, the MIF binder of the invention, such as the ISVD and/or polypeptide of the invention, has the same number of amino acids within its sequence compared to any one of SEQ ID NOs: 1-11. In another aspect, the monovalent polypeptide has an amino acid sequence between position 8 and position 106 (according to Kabat numbering) that has 89% or more sequence identity, such as 90% or 95% sequence identity compared to any one of SEQ ID NOs: 1-11. Preferably, the MIF binder of the invention, such as the ISVD and/or polypeptide of the invention, has the same number of amino acids within its sequence compared to any one of SEQ ID NOs: 1-11 and the MIF binder of the invention, such as the ISVD and/or polypeptide of the invention, has an amino acid sequence between position 8 and position 106 (according to Kabat numbering) that has 89% or more sequence identity such as 90% or 95% sequence identity compared to any one of SEQ ID NOs: 1-11. In another preferred aspect, the MIF binder of the invention, such as the ISVD and/or polypeptide of the invention, belongs to Family VII, such as e.g. represented by SEQ ID NO: 1.

In another preferred aspect, the MIF binder of the invention, such as the ISVD and/or polypeptide of the invention, belongs to Family V, such as e.g. selected from any one of SEQ ID NOs: 3-4.

The invention also relates to a MIF binder, such as an ISVD or polypeptide, which has at least 80% amino acid identity (or sequence identity as defined herein), preferably at least 85% amino acid identity, more preferably at least 90% amino acid identity, such as 95%, 96%, 97%, 98%, 99% amino acid identity or more or even (essentially) 100% amino acid identity with at least one of the amino acid sequences of SEQ ID NOs: 1-11.

In a specific, but non-limiting aspect, the MIF binder of the invention may be a stretch of amino acid residues that comprises an immunoglobulin fold or a MIF binder that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding a receptor, such as CXCR2, CXCR4, CD74, CXCR7 and/or ACKR3. Accordingly, in a preferred aspect the MIF binder of the invention is an immunoglobulin, such as e.g. an immunoglobulin single variable domain.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the MIF binder of the invention is an immunoglobulin single variable domain such as a Domain antibody (or an amino acid sequence that is suitable for use as a domain antibody); a single domain antibody (or an amino acid that is suitable for use as a single domain antibody); a "dAb" (or an amino acid that is suitable for use as a dAb); a Nanobody®; a $V_{HH}$ sequence; a humanized $V_{HH}$ sequence; a camelized $V_H$ sequence; or a $V_{HH}$ sequence that has been obtained by affinity maturation. Again, suitable framework sequences will be clear to the skilled person, for example on the basis of the standard handbooks and the further disclosure and prior art mentioned herein.

Another particularly preferred class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" immunoglobulin single variable domain of the invention, respectively. This nucleic acid can then be expressed in a manner known per se, so as to provide the desired immunoglobulin single variable domains of the invention. Alternatively, based on the amino acid sequence of a naturally occurring $V_{HH}$ domain or $V_H$ domain, respectively, the amino acid sequence of the desired humanized or camelized immunoglobulin single variable domains of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized immunoglobulin single variable domains of the invention, respectively, can be designed and then synthesized de novo using techniques for nucleic acid synthesis known per se, after which the nucleic acid thus obtained can be expressed in a manner known per se, so as to provide the desired immunoglobulin single variable domains of the invention.

In particular, the framework sequences present in the MIF binders of the invention, such as the ISVDs and/or polypeptides of the invention, may contain one or more of Hallmark residues (as defined in WO 08/020079 (Tables A-3 to A-8)), such that the MIF binder of the invention is a Nanobody. Some preferred, but non-limiting examples of (suitable combinations of) such framework sequences will become clear from the further disclosure herein (see e.g., Table 8). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3).

More in particular, the invention provides MIF binders comprising at least one immunoglobulin single variable domain that is an amino acid sequence with the (general) structure FR1—CDR1—FR2—CR2CDR2—FR3—CDR-CDR3—FR4 in which FR1 to FR4 refer to framework regions 1 to 4, respectively, and in which CDR1 to CDR3 refer to the complementarity determining regions 1 to 3, respectively, and which:
  i) have at least 80%, more preferably 90%, even more preferably 95% amino acid identity with at least one of the amino acid sequences of SEQ ID NOs: 1-11 (see Table 8), in which for the purposes of determining the degree of amino acid identity, the amino acid residues that form the CDR sequences are disregarded. In this respect, reference is also made to Table 8, which lists the framework 1 sequences (SEQ ID NOs: 12-22), framework 2 sequences (SEQ ID NOs: 34-44), framework 3 sequences (SEQ ID NOs: 56-66) and framework 4 sequences (SEQ ID NOs: 78-88) of the immunoglobulin single variable domains of SEQ ID NOs: 1-11; or
  ii) combinations of framework sequences as depicted in Table 8;
  and in which:
  iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The MIF binders of the invention, such as the ISVDs and/or polypeptides of the invention, may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the MIF binders of the invention, such as the ISVDs and/or polypeptides of the invention, may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the MIF binder of the invention, such as the ISVD and/or polypeptide of the invention, contain the mutations according to one of (i) to (v) above (or a suitable combination thereof):
  the amino acid residue at position 11 is preferably chosen from L, V or K (and is most preferably V); and
  the amino acid residue at position 14 is preferably suitably chosen from A or P; and
  the amino acid residue at position 41 is preferably suitably chosen from A or P; and
  the amino acid residue at position 89 is preferably suitably chosen from T, V or L; and
  the amino acid residue at position 108 is preferably suitably chosen from Q or L; and
  the amino acid residue at position 110 is preferably suitably chosen from T, K or Q; and
  the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the MIF binders of the invention, such as the ISVDs and/or polypeptides of the invention, may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is again made to said US provisional applications as well as to WO 12/175741. In particular, a MIF binder of the invention, such as an ISVD and/or polypeptide of the invention, may contain such a C-terminal extension when it forms the C-terminal end of a protein, polypeptide or other compound or construct comprising the same (again, as further described in said US provisional applications as well as WO 12/175741).

A MIF binder of the invention may be an immunoglobulin, such as an immunoglobulin single variable domain, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

Another particularly preferred class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$—$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" immunoglobulin single variable domain of the invention, respectively. This nucleic acid can then be expressed in a manner known per se, so as to provide the desired immunoglobulin single variable domains of the invention. Alternatively, based on the amino acid sequence of a naturally occurring $V_{HH}$ domain or $V_H$ domain, respectively, the amino acid sequence of the desired humanized or camelized immunoglobulin single variable domains of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized immunoglobulin single variable domains of the invention, respectively, can be designed and then synthesized de novo using techniques for nucleic acid synthesis known per se, after which the nucleic acid thus obtained can be expressed in a manner known per se, so as to provide the desired immunoglobulin single variable domains of the invention.

These MIF binders of the invention, and in particular the ISVDs comprising the CDR sequences of the invention are particularly suited for use as building block or binding unit for the preparation of multivalent polypeptides.

As will be clear from the further description above and herein, the immunoglobulin single variable domains of the invention can be used as "building blocks" to form MIF binders of the invention, e.g., by suitably combining them with other groups, residues, moieties or binding units, in order to form compounds or constructs as described herein (such as, without limitations, the bi-/tri-/tetra-/multivalent and bi-/tri-/tetra-/multispecific polypeptides of the invention described herein) which combine within one molecule one or more desired properties or biological functions.

Accordingly, the MIF binders of the invention can be in essentially isolated form (as defined herein), or they may form part of a protein or polypeptide, which may comprise or essentially consist of one or more ISVDs that bind MIF and which may optionally further comprise one or more further amino acid sequences (all optionally linked via one or more suitable linkers). The present invention also relates to a protein or polypeptide that comprises or essentially consists of one or more ISVDs of the invention (or suitable fragments thereof). For multivalent and multispecific polypeptides containing one or more VHH domains and their preparation, reference is also made to Conrath et al. (J. Biol. Chem. 276: 7346-7350, 2001), as well as to for example WO 96/34103, WO 99/23221 and WO 2010/115998.

The relative affinities may depend on the location of the ISVDs in the resulting MIF binder such as the polypeptide of the invention. It will be appreciated that the order of the ISVDs in a MIF binder of the invention, e.g. a polypeptide of the invention (orientation) can be chosen according to the needs of the person skilled in the art. The order of the individual ISVDs as well as whether the MIF binder, e.g. polypeptide, comprises a linker is a matter of design choice. Some orientations, with or without linkers, may provide preferred binding characteristics in comparison to other orientations. For instance, the order of a first ISVD (e.g. ISVD 1) and a second ISVD (e.g. ISVD 2) in the MIF binder of the invention, e.g. polypeptide of the invention, can be (from N-terminus to C-terminus): (i) ISVD 1 (e.g. Nanobody 1)—[linker]—ISVD 2 (e.g. Nanobody 2); or (ii) ISVD 2 (e.g. Nanobody 2)—[linker]—ISVD 1 (e.g. Nanobody 1); (wherein the linker is optional). All orientations are encompassed by the invention. MIF binders such as polypeptides that contain an orientation of ISVDs that provides desired binding characteristics can be easily identified by routine screening, for instance as exemplified in the examples section.

The MIF binders of the invention can generally be prepared by a method which comprises at least one step of suitably linking the one or more immunoglobulin single variable domains of the invention to the one or more further groups, residues, moieties or binding units, optionally via the one or more suitable linkers, so as to provide the MIF binder of the invention. MIF binders of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted immunoglobulin single variable domains form a further aspect of the invention.

In an aspect the invention relates to a MIF binder of the invention, such as a polypeptide comprising at least one ISVD of the invention.

In an aspect the invention relates to a MIF binder of the invention, such as a polypeptide, that comprises at least two ISVDs according to the invention.

In an aspect the invention relates to a MIF binder of the invention, such as a polypeptide, wherein said at least two ISVDs can be the same or different.

In an aspect the invention relates to a MIF binder of the invention, such as a polypeptide, wherein said at least two ISVDs are independently chosen from the group consisting of SEQ ID NOs: 1-11.

In an aspect the invention relates to a MIF binder of the invention, such as a polypeptide, wherein each of said at least two ISVDs are represented by SEQ ID NO: 1.

In an aspect the invention relates to a MIF binder of the invention, such as a polypeptide, comprising at least one further ISV.

In an aspect the invention relates to a MIF binder of the invention, such as a polypeptide, comprising SEQ ID NO: 121.

In a specific, but non-limiting aspect of the invention, which will be further described herein, the MIF binders of the invention, such as polypeptides of the invention have an increased half-life in serum (as further described herein) compared to the immunoglobulin single variable domain from which they have been derived. For example, an immunoglobulin single variable domain of the invention may be linked (chemically or otherwise) to one or more groups or moieties that extend the half-life (such as PEG), so as to provide a derivative of an amino acid sequence of the invention with increased half-life.

As demonstrated in the examples, half-life extension did not affect potency substantially. To the contrary, half-life extended constructs demonstrated increased advantageous effects, which appeared to be independent of serum binding. This indicates that half-life extended constructs are still capable of binding simultaneously to their respective targets.

In a specific aspect of the invention, a MIF binder of the invention, such as a polypeptide of the invention may have an increased half-life, compared to the corresponding amino acid sequence of the invention. Some preferred, but non-limiting examples of such MIF binders of the invention, such as polypeptides of the invention, will become clear to the skilled person based on the further disclosure herein, and for example comprise immunoglobulin single variable domains or polypeptides of the invention that have been chemically modified to increase the half-life thereof (for example, by means of pegylation); MIF binders of the invention, such as ISVDs and/or polypeptides of the invention that comprise at least one additional binding site for binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of MIF binders of the invention, such as polypeptides of the invention, which comprise such half-life extending moieties or immunoglobulin single variable domains will become clear to the skilled person based on the further disclosure herein; and for example include, without limitation, polypeptides in which the one or more immunoglobulin single variable domains of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb" 's, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins, such as, without limitation, the proteins and peptides described in WO 91/01743, WO 01/45746, WO 02/076489, WO2008/068280, WO2009/127691 and PCT/EP2011/051559.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such MIF binders of the invention, such as polypeptides of the invention, have a serum half-life e.g. in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such MIF binders of the invention, such as polypeptides of the invention, exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a MIF binder of the invention, such as a polypeptide of the invention, comprising at least a first immunoglobulin single variable domain (ISVD); and further comprising one or more (preferably one) serum albumin binding immunoglobulin single variable domain as described herein, e.g. the serum albumin binding immunoglobulin single variable domain of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92 or Alb223 (cf. Table 11).

Accordingly, the present invention relates to a MIF binder of the invention such as a polypeptide as described herein, further comprising a serum protein binding moiety or a serum protein.

The present invention relates to a MIF binder of the invention such as a polypeptide as described herein, wherein said serum protein binding moiety binds serum albumin.

The present invention relates to a MIF binder of the invention such as a polypeptide as described herein, wherein said serum protein binding moiety is an immunoglobulin single variable domain binding serum albumin.

The present invention relates to a MIF binder of the invention, such as a polypeptide of the invention, wherein said ISVD binding serum albumin essentially consists of 4 framework regions (FR1 to FR4, respectively) and 3 complementarity determining regions (CDR1 to CDR3 respectively), in which CDR1 is SFGMS (SEQ ID NO: 116), CDR2 is SISGSGSDTLYADSVKG (SEQ ID NO: 117), and in which CDR3 is GGSLSR (SEQ ID NO: 118).

The present invention relates to a MIF binder of the invention such as a polypeptide as described herein, wherein said ISVD binding serum albumin comprises Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92 or Alb223 [SEQ ID NOs: 103-115 and 123-124, respectively].

In an embodiment, the present invention relates to MIF binder, such as a polypeptide, wherein said serum protein binding moiety is a non-antibody based polypeptide.

In an embodiment, the present invention relates to MIF binder, such as a polypeptide, wherein said serum protein binding moiety is a non-antibody based polypeptide (e.g. PEG).

In an aspect, the present invention relates to a compound or construct as described herein comprising one or more other groups, residues, moieties or binding units, preferably chosen from the group consisting of a polyethylene glycol molecule, serum proteins or fragments thereof, binding units that can bind to serum proteins, an Fc portion, and small proteins or peptides that can bind to serum proteins.

In the MIF binders of the invention, such as the polypeptides of the invention, the two or more building blocks, ISVDs, such as e.g. Nanobodies, and the optionally one or more polypeptides one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_xser_y)_z$, such as (for example $(gly_4ser)_3$ or $(gly_3ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table 12.

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, polyethylene glycol moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final the MIF binder of the invention, such as the polypeptide of the invention, including but not limited to the affinity, specificity or avidity for a chemokine, or for one or more of the other antigens. Based on the disclosure herein, the skilled person will be able to determine the optimal linker(s) for use in a specific MIF binder of the invention, such as the polypeptide of the invention, optionally after some limited routine experiments.

For example, in multivalent polypeptides of the invention that comprise building blocks, ISVDs or Nanobodies directed against a first and second target, the length and flexibility of the linker are preferably such that it allows each building block, ISVD or Nanobody of the invention present in the polypeptide to bind to its cognate target, e.g. the antigenic determinant on each of the targets. Again, based on the disclosure herein, the skilled person will be able to determine the optimal linker(s) for use in a specific MIF binder of the invention, such as a polypeptide of the invention, optionally after some limited routine experiments.

It is also within the scope of the invention that the linker(s) used confer one or more other favourable properties or functionality to the MIF binders of the invention, such as the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the MIF binders of the invention, such as the polypeptides of the invention, these linkers may be the same or different. Again, based on the disclosure herein, the skilled person will be able to determine the optimal linkers for use in a specific MIF binder of the invention, such as a polypeptide of the invention, optionally after some limited routine experiments.

Usually, for easy of expression and production, a MIF binder of the invention, such as a polypeptide of the invention, will be a linear polypeptide. However, the invention in its broadest sense is not limited thereto. For example, when a MIF binder of the invention, such as a polypeptide of the invention, comprises three of more building blocks, ISVDs or Nanobodies, it is possible to link them by use of a linker with three or more "arms", which each "arm" being linked to a building block, ISVD or Nanobody, so as to provide a "star-shaped" construct. It is also possible, although usually less preferred, to use circular constructs.

Accordingly, the present invention relates to a MIF binder of the invention, such as a polypeptide of the invention, wherein said ISVDs are directly linked to each other or are linked via a linker.

Accordingly, the present invention relates to a MIF binder of the invention, such as a polypeptide of the invention, wherein a first ISVD and/or a second ISVD and/or possibly an ISVD binding serum albumin are linked via a linker.

Accordingly, the present invention relates to a MIF binder of the invention, such as a polypeptide of the invention, wherein said linker is chosen from the group consisting of linkers of 5GS, 7GS, 9GS, 10GS, 15GS, 18GS, 20GS, 25GS, 30GS, 35GS, poly-A, [SEQ ID NOs: 92-102], 8GS, 40GS, G1 hinge, 9GS-G1 hinge, llama upper long hinge region, and G3 hinge [SEQ ID NOs: 125-130].

Accordingly, the present invention relates to a MIF binder of the invention, such as a polypeptide of the invention, wherein said polypeptide is chosen from the group consisting of SEQ ID NOs: 119-122.

In the present invention it was shown in a relevant animal model that inhibiting MIF by the MIF binders of the invention, the results of (excessive or over) inflammation were ameliorated and/or delayed. The pharmacologic effect of the MIF binders of the invention, such as polypeptides and/or ISVDs of the invention therefore will reside eventually in inhibiting or impairing at least one, but preferably more than one activity or effect of MIF.

MIF can have a deleterious effect in one or more of sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections.

The present invention relates to a MIF binder of the invention, such as a polypeptide and/or ISVD as described herein, for use in treating a subject in need thereof as detailed above, e.g. ameliorates, prevents, inhibits and/or treats a MIF associated disease, disorder or condition.

The present invention relates to a pharmaceutical composition comprising a MIF binder of the invention, such as a polypeptide and/or ISVD as described herein.

The present invention relates to a method for delivering a prophylactic and/or therapeutic MIF binder of the invention, such as a polypeptide and/or ISVD to a specific location, tissue or cell type in the body, the method comprising the steps of administering to a subject in need thereof as mentioned above a MIF binder of the invention, such as a polypeptide and/or ISVD as described herein.

The present invention relates to a method for treating a subject in need thereof comprising administering a MIF binder of the invention, such as a polypeptide and/or ISVD as described herein.

The term "treating a subject in need thereof" as used herein refers to any method that results in a reduction in, amelioration of, prevention of and/or inhibition of the severity of symptoms (e.g., inflammation, cell recruitment and proliferation, tissue injury, anemia, lethality) or number of symptoms, associated with any of the MIF associated diseases, disorders or conditions described above in a subject.

Accordingly, the invention relates to a method for treating a subject in need thereof, comprising administering a MIF binder of the invention, such as a polypeptide and/or ISVD as described herein, wherein said subject recovers from inflammation.

In the above methods, the MIF binder of the invention, such as e.g. ISVDs and/or polypeptides of the invention and/or the compositions comprising the same can be administered in any suitable manner, depending on the specific pharmaceutical formulation or composition to be used. Thus, the MIF binder of the invention, such as e.g. ISVDs and/or polypeptides of the invention and/or the compositions comprising the same can for example be administered orally, intraperitoneally (e.g. intravenously, subcutaneously, intramuscularly, or intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease, disorder or condition to be prevented or treated and other factors well known to the clinician.

The clinician will generally be able to determine a suitable treatment regimen, depending on factors such as the stage of the disease to be treated, the severity of the MIF associated disease, disorder or condition to be treated and/or the severity of the symptoms thereof, the specific the MIF binder of the invention, such as e.g. ISVDs and/or polypeptides of the invention and/or the compositions to be used, the specific route of administration and pharmaceutical formulation or composition to be used, the age, gender, weight, diet, general condition of the patient, and similar factors well known to the clinician.

Generally, the treatment regimen will comprise the administration of one or more MIF binders of the invention, such as e.g. ISVDs and/or polypeptides of the invention and/or the compositions of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of a MIF associated disease, disorder or condition mentioned herein and depending on the severity and stage of the specific disease, disorder or condition to be treated, the potency of the specific MIF binder of the invention, such as ISVD and/or polypeptide of the invention to be used, the specific route of administration and the specific pharmaceutical formulation or composition used, the MIF binder of the invention, such as the ISVD and/or polypeptide of the invention will generally be administered in an amount between 1 gram and 0.01 milligram per kg body weight per day, preferably between 0.1 gram and 0.01 milligram per kg body weight per day, such as about 0.1, 1, 10, 100 or 1000 milligram per kg body weight per day, e.g. from 0.1 mg per kg to 25 mg per kg of the subject's body weight; either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

The MIF binder of the invention, such as the ISVD and/or polypeptide of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgment.

In one aspect, the disclosure provides methods for the administration of a MIF binder of the invention, such as the ISVD and/or polypeptide of the invention. In some embodiments, the MIF binder of the invention, such as the ISVD and/or polypeptide of the invention is administered as a pharmaceutical composition. The pharmaceutical composition, in addition to the MIF binder of the invention, such as the ISVD and/or polypeptide of the invention, includes a pharmaceutically-acceptable carrier.

The term "pharmaceutical composition," as used herein, represents a composition containing a MIF binder as described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier or excipient" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the disclosure include those suitable for oral, nasal, topical (including buccal and sublingual), rectal, vaginal and/or parenteral administration. The formulations may conveniently be presented in unit dosage form and may be prepared by any methods well known in the art of pharmacy.

The amount of active ingredient (e.g., MIF binder of the invention) which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In an aspect, the present invention relates to a composition comprising a MIF binder of the invention, such as an ISVD and/or polypeptide of the invention, which further comprises at least one pharmaceutically acceptable carrier, diluent or excipient and/or adjuvant, and optionally comprises one or more further pharmaceutically active polypeptides and/or compounds.

In an aspect, the present invention relates to a composition a MIF binder of the invention, such as the ISVD and/or polypeptide of the invention for use as a medicament.

In an aspect, the present invention relates to a composition, the a MIF binder of the invention, such as the ISVD and/or polypeptide of the invention, or the compound or construct as described herein, for use in preventing or treating sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections.

In an aspect, the present invention relates to a method for preventing or treating sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections, wherein said method comprises administering, to a subject in need thereof, a pharmaceutically active amount of at least a composition according to the invention, a MIF binder of the invention, such as the ISVD and/or polypeptide of the invention the immunoglobulin, to a person in need thereof.

In an aspect, the present invention relates to the use of a MIF binder of the invention, such as the ISVD and/or polypeptide of the invention, a compound or construct according to the invention, or a composition according to the invention, in the preparation of a pharmaceutical composition for treating or preventing sepsis, septic shock, diabetes, autoimmune hepatitis (AIH), glomerulonephritis (GN), inflammatory bowel diseases (IBD), chronic obstructive pulmonary disease (COPD), myocardial ischemia-reperfusion injury, anemia of inflammation and chronic disease (AI/ACD), rheumatoid arthritis (RA), polychondritis, multiple sclerosis (MS), Guillain-Barré syndrome, Alzheimer's disease, psoriasis, airway inflammation, such as asthma and acute respiratory distress syndrome (ARDS), atherosclerosis, uveitis, systemic lupus erythematosus (SLE) and protozoan infections, such as African trypanosomosis, and *Plasmodium* infections.

In an aspect, the present invention relates to a kit comprising a MIF binder of the invention, such as the ISVD and/or polypeptide of the invention, a vector as defined above, or a host cell as defined above.

In an aspect, the present invention relates to a compound or construct that comprises or essentially consists of a MIF binder of the invention, such as the ISVD and/or polypeptide of the invention, and which further comprises one or more other groups, residues, moieties or binding units, optionally linked via one or more peptidic linkers.

In an aspect, the present invention relates to a nucleic acid encoding a MIF binder of the invention, such as the ISVD and/or polypeptide of the invention, or a compound or construct as described herein.

In an aspect, the present invention relates to an expression vector comprising a nucleic acid of the invention.

In an aspect, the present invention relates to a host or host cell comprising a nucleic acid as described herein, e.g. encoding a MIF binder of the invention, such as the ISVD and/or polypeptide of the invention, or an expression vector as described herein.

In an aspect, the present invention relates to also to a method for producing encoding a MIF binder of the invention, such as the ISVD and/or polypeptide of the invention, said method at least comprising the steps of:
a) expressing, in a suitable host cell or host organism or in another suitable expression system, a nucleic acid sequence as described herein; optionally followed by:
b) isolating and/or purifying the encoding a MIF binder of the invention, such as the ISVD and/or polypeptide of the invention.

In an aspect, the present invention relates to a composition comprising at least encoding a MIF binder of the invention, such as an ISVD and/or polypeptide of the invention, a compound or construct according to the invention, or a nucleic acid according to the invention.

In an embodiment, the MIF binders of the invention, such as the polypeptides and/or ISVDs of the invention comprise one or more functional groups, residues or moieties. Preferably, said one or more functional groups, residues or moieties is chosen from the group of diagnostic and labelling agents.

In view of the specificity, the MIF binders of the invention, such as the polypeptides and/or ISVDs of the invention are also very suitable for conjugation to imaging agents also indicated herein as labelling agents. Suitable imaging agents for conjugating to antibodies are well known in the art, and similarly useful for conjugating to the MIF binders of the invention, such as the polypeptides and/or ISVDs of the invention. Suitable imaging agents include but are not limited to molecules preferably selected from the group consisting of organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

Accordingly, the present invention relates to a MIF binder of the invention, such as a polypeptides and/or ISVD of the invention, further comprising an imaging agent, including, but not limited to a molecule preferably selected from the group consisting of organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

Other suitable imaging agents, such as labels will be clear to the skilled person, and for example include moieties that can be detected using NMR or ESR spectroscopy. For instance, the MIF binders of the invention, such as the polypeptides and/or ISVDs of the invention can be radiolabeled with $^{89}$Zr. Such labelled MIF binders of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label. In a preferred embodiment, the radiolabeled MIF binders of the invention are detected via microPET imaging. Images can be reconstructed using AMIDE Medical Image Data Examiner software (version 1.0.4, Stanford University).

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. The Figures and the Experimental Part/Examples are only given to further illustrate the invention and should not be interpreted or construed as limiting the scope of the invention and/or of the appended claims in any way, unless explicitly indicated otherwise herein. Various modifications of the invention in addition to those shown and described herein will become apparent to those skilled in the art from the foregoing description and fall within the scope of the appended claims. The advantages and objects of the invention are not necessarily encompassed by each embodiment of the invention.

The entire contents of all of the references (including literature references, issued patents, published patent applications, and co pending patent applications) cited throughout this application are hereby expressly incorporated by reference, in particular for the teaching that is referenced hereinabove.

EXAMPLES

Example 1: Materials and Methods 1.1 Immunisation, Library Construction and Screening Immunisation, library construction and screening were performed by Ablynx™ and carried out as described in (25). Briefly, ISVD libraries were generated using peripheral blood lymphocytes (PBLs) isolated from three individual llamas immunized six consecutive times with recombinant human MIF$^{2-115}$ (rhMIF, R&D Systems). Three individual ISVD phage libraries were constructed following total RNA extraction and cDNA subcloning into the phagemid vector pAX50. The libraries, consisting of 3.3-9.5×10$^8$ transformants (96-100% insert), were subjected to two rounds (R1 and R2) of phage display panning using rhMIF. Subsequently, the crude periplasmic extract of 92 individual colonies from R2 was screened on rhMIF (0.05, 0.5 or 5

μg/ml) and detected using anti-c-Myc IgG and anti-mouse-HRP (Sigma-Aldrich). Selected anti-MIF ISVDs were recloned in the pAX100 expression vector and transformed in E. coli WK6 for further purification and stored at −80° C. in LB-medium supplemented with 50% glycerol.

1.2 Expression and Purification of Anti-MIF ISVDs

Expression and purification of ISVDs was as previously described (26), with the exception that kanamycin (Duchefa Biochemie) was used instead of ampicillin. Briefly, 1 mL of the overnight culture was inoculated in 330 ml of Terrific Broth (TB) medium supplemented with 70 μg/ml kanamycin and 0.1% glucose and subsequently grown at 37° C. in shaking flasks (200 rpm). Cultures were grown until the $OD_{600nm}$ reached 0.6-0.8, induced by adding 1 mM isopropyl-β-D-thiogalactopyranoside (IPTG) and further incubated at 28° C. overnight (200 rpm). The periplasmic extract was obtained by harvesting the cells via centrifugation (11325×g, 8 min., 14° C.), resuspension in 4 ml of TES (0.5 mM EDTA, 0.2 M Tris-HCL, 0.5 M sucrose) and incubation on ice for 6 hours while shaking at 200 rpm. Next, 8 ml of TES/4 per pellet was added and after incubation at 4° C. overnight (200 rpm), the suspension was centrifuged (30 min., 11325×g, 4° C.) to collect the periplasmic extract. ISVDs were purified using immobilized metal affinity chromatography (IMAC) on a His-Trap column (GE Healthcare) and elution with 0.5M Imidazole (Sigma Aldrich) in PBS pH 7.5. The eluate was further purified on a Superdex 75 (10/300) or (16/600) gel filtration column (GE Healthcare) equilibrated with PBS using an Akta Explorer 10S or AktaXpress (GE Healthcare). The purity of all anti-MIF ISVDs was evaluated via 12% Bis/Tris gel analysis and the protein concentration was determined using Nanodrop (Isogen). All ISVDs were treated with PROSEP-Remtox (Immunosource, Belgium) and confirmed LPS free using the Limulus Amebocyte Lysate (LAL) Kinetic-QCL Kit (Cambrex) in accordance to the manufactures instructions. The ISVDs were either used immediately or stored at −20° C.

1.3 Generation of Multivalent Anti-MIF ISVD Constructs

Multivalent constructs of ISVD-E10 were generated and cloned in the pAX100 vector by Ablynx™. The different constructs consisted of bivalent (E10-E10) or serum half-life extended format ISVDs by the addition of a cross reactive mouse/human anti-serum albumin ISVD (E10-Alb8, E10-E10-Alb8, E10-Alb8-E10). Expression and purification of the ISVDs was as described above.

1.4 TNF ELISA Assay

The TNF levels of culture supernatants and serum were measured using a commercial ELISA kit (R&D systems) as described by the supplier.

1.5 Surface Plasmon Resonance

Surface plasmon resonance (SPR) experiments were performed on a BIAcore T200 system (GE Healthcare). Recombinant mouse MIF (rmMIF) or rhMIF (R&D systems) was immobilized on a CM5 chip (GE Healthcare). Briefly, the carboxylated dextran matrix was activated by injection of 0.2 M N-ethyl-N'-(3-diethylaminopropyl) carbodiimide (EDC) and 0.05 M N-hydroxysuccinimide (NHS) at a flow rate of 5 μl/min for 7 min. A rmMIF solution of 5 μg/ml prepared in coupling buffer (50 mM sodium acetate pH 4.0) was subsequently injected until 200 R.U. was immobilised. Next, the surface immobilisation was blocked by injection of 1 M ethanolamine hydrochloride for 7 min. As a reference, the surface in another flow cell was used and treated only with EDC, NHS, and ethanolamine. Data for the rmMIF-ISVD interaction were collected in the format of a kinetic titration (27). Sensorgrams for the anti-mMIF ISVDs/ISVD-constructs were collected at five different concentrations (½ serial dilution starting from 100, 150, 200 or 750 nM) plus a 0 concentration (injection of running buffer, i.e. HBS [10 mM Hepes (pH 7.5), 150 mM NaCl, 3.5 mM EDTA, 0.005% (v/v) Tween-20]) at a flow rate of 30 μl/min and a data collection rate of 10 Hz. Analyte injections were performed with association phases of 180 s and a dissociation phase of 600 s. This was followed by 5 pulses of 15 μl regeneration buffer (HBS+100 mM NaOH). Prior to data analysis, reference and zero concentration data were subtracted from the sensorgrams. The data were analyzed with a 1:1 Langmuir binding model (27). Data for the rhMIF-ISVD interaction were collected as described elsewhere (28) and analyzed with a 1:1 Langmuir binding model.

1.6 Differential Scanning Fluorimetry (Thermofluor)

Differential scanning fluorimetry experiments were carried out on a real-time PCR machine (Bio-Rad) in a 96-well plate format. The final volume in each well was 25 μl. For the buffer blank, 7.5 μl SYPRO orange dye (Life Technologies) was mixed with 17.5 μl PBS. For the ISVD samples, 7.5 μl SYPRO orange dye (Life Technologies) was mixed with 5 μl of the ISVD of interest at a stock concentration 2.5 mg/ml (final concentration 0.5 mg/ml) and 12.5 μl PBS. Data for all samples were collected in triplicate. To obtain buffer-corrected fluorescence signals for each ISVD, the averaged buffer data set was subtracted from the averaged protein data set. The buffer-corrected fluorescence signal (F) was plotted as a function of temperature (T) and fitted with the Boltzmann sigmoidal function to obtain the melting temperature (Tm) using the equation: $F=F0+(Fmax-F0)/(1+e^{((Tm-T)/a)})$. F0 and Fmax are the lowest (pre-transitional) and the highest (post-transitional) buffer-corrected fluorescence signals (expressed in AU) and a is the change in T corresponding to the most significant change in F (also called the slope of the transition region, expressed in AU/° C.).

1.7 Epitope Mapping

To determine the region within the MIF protein where the anti-MIF ISVDs are binding we used a similar approach as described by (20). Briefly, based on the amino acid sequence of human MIF taken from Swiss-Prot (P14174), synthetic overlapping peptides were designed whereby the N-terminal amino acid (Met) was omitted, as it is cleaved during processing of the MIF molecule. The peptide sequences are as described in (20), however, we included a biotin at the N-terminal region of the peptide. The peptides were ordered from http://peptide2.com and the BLItz® system (http://www.blitzmenow.com/PALL Life Sciences) was used to determine the binding potential of the different anti-MIF ISVDs. Each of the peptides (2.5 μM) was coupled to a streptavidin sensor. Subsequently, a single concentration of ISVD (0.67 μM) was added and binding observed for 120 s. Washing and regeneration was as recommended by the suppliers. For each peptide a blank run consisting of PBS only was used for obtaining a baseline. The binding signal obtained after 120 s is expressed in nm and was calculated as follows: signal ISVD-signal PBS.

1.8 Tautomerase Assay

The tautomerase assay was performed as described in (29). Briefly, the enzymatic reaction was initiated at 25° C. by adding 20 μl of the dopachrome methyl ester substrate (2 mM L-3,4-dihydroxyphenylalanine methyl ester and 4 mM sodium periodate) in a 96-well plate containing 200 μl of either recombinant mouse MIF (rmMIF) (83.3 nM) or rmMIF pre-incubated (1 hour at 37° C.) with ISVD (0.67 μM) in tautomerase assay buffer (50 mM potassium phosphate, 1 mM EDTA, pH 6.0) or with 10 μM ISO-1 ((S,R)-3-(4-hydroxyphenyl)-4,5-dihydro-5-isoxazole acetic acid methyl ester (Merck). The activity was determined by the semi-continuous reduction in signal measured at $OD_{475\,nm}$ for 5 minutes. ELISA plates were read using an $EL_x808$ Ultra micro plate reader spectrophotometer and Gen5 1.08 software.

1.9 In Vitro Inhibition Assay

Experiments were performed using either the human monocytic cell line THP-1 (ATCC), the murine macrophage cell line RAW264.7 (ATCC) or human peripheral blood monocytic cells (PBMC's) ex vivo peritoneal exudates cells (PECs). Human peripheral blood mononuclear cells (PBMCs) were isolated from buffy coats obtained from health donors (provided by the Belgian Red Cross—Flanders, Mechelen, Belgium) using Lymphoprep (Axis Shield PoC As, Norway) gradient centrifugation. Erythrocyte lysis was performed with ACK-lysis buffer (Gibco, Life Technologies) and blocked with 1×HBSS/5% FCS. The remaining PBMCs were washed 3 times with HBSS (Gibco, Life Technologies), resuspended in ME medium (RPMI 1640, 10% FCS, 300 μg/ml L-glutamine, 100 μg/ml penicillin, 100 μg/ml streptomycin, 0.02 mM β-mercaptoethanol, 1 mM non-essential amino acids, 1 mM sodium pyruvate), counted and brought at a concentration of $2*10^6$ cells/ml (stock solution) followed by a 3 hours adherence in a Petri dish. Next, non-adherent cells were removed and the adherent cells washed with RPMI, prior to adding 3 ml of TrypLE™ Express Enzyme (1×), phenol red (ThermoFischer Scientific) to detach the cells. Subsequently, RPMI/5% FCS was added to neutralize the buffer and cells pelleted using an Eppendorf Centrifuge 5810R at 394×g for 7 min. at 4° C. Finally, the cells were resuspended in ME medium, counted and brought at a concentration of $5*10^5$/ml (stock solution). PECs were obtained from $CO_2$-euthanized 7-8 weeks old female C57BL/6 mice (Janvier) or MIF deficient (Mif$^{-/-}$) C57Bl/6 mice (generated as described in (66) and bred in our animal facility) in accordance to the ethical commission regulations. Cells were harvested using 10 ml of ice-cold PBS and subsequently centrifuged (Eppendorf Centrifuge 5810R) at 394×g for 7 min. at 4° C. Next, the cells were re-suspended in ME medium (RPMI 1640, 10% FCS, 300 μg/ml L-glutamine, 100 μg/ml penicillin, 100 μg/ml streptomycin, 0.02 mM β-mercaptoethanol, 1 mM non-essential amino acids, 1 mM sodium pyruvate) and brought at a final concentration of $5*10^5$ cells/ml (stock solution). $1*10^5$ PBMC's or PECs were incubated in a Nunc Maxisorp 96 well flat bottom tissue culture plate either alone, in combination with 10 ng of LPS (*E. coli* 011:B4 or *E. coli* 011:B5), with or without 1.67 laM of each anti-MIF ISVD construct. Additionally, $5*10^5$ THP-1 or RAW264.7 cells were incubated in a Nunc Maxisorp 96 well flat bottom tissue culture plate either alone, in combination with 10 ng of LPS, with or without 500 nM of anti-MIF ISVD and/or 10 nM dexamethasone (Sigma Aldrich). The cells were incubated for 18 hours at 37° C., after which the supernatant was collected and tested in a mouse TNF ELISA (R&D systems).

1.10 Animal Experiments

All experiments complied with the ECPVA guidelines (CETS no 123) and were approved by the VUB Ethical Committee (Ethical Commission number 15-220-11). In order to induce endotoxic shock, 7-8 weeks old C57BL/6 female mice were injected intraperitoneally (i.p.) with 12.5 mg/kg of *E. coli* 011:B4 LPS (Invivogen) and monitored for survival over a period of 72 hours. Treatment experiments consisted of co-injection of LPS with anti-MIF ISVD-E10 constructs at concentrations of 25 mg/kg, 12.5 mg/kg, 6.25 mg/kg or 2.5 mg/kg. Alternatively, mice received anti-MIF ISVDE10 constructs (25 mg/kg) 6 hours post LPS injection, i.e. the moment mice start showing clinical signs/symptoms due to the LPS injection.

1.11 Statistics Statistical analysis (unpaired t-test or one-way ANOVA) was carried out using GraphPad Prism 6 statistical software. P-values<0.05 were considered statistically significant.

Example 2 Generation and Characterization of MIF Binding ISVDs

In order to obtain ISVDs against MIF, llamas were immunized with rhMIF followed by generation of phage display libraries from their peripheral blood lymphocytes. After two rounds of panning and selection on rhMIF, 11 anti-MIF binders were identified (Table 7). Based on differences in amino acid sequences of the complementarity determining regions (CDRs), the isolated Nanobodies could be separated into seven different families (Families I-VII, as depicted in Tables 4-6). Each family is represented by one clone, except for Family III which was represented by 4 clones, and Family V, which was represented by 2 clones.

The sequence variability of all clones against ISVD E10 is depicted in the Table 1 below. The amino acid sequences of the CDRs of clone E10 were used as reference, against which the CDRs of all other clones were compared (CDR1 starts at Kabat numbering 26, CDR2 starts at Kabat numbering 50, and CDR3 starts at Kabat numbering 95).

TABLE 1

Sequence variability of all clones versus ISVD E10 CDR1, CDR2 and CDR3.

| E10 CDR1 absolute numbering | SEQ ID 23 | | | | | | | |
|---|---|---|---|---|---|---|---|---|
| | 1 | 2 | 3 | 4 | 5 | 6 | 7 | 8 |
| E10 sequence variations | G | R | T | L | S | N | S | I |
| | | F | S | I | R | S | Y | F |
| | | | | S | | T | Q | A |
| | | | | F | | I | H | V |
| | | | | A | | | V | T |

TABLE 1-continued

Sequence variability of all clones versus ISVD E10 CDR1, CDR2 and CDR3.

| E10 CDR2 absolute | SEQ ID 45 | | | | | | | |
|---|---|---|---|---|---|---|---|---|
| numbering | 1 | 2 | 3 | 4 | 5 | 6 | 7 | 8 |
| E10 sequence variations | I | N<br>G<br>S | W<br>F<br>N | S<br>G<br>N<br>K | G<br>Y<br>F | T<br>S<br>G | S<br>M<br>T<br>V<br>L | R<br>P<br>T |

| E10 CDR3 absolute | SEQ ID 67 | | | | | | | | | | | |
|---|---|---|---|---|---|---|---|---|---|---|---|---|
| numbering | 1 | 2 | 3 | 4 | 5 | 6 | 7 | 8 | 9 | 10 | 11 | 12 |
| E10 sequence variations | A<br>S<br>V | A<br>K | R<br>G<br>I<br>P<br>— | S<br>G | S<br>A<br>L<br>G<br>D<br>V<br>— | T<br>G<br>N<br>R<br>— | —<br>G | M<br>Q<br>G<br>— | S<br>L<br>Q<br>T<br>I<br>R<br>— | A<br>T<br>E<br>D<br>P<br>V<br>N | T<br>N<br>Y<br>F<br>— | D<br>T | Y<br>F<br>S<br>— |

The sequence variability within Family III is depicted in Table 2 below. The amino acid sequences of the CDRs of clone A2 were used as reference, against which the CDRs of all other clones of Family III were compared (CDR1 starts at Kabat numbering 26, CDR2 starts at Kabat numbering 50, and CDR3 starts at Kabat numbering 95).

TABLE 2

Sequence variability of Family III clones versus ISVD A2 CDR1, CDR2 and CDR3.

| A2 CDR1 absolute | SEQ ID 28 | | | | | | | |
|---|---|---|---|---|---|---|---|---|
| numbering | 1 | 2 | 3 | 4 | 5 | 6 | 7 | 8 |
| A2 sequence variations | G | R | T | A | S | I | Q<br>H | V<br>T |

| A2 CDR2 absolute | SEQ ID 50 | | | | | | | |
|---|---|---|---|---|---|---|---|---|
| numbering | 1 | 2 | 3 | 4 | 5 | 6 | 7 | 8 |
| A2 sequence | I | G | W | N | Y | G | L | T |

| A2 CDR3 absolute | SEQ ID 72 | | | | | | | | | | |
|---|---|---|---|---|---|---|---|---|---|---|---|
| numbering | 1 | 2 | 3 | 4 | 5 | 6 | 7 | 8 | 9 | 10 | 11 |
| A2 sequence variations | A | A | R | I | G | T | I<br>T | T<br>P | Y | D | Y |

The sequence variability within Family V is depicted in Table 3. The amino acid sequences of the CDRs of clone E5 were used as reference, against which the CDRs of all other clones of Family V were compared (CDR1 starts at Kabat numbering 26, CDR2 starts at Kabat numbering 50, and CDR3 starts at Kabat numbering 95).

TABLE 3

Sequence variability of Family V clones versus ISVD E5 CDR1, CDR2 and CDR3.

| E5 CDR1 absolute | SEQ ID NO 25 | | | | | | | |
|---|---|---|---|---|---|---|---|---|
| numbering | 1 | 2 | 3 | 4 | 5 | 6 | 7 | 8 |
| E5 sequence variations | G | R | T | F<br>S | S | S<br>T | Y | F |

| E5 CDR2 absolute | SEQ ID NO 47 | | | | | | | |
|---|---|---|---|---|---|---|---|---|
| numbering | 1 | 2 | 3 | 4 | 5 | 6 | 7 | 8 |
| E5 sequence | I | N | F | S | G | G | T | T |

| E5 CDR3 absolute | SEQ ID NO 69 | | | | | | | | | | |
|---|---|---|---|---|---|---|---|---|---|---|---|
| numbering | 1 | 2 | 3 | 4 | 5 | 6 | 7 | 8 | 9 | 10 | 11 |
| E5 sequence variations | V<br>S | A | R | G | L | T | Q<br>N | D<br>E | Y | D | Y<br>F |

The anti-MIF ISVDs were purified and tested for binding to rhMIF as well as to rmMIF. SPR analysis revealed that all anti-MIF ISVDs, with the exception of ISVD F10 (SEQ ID NO: 9), displayed affinities for rmMIF and rhMIF in the nM range (Table 4 and Table 5, respectively).

Thermal stability is an important functional indicator for the use of binding agents in medicine and the in vivo activity of antibodies (30, 31). The thermal stability of the ISVDs was determined according to Example 1.6. All anti-MIF ISVDs, with the exception of ISVD F10 and ISVD H5, exhibited a good thermal stability ranging between 61–73° C. (Table 6), even without sequence optimization.

To determine the region within the MIF molecule the ISVDs were binding to, an epitope mapping study was performed using overlapping MIF peptides as described by (22) (see Example 1.7).

This epitope-mapping study suggests that the anti-MIF ISVDs cover different regions of the MIF protein (FIG. 7), whereby ISVD A2 seems to recognize an epitope closer to the N-terminal region of the protein (AA18-AA34), while ISVD C10 recognizes an epitope more to the C-terminal region of the protein (AA87-AA103). The anti-MIF ISVDs E5 and E10 recognize an epitope between AA35-68, while ISVDs B5, D2, D4 and D12 recognize a region between AA35-49 and ISVD H5 a region between AA45-58, while ISVD H9 binds a region between AA49-66. Only for ISVD F10 no clear binding region could be identified, which might be due to its low affinity for the intact protein (see Table 4) or due to the fact that it recognizes a structural epitope that is not represented in the tested peptides or eliminated by surface immobilization.

Example 3 ISVDs E5 and E10 Inhibit LPS-Mediated TNF Induction, MIF's Tautomerase Activity and can Override MIF's Inhibitory Effects on Glucocorticoids In Vitro Given that molecules able to block MIF's biological activity are beneficial to alleviate pathogenicity in many diseases (32), we determined if the anti-MIF ISVDs exhibited a MIF antagonistic capacity. In first instance, we determined if the ISVDs were able to block endotoxin (LPS)-induced TNF production by macrophages. It is well known that MIF, via CD74, activates the ETS/AP1 family of transcription factors which are important for the expression of TLR4, an integral component of the LPS receptor complex (33), and additionally leads to the expression of cell adhesion molecules and inflammatory cytokines (33-35).

To assess the inhibitory capacity of the anti-MIF ISVDs on MIF's biological activity, different in vitro assays were adopted. First, we measured their ability to inhibit MIF-mediated TNF induction by macrophages following LPS stimulation. In this context, it was shown that stimulation of macrophages with LPS results in MIF secretion, which in turn binds to the MIF receptor CD74 and triggers the secretion of TNF (33). As shown in FIG. 1C, ISVD E5 and ISVD E10 (used at a concentration of 0.5-1.67 µM; and also, to a lesser extent, ISVD A2) were capable of significantly decreasing TNF production by LPS stimulated RAW264.7 macrophages. Using the same in vitro conditions, (S,R)3-(4-hydroxyphenyl)-4,5-dihydro-5-isoxazole acetic acid methyl ester (ISO-1), which is the most well-known MIF antagonist at a concentration of 10 µM, was also able to inhibit TNF production by about 50% (1). Nevertheless, surprisingly, it seems that ISVDs E5 and E10, but also ISVD H9, are more efficient at inhibiting TNF induction than ISO-1.

In order to further substantiate the generality of the above observation, the assay was essentially repeated in different cells.

First, we determined their ability to inhibit MIF-mediated TNF induction by the human monocytic cell line THP-1, which was originally used to study MIF secretion (44), following LPS stimulation. It was shown before that stimulation of THP-1 cells with LPS results in MIF secretion, which in turn binds to the MIF receptor CD74 to augment the secretion of TNF (4,45, 46). As shown in FIG. 1A, only ISVD E5 and ISVD E10 were capable of significantly decreasing TNF production by LPS stimulated THP-1 monocytic cells.

To further assess the relevance of the above findings, TNF production by LPS-treated human peripheral blood mononuclear cells (PBMCs) was assessed in the presence of anti-MIF ISVDs. Again, ISVD E5 and ISVD E10 potently attenuated TNF production by LPS-stimulated PBMCs (FIG. 1B).

Notably, as shown in FIG. 1E, both ISVD E5 and ISVD E10 reduced TNF secretion by LPS-stimulated PEMs from WT mice to the levels seen with Mif$^{-/-}$ PEMs, illustrating a nearly complete block of MIF activity by these ISVDs.

Next, we assessed the potential of the anti-MIF ISVDs to interfere with MIF's tautomerase activity whose inhibition was shown to impact its inflammatory activity (23). ISVD E5 and ISVD E10, as well as ISVD H9, significantly reduced MIF's tautomerase activity (FIG. 1D). This is surprising, as it was reported in (20) that none of the MIF binding agents that bind to the epitopic region between AA50-68 were able to block tautomerase activity.

Interestingly, the Nanobodies inhibited MIF's tautomerase activity at a lower concentration than ISO-1 (0.67 µM versus 10 µM, respectively). This is surprising, as ISO-1 is documented to be a potent inhibitor of MIF's tautomerase activity (23). Although ISVD H9 inhibited MIF's tautomerase activity (FIG. 1D), it had no anti-inflammatory activity in vitro (FIG. 1C).

Finally, based on the observation that MIF is able to sustain inflammation in the presence of glucocorticoids (36), the representative MIF blocking ISVDs ISVD E5 and ISVD E10 were tested for their ability to override the MIF blocking effects following treatment of LPS stimulated macrophages with dexamethasone (37). As shown in FIG. 2, ISVD E5 and ISVD E10 further decreased TNF production following LPS stimulation in the presence of dexamethasone as compared to LPS-exposed cells treated with dexamethasone in the presence of an irrelevant ISVD.

Collectively, the results indicate that the MIF binders of the invention (as represented by members of different families: ISVD E5 and ISVD E10) were able to block MIF's pro-inflammatory activity in vitro.

Example 4 Multivalent Half-Life Extended ISVD E10 Constructs Inhibit LPS-Mediated TNF Induction In Vitro MIF was identified as a key pro-inflammatory cytokine in an acute disease setting, such as severe sepsis/endotoxic shock. However, MIF also exerts its effects in chronic diseases such as IBD or RA. In a chronic disease condition prolonged residence of the medicament in the patient seems favourable.

Since ISVDs exhibit a short serum half-life, which might affect their neutralizing potential in chronic in vivo settings, half-life extended ISVDs were generated. Moreover, multivalent constructs were generated in order to assess avidity effects. Given that it is unknown whether the formulation of such multivalent and half-life extended anti-MIF constructs affects their in vitro/in vivo functionality, we generated different formats of multivalent as well as serum half-life extended constructs of the exemplary ISVD E10, using a previously reported anti-serum albumin ISVD (Alb8) (41) for in vitro and in vivo studies. These constructs included monovalent E10 (SEQ ID NO: 1), E10-Alb8, E10-E10, E10-Alb8-E10 and E10-E10-Alb8 (SEQ ID NOs: 119-122). In first instance, the different ISVD E10 constructs were purified and assessed for their binding capacity to rmMIF in ELISA (data not shown) and via Surface Plasmon Resonance (Table 4). Linking ISVD Alb8 to ISVD E10 (via a flexible 9GS linker) did not affect the affinity for MIF, compared to ISVD E10 alone. However, both the bivalent ISVD E10 (E10-E10) and the half-life extended bivalent ISVD E10 constructs, regardless of the orientation (i.e. E10-Alb8-E10 or E10-E10-Alb8), exhibited increased apparent affinity for MIF (probably due to avidity). Next, we assessed the potential of the different ISVD E10 constructs to reduce the MIF-induced TNF production following stimulation of primary peritoneal macrophages with LPS. As shown in FIG. 3, all of the ISVD E10 constructs were capable of significantly decreasing TNF production following LPS stimulation in vitro. These results illustrate that the linkage to Alb8 had no effect on the ISVD MIF-inhibitory capacity of the MIF binders. Surprisingly, in this in vitro background all constructs comprising an HLE-binder were more potent than constructs without such an HLE-binding moiety. Avidity effects of constructs comprising two E10 clones appeared less relevant than the effects of the HLE-moiety.

Collectively, monovalent, multivalent and half-life extended MIF binders as represented by the exemplary anti-MIF ISVD E10 clone, were able to efficiently and significantly block MIF-mediated TNF induction by macrophages following stimulation with LPS in vitro.

Example 5 Multivalent Half-Life Extended ISVD E10 is Protective in a Mouse Model of Endotoxemia To assess the in vivo MIF-neutralizing potential of the anti-MIF ISVD E10 constructs we conducted endotoxic shock experiments as an experimental model of sepsis (42). To this end, the different anti-MIF ISVD E10 constructs (25 mg/kg) were co-injected i.p. with a lethal dose of LPS (12.5 mg/kg) and survival was monitored.

As shown in FIG. 4A, at the doses used, the MIF binders E10-Alb8-E10 and E10-E10-Alb8 were able to significantly rescue LPS-treated mice in this assay. In this case, i.e. without any further parameter optimization, the MIF binder E10-Alb8-E10 construct was the most efficient, which was subsequently selected for further experiments. Notably, the results of the in vitro TNF release experiments appear not to be directly translatable to an in vivo setting.

In first instance, we assessed the minimal E10-Alb8-E10 concentration able to rescue mice from endotoxic shock. To this end, a serial dilution of E10-Alb8-E10 (25 mg/kg, 12.5 mg/kg, 6.25 mg/kg and 2.5 mg/kg) was co-injected along with the LPS (12.5 mg/kg). As shown in FIG. 4B, the protective capacity of the MIF binders is concentration dependent, wherein the minimal concentration providing a protective effect of the exemplary MIF binder ISVD E10-Alb8-E10 construct should be more than 12.5 mg/kg. Blocking MIF using the exemplary MIF binder E10-Alb8-E10 also reduced peak serum TNF levels in this in vivo model (FIG. 6).

Next, we assessed whether the MIF binders of the invention could be used therapeutically, i.e. as a treatment, when administered at the moment when symptoms of morbidity are observed (6 hours post LPS injection). As indicated in FIG. 5, the exemplary MIF binder E10-Alb8-E10 was able to significantly prolong the survival time.

Collectively, the results show that treatment of mice injected with a lethal dose of endotoxin using a MIF binder was found to rescue 40-50% of the mice from lethality when given prophylactically and to delay lethality when given therapeutically.

Example 6 Discussion

MIF has been identified as an upstream regulator of innate immunity (4) and is considered an attractive target to alleviate metabolic, systemic, autoimmune, and inflammation-associated disorders (23, 3, 35). Consequently, strategies to inhibit MIF's deleterious effects might have therapeutic potential and could be administered by a precision medicine approach in subjects who are genotypic high MIF expressers (47).

Single-domain antigen-binding fragments (ISVDs) as a novel tool to antagonize MIF's inflammatory effects. Eleven ISVDs were identified and found to bind to both recombinant mouse and human MIF with nM affinities. This cross-reactivity is likely due to the high sequence and structural similarity between mouse and human MIF (48, 5). The nM "apparent" affinities of the half-life extended anti-MIF ISVDs are within the range of the interaction $K_D$ reported for MIF and CD74 (1.5-9 nM) (45). Although the ISVDs were not sequence optimized, all anti-MIF ISVDs, with the exception of ISVD F10 and ISVD H5, exhibited good thermal stability, which is an important functional indicator for the use of antibodies and antibody-fragments in medicine and the in vivo activity of antibodies (30, 31). Increasing stability of ISVD F10 and ISVD H5 can be accomplished by routine sequence optimization procedures.

Importantly, some of these ISVDs have the ability to i) potently inhibit endotoxin (LPS)-induced TNF production by human monocytes and murine macrophages, and ii) inhibit MIF's tautomerase activity. In an effort to further rationalize the obtained results, we displayed the outcome of the epitope mapping experiments on the crystal structure of the MIF trimer (not shown). ISVD H9, ISVD E5, and ISVD E10 are able to block MIF's tautomerase activity, indicating that they bind within or close to MIF's site of interaction with CD74 (14). Indeed, it can be observed that the epitopes of these ISVDs on the MIF surface overlap with the site responsible for tautomerase activity. Notably, ISVD E5 and ISVD E10 inhibited MIF's tautomerase activity at a lower concentration than ISO-1 (0.67 μm versus 10 μM, respectively), i.e. the most well-described MIF antagonist (49). Tarasuk et al. (21) document that a fully human single-chain Fv (HuScFv) directed against MIF also blocks MIF's tautomerase activity, but these authors did not test the potential for this ScFv construct to block MIF's biological inflammatory effects. Compared to ScFv, Nbs have the further advantage of being more soluble and stable (Riechmann and Muyldermans (1999) J. Immunol. Methods 231: 25-38).

MIF binding to CD74 leads to i) the activation of the ETS/AP1 family of transcription factors which is important for the expression of TLR4, an integral component of the LPS receptor complex (4), and ii) the expression of cell adhesion molecules and inflammatory cytokines such as TNF (4, 34, 35). Additionally, MIF was shown to counteract the immunosuppressive action of glucocorticoids, thereby prolonging inflammatory responses (36). Using a murine macrophage cell line (RAW264.7) it was shown that the exemplary ISVDs E5 and E10 significantly reduced TNF production following LPS stimulation in vitro in the presence and absence of the glucocorticoid dexamethasone. Notably, ISVD E5 and ISVD E10 appear to be more efficient at inhibiting TNF induction (50% TNF reduction at a concentration of 0.5-1.67 μM) than ISO-1 (50% TNF reduction at 10 μM (23)). Thus, the exemplary ISVDs E5 and E10 can efficiently reduce MIF's tautomerase function, counter MIF's role in LPS-induced TNF production and block MIF's glucocorticoid overriding effects. Remarkably, although ISVD H9 also inhibited MIF's tautomerase activity (FIG. 1B), it had no anti-inflammatory activity in vitro (FIG. 1A). The reason for this is unclear.

A comparison of the regions recognized by ISVD E5 and ISVD E10 (Pro35-Gly66) with the putative CD74 binding site (50) reveals a strong overlap between both regions, explaining the inhibitory property of these ISVDs To assess the protective effects of the exemplary ISVD E10 in an in vivo model of endotoxic shock, bivalent and trivalent half-life extended constructs were engineered using an anti-albumin ISVD (51-53), in order to increase avidity affects or serum half-life for maximal in vivo potential. All ISVD E10 constructs were shown to efficiently reduce TNF production by LPS stimulated macrophages as compared to the monovalent ISVD E10, whereby the ISVD E10-ISVD Alb8-ISVD E10 construct was found to be the most potent. When given prophylactically in vivo, this construct also appeared to be more efficacious than the ISVD E10-ISVD E10-ISVD Alb8 construct rescuing 60% versus 40% of the mice receiving a lethal LPS dose, whereby mice recovered completely from the insult 72 hours post-injection. The potency difference between both constructs in vitro and in vivo suggests that the position of the anti-albumin ISVD Alb8 in the construct may be of relevance. Without being bound to any theory, a possible explanation for this might be that the ISVD E10-ISVD Alb8-ISVD E10 construct can bind two regions within a MIF-trimer or bind two trimers simultaneously, while for the ISVD E10-ISVD E10-ISVD Alb8 construct this ability could be impaired due to the close proximity of the two ISVD E10 molecules. In addition, or in concert with the previous hypothesis, the binding of the ISVD Alb8 to albumin might cause more hindrance in the ISVD E10-ISVD E10-ISVD Alb8 compared to the ISVD E10-ISVD Alb8-ISVD E10 construct. In general, longer linkers, e.g. 35GS instead of 9GS, circumvent this problem. These results further show that, in addition to half-life extension via albumin binding, bivalent MIF binding has better in vivo blocking potential. Indeed, tailoring of the monovalent ISVD E10 into a ISVD E10-ISVD Alb8-ISVD E10 construct allows also more potent blocking of LPS-mediated endotoxemia than ISO-1. While the ISVD E10-ISVD Alb8-ISVD E10 construct can be administered as a single shot of 12.5-25 mg/kg, ISO-1 has to be given in multiple consecutive injections and at high doses of 35 mg/kg in order to prevent LPS-mediated lethality (23, 35). Moreover, since the affinity of the ISVD Alb8 for mouse serum albumin is suboptimal (compared to its human serum albumin binding properties) (27), the current construct may underestimate the potential of this approach. Importantly, the E10-Alb8-E10 construct was found to delay LPS-mediated lethality even when administered 6 hours post LPS injection. Eventually the mice still succumbed, suggesting that either (i) a higher dose or multiple/continuous injections of the construct might be required or (ii) only blocking of MIF at the early stages of the insult is crucial in this setting. Regarding the latter possibility, it was shown by Chagnon et al. (54) that inhibition of MIF early in a rat endotoxic shock model partially reverses the imbalance of pro-apoptotic to pro-survival pathways, thereby reducing acute inflammation and myocardial dysfunction induced by endotoxin. This was already observed within 6 hours post LPS/anti-MIF administration and hence infers that an early blockade of MIF is crucial.

While several small molecule inhibitors of MIF's biologic activity have been documented (49, 55, 56), this is the first report to establish that a MIF antagonist, when appropriately engineered, can prevent lethal endotoxemia when administered as a single injection. Although monoclonal/polyclonal anti-MIF antibodies were also found to exert some protective effects (20, 22, 57), ISVDs have the advantage that they can be tailored into multifunctional formats as demonstrated herein. In contrast to conventional antibodies, ISVDs lack an Fc portion which avoids further inflammatory reactions (58).

Tables

TABLE 4

Ligand affinity of anti-MIF constructs to mouse MIF. (For E10-E10, E10-Alb8-E10 and E10-E10-Alb8 the reported affinity constants should be seen as apparent KD values.)

| Family | Name | Kon ($10^5 M^{-1} s^{-1}$) | Koff ($10^3 s^{-1}$) | KD (nM) |
|---|---|---|---|---|
| I | B5 | 1.42 | 5.42 | 38.17 |
| II | C10 | 1.63 | 2.53 | 15.52 |
| III | A2 | 1.43 | 2.00 | 13.98 |
| III | D2 | 1.51 | 1.89 | 12.52 |
| III | D4 | 0.99 | 2.74 | 27.73 |
| III | F10 | 0.19 | 4.34 | 228.42 |
| IV | H5 | 1.16 | 2.97 | 25.6 |
| V | E5 | 1.63 | 1.91 | 11.72 |
| V | H9 | 0.70 | 2.31 | 33.00 |
| VI | D12 | 0.59 | 5.11 | 85.88 |
| VII | E10 | 0.86 | 4.57 | 53.13 |
| Multivalent E10 Constructs | | | | |
| | E10-Alb8 | 0.64 | 5.65 | 88.28 |
| | E10-E10 | 3.51 | 1.12 | 3.19 |
| | E10-E10-Alb8 | 3.22 | 3.24 | 10.06 |
| | E10-Alb8-E10 | 4.17 | 2.51 | 6.02 |

TABLE 5

Ligand affinity of anti-MIF ISVDs to human MIF.

| Family | Name | Kon ($10^5 M^{-1} s^{-1}$) | Koff ($10^3 s^{-1}$) | KD (nM) |
|---|---|---|---|---|
| I | B5 | 0.41 | 1.54 | 37.75 |
| II | C10 | 0.38 | 1.61 | 41.19 |
| III | A2 | 3.11 | 0.92 | 2.96 |
| III | D2 | 0.75 | 1.24 | 16.50 |
| III | D4 | 0.44 | 1.53 | 35.00 |
| III | F10 | ND | ND | ND |
| IV | H5 | 0.17 | 0.48 | 27.50 |
| V | E5 | 0.78 | 0.74 | 9.41 |
| V | H9 | 0.32 | 2.57 | 80.30 |
| VI | D12 | 0.18 | 2.98 | 166.00 |
| VII | E10 | 0.98 | 6.32 | 64.50 |

TABLE 6

Thermostability of anti-MIF ISVDs.

| Family | Name | Tm (° C.) |
|---|---|---|
| I | B5 | 68.51 |
| II | C10 | 61.42 |
| III | A2 | 72.16 |
| III | D2 | 60.81 |
| III | D4 | 69.19 |
| III | F10 | 47.46 |
| IV | H5 | 49.34 |
| V | E5 | 66.74 |
| V | H9 | 61.32 |
| VI | D12 | 72.82 |
| VII | E10 | 65.81 |

TABLE 7

Amino acid sequences of monovalent anti-MIF ISVDs
("ID" refers to the SEQ ID NO as used herein)

| Name | ID | Amino acid sequence |
|---|---|---|
| E10 | 1 | EVQLVESGGGSVQAGDSLRLSCAASGRTLSNSIMGWFRQAPGKEREFVANINWSGTSRLYADSVKGRFTISRDNTKSTVYLQMNSLKPEDTAIYYCAARSSTMSATDYWGQGTQVTVSS |
| D12 | 2 | EVQLVESGGGLVQAGGSLRLSCAASGRTISSYIVGWFRQAPGKEREFVANIGWSGSMPLYADSVKGRFTIFRDNAKNTVYLEMNKLKPEDTAVYYCAARGAGQLTNDYWGQGTQVTVSS |
| E5 | 3 | EVQLVESGGGLVHAGGSLRLSCAASGRTFSSYFMGWFRQAPGKAREFVANINFSGGTTVYASSVKGRFTISRDNSKNTVYLQMNSVKPEDTAVYYCVARGLTQDYDYWGQGTQVTVSS |
| H9 | 4 | EVQLVESGGGLVHAGGSLRLSCAASGRTSSTYFMGWFRQAPGKAREFVANINFSGGTTVYASSVKGRFTISRDNSKNTVYLQLNSVKPEDTAVYYCSARGLNQEYDFWGQGTQVTVSS |
| H5 | 5 | EVQLVESGGGLVQPGGSLRLSCVASGFTFRTYAMSWVRQAPGKGSEWVSTINNGGGVTGYADSVEGRFTISRDNAKNTLYLQMNSLKPEDTAVYYCAKGTSRGQGTQVTVSS |
| A2 | 6 | EVQLVESGGGLVQDGGSLRLSCAASGRTASIQVMGWFRQAPGKEREFVGNIGWNYGLTLYADPVKGRFTISRDNAKNTVYLQMNNLKPEDTAVYYCAARIGTITYDYWGQGTQVTVSS |
| D2 | 7 | EVQLVESGGGLVQDGGSLRLSCAASGRTASIHTMGWFRQAPGQERGFVGNIGWNYGLTLYADSVKGRFTISRDNAKNTVYLQMNNLKPEDTAVYYCAARIGTTPYDYWGQGTQVTVSS |
| D4 | 8 | KVQLVESGGGLVQDGGSLRLSCAASGRTASIQVMGWFRQAPGKEREFVGNIGWNYGLTLYPDSVKGRFTISRDNAKNTVYLQMNNLKPEDTAVYYCAARIGTTTYDYWGQGTQVTVSS |
| F10 | 9 | EVQLVESGGGLVQDGGSLRLSCAASGRTASIQVMGWFRQAPGKEREFVGNIGWNYGLTLYPDSVKGRFTISRGNAKNAVYLQMNNLKPEDTAVYYCAARIGTTTYDYWGQGTQVTVSS |
| C10 | 10 | EVQLVESGGGLVQAGGSLRLSCAASGRTSSIVAIGWFRQAPGKEREFVSNIGWKFGSTVYVDSVKGRFTISKDNAKNTVYLQMNSLKPEDTAVYRCAARSDGRVYDSWGQGTQVTVSS |
| B5 | 11 | EVQLVESGGGLVQAGGSLRLSCAASGRSFSNYIMGWFRQAPGKEREFVANISWNYGTTFYADSVKGRFTISGDSAKNTVYLQMTSLKPEDTAVYYCAARPVRGGRNFDYWGQGTQVTVSS |

TABLE 8

Sequences for CDRs and frameworks, plus preferred combinations as
provided in formula I, namely FR1-CDR1-FR2-CDR2-FR3-CDR3-FR4
(the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | E10 | 12 | EVQLVESGGGSVQAGDSLRLSCAAS | 23 | GRTLSNSI | 34 | MGWFRQAPGKEREFVAN | 45 | INWSGTSR | 56 | LYADSVKGRFTISRDNTKSTVYLQMNSLKPEDTAIYYC | 67 | AARSSTMSATDY | 78 | WGQGTQVTVSS |
| 2 | D12 | 13 | EVQLVESGGGLVQAGGSLRLSCAAS | 24 | GRTISSYI | 35 | VGWFRQAPGKEREFVAN | 46 | IGWSGSMP | 57 | LYADSVKGRFTIFRDNAKNTVYLEMNKLKPEDTAVYYC | 68 | AARGAGQLTNDY | 79 | WGQGTQVTVSS |
| 3 | E5 | 14 | EVQLVESGGGLVHAGGSLRLSCAAS | 25 | GRTFSSYF | 36 | MGWFRQAPGKAREFVAN | 47 | INFSGGTT | 58 | VYASSVKGRFTISRDNSKNTVYLQMNSVKPEDTAVYYC | 69 | VARGLTQDYDY | 80 | WGQGTQVTVSS |
| 4 | H9 | 15 | EVQLVESGGGLVHAGGSLRLSCAAS | 26 | GRTSSTYF | 37 | MGWFRQAPGKAREFVAN | 48 | INFSGGTT | 59 | VYASSVKGRFTISRDNSKNTVYLQLNSVKPEDTAVYYC | 70 | SARGLNQEYDF | 81 | WGQGTQVTVSS |
| 5 | H5 | 16 | EVQLVESGGGLVQPGGSLRLSCVAS | 27 | GFTFRTYA | 38 | MSWVRQAPGKGSEWVST | 49 | INNGGGVT | 60 | GYADSVEGRFTISRDNAKNTLYLQMNSLKPEDTAVYYC | 71 | AKGTS | 82 | RGQGTQVTVSS |
| 6 | A2 | 17 | EVQLVESGGGLVQDGGSLRLSCAAS | 28 | GRTASIQV | 39 | MGWFRQAPGKEREFVGN | 50 | IGWNYGLT | 61 | LYADPVKGRFTISRDNAKNTVYLQMNNLKPEDTAVYYC | 72 | AARIGTITYDY | 83 | WGQGTQVTVSS |
| 7 | D2 | 18 | EVQLVESGGGLVQDGGSLRLSCAAS | 29 | GRTASTHT | 40 | MGWFRQAPGQERGFVGN | 51 | IGWNYGLT | 62 | LYADSVKGRFTISRDNAKNTVYLQMNNLKPEDTAVYYC | 73 | AARIGTTPYDY | 84 | WGQGTQVTVSS |
| 8 | D4 | 19 | KVQLVESGGGLVQDGGSLRLSCAAS | 30 | GRTASIQV | 41 | MGWFRQAPGKEREFVGN | 52 | IGWNYGLT | 63 | LYPDSVKGRFTISRDNAKNTVYLQMNNLKPEDTAVYYC | 74 | AARIGTTTYDY | 85 | WGQGTQVTVSS |
| 9 | F10 | 20 | EVQLVESGGGLVQDGGSLRLSCAAS | 31 | GRTASIQV | 42 | MGWFRQAPGKEREFVGN | 53 | IGWNYGLT | 64 | LYPDSVKGRFTISRGNAKNAVYLQMNNLKPEDTAVYYC | 75 | AARIGTTTYDY | 86 | WGQGTQVTVSS |
| 10 | C10 | 21 | EVQLVESGGGLVQAGGSLRLSCAAS | 32 | GRTSSIVA | 43 | IGWFRQAPGKEREFVSN | 54 | IGWKFGST | 65 | VYVDSVKGRFTISKDNAKNTVYLQMNSLKPEDTAVYRC | 76 | AARSDGRVYDS | 87 | WGQGTQVTVSS |

TABLE 8-continued

Sequences for CDRs and frameworks, plus preferred combinations as
provided in formula I, namely FR1-CDR1-FR2-CDR2-FR3-CDR3-FR4
(the following terms: "ID" refers to the given SEQ ID NO)

| ID | Nano-body | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 11 | B5 | 22 | EVQLVESGGGLVQ AGGSLRLSCAAS | 33 | GRSF SNYI | 44 | MGWFRQAPGK EREFVAN | 55 | ISWN YGTT | 66 | FYADSVKGRFTISGDSAKNT VYLQMTSLKPEDTAVYYC | 77 | AARPVRG GRNFDY | 88 | WGQGTQV TVSS |

TABLE 9

Amino acid sequences of selected multivalent anti-MIF constructs

| Name | ID | Amino acid sequence |
|---|---|---|
| E10-Alb | 119 | EVQLVESGGGSVQAGDSLRLSCAASGRTLSNSIMGWFRQAPGKEREFVANINWSGT SRLYADSVKGRFTISRDNTKSTVYLQMNSLKPEDTAIYYCAARSSTMSATDYWGQG TQVTVSSGGGGSGGGSEVQLVESGGGLVQPGNSLRLSCAASGFTFSSFGMSWVRQA PGKGLEWVSSISGSGSDTLYADSVKGRFTISRDNAKTTLYLQMNSLRPEDTAVYYC TIGGSLSRSSQGTLVTVSS |
| E10-E10 | 120 | EVQLVESGGGSVQAGDSLRLSCAASGRTLSNSIMGWFRQAPGKEREFVANINWSGT SRLYADSVKGRFTISRDNTKSTVYLQMNSLKPEDTAIYYCAARSSTMSATDYWGQG TQVTVSSGGGGSGGGSEVQLVESGGGSVQAGDSLRLSCAASGRTLSNSIMGWFRQA PGKEREFVANINWSGTSRLYADSVKGRFTISRDNTKSTVYLQMNSLKPEDTAIYYC AARSSTMSATDYWGQGTQVTVSS |
| E10-Alb-E10 | 121 | EVQLVESGGGSVQAGDSLRLSCAASGRTLSNSIMGWFRQAPGKEREFVANINWSGT SRLYADSVKGRFTISRDNTKSTVYLQMNSLKPEDTAIYYCAARSSTMSATDYWGQG TQVTVSSGGGGSGGGSEVQLVESGGGLVQPGNSLRLSCAASGFTFSSFGMSWVRQA PGKGLEWVSSISGSGSDTLYADSVKGRFTISRDNAKTTLYLQMNSLRPEDTAVYYC TIGGSLSRSSQGTLVTVSSGGGGSGGGSEVQLVESGGGSVQAGDSLRLSCAASGRT LSNSIMGWFRQAPGKEREFVANINWSGTSRLYADSVKGRFTISRDNTKSTVYLQMN SLKPEDTAIYYCAARSSTMSATDYWGQGTQVTVSS |
| E10-E10-Alb | 122 | EVQLVESGGGSVQAGDSLRLSCAASGRTLSNSIMGWFRQAPGKEREFVANINWSGT SRLYADSVKGRFTISRDNTKSTVYLQMNSLKPEDTAIYYCAARSSTMSATDYWGQG TQVTVSSGGGGSGGGSEVQLVESGGGSVQAGDSLRLSCAASGRTLSNSIMGWFRQA PGKEREFVANINWSGTSRLYADSVKGRFTISRDNTKSTVYLQMNSLKPEDTAIYYC AARSSTMSATDYWGQGTQVTVSSGGGGSGGGSEVQLVESGGGLVQPGNSLRLSCAA SGFTFSSFGMSWVRQAPGKGLEWVSSISGSGSDTLYADSVKGRFTISRDNAKTTLY LQMNSLRPEDTAVYYCTIGGSLSRSSQGTLVTVSS |

TABLE 10

MIF sequences from various species
("ID" refers to the SEQ ID NO as used herein)

| Name | ID | Amino acid sequence |
|---|---|---|
| human MIF P14174-1 | 89 | MPMFIVNTNVPRASVPDGFLSELTQQLAQATGKPQYIAV HVVPDQLMAFGGSSEPCALCSLHSIGKGGAQNRSYSKL LCGLLAERLRISPDRVYINYYDMNAANVGWNNSTFA |
| Rhesus MIF Q6DN04-1 | 90 | MPMFIVNTNVPRASVPDGFLSELTQQLAQATGKPPQYIA VHVVPDQLMAFGGSSEPCALCSLHSIGKIGGAQNRSYSK LLCGLLAERLRISPDRVYINYYDMNAANVGWNNSTFA |
| Mouse MIF P34884-1 | 91 | MPMFIVNTNVPRASVPEGFLSELTQQLAQATGKPAQYIA VHVVPDQLMTFSGTNDPCALCSLHSIGKIGGAQNRNYSK LLCGLLSDRLHISDRVYINYYDMNAANVGWNGSTFA |

TABLE 11

Serum albumin binding ISVD sequences ("ID" refers to the SEQ ID NO as used herein)

| Name | ID | Amino acid sequence |
|---|---|---|
| Alb8 | 103 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb23 | 104 | EVQLLESGGGLVQPGGSLRLSCAASGFTFRSFGMSWVRQAPGKGPEWVSSISGSGSDTLYADS VKGRFTISRDNSKNTLYLQMNSLRPEDTAVYYCTIGGSLSRSSQGTLVTVSS |

TABLE 11 -continued

Serum albumin binding ISVD sequences ("ID" refers to the SEQ ID NO as used herein)

| Name | ID | Amino acid sequence |
|---|---|---|
| Alb129 | 105 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTATYYCTIGGSLSRSSQGTLVTVSSA |
| Alb132 | 106 | EVQLVESGGGVVQPGGSLRLSCAASGFTFRSFGMSWVRQAPGKGPEWVSSISGSGSDTLYADS<br>VKGRFTISRDNSKNTLYLQMNSLRPEDTATYYCTIGGSLSRSSQGTLVTVSSA |
| Alb11 | 107 | EVQLVESGGGLVQPGNSLRLSCAASGFTFSSFGMSWVRQAPGKGLEWVSSISGSGSDTLYADS<br>VKGRFTISRDNAKTTLYLQMNSLRPEDTAVYYCTIGGSLSRSSQGTLVTVSS |
| Alb11 (S112K)-A | 108 | EVQLVESGGGLVQPGNSLRLSCAASGFTFSSFGMSWVRQAPGKGLEWVSSISGSGSDTLYADS<br>VKGRFTISRDNAKTTLYLQMNSLRPEDTAVYYCTIGGSLSRSSQGTLVKVSSA |
| Alb82 | 109 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSS |
| Alb82-A | 110 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSA |
| Alb82-AA | 111 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSAA |
| Alb82-AAA | 112 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSAAA |
| Alb82-G | 113 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSG |
| Alb82-GG | 114 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSGG |
| Alb82-GGG | 115 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSGGG |
| Alb92 | 123 | EVQLVESGGGVVQPGGSLRLSCAASGFTFRSFGMSWVRQAPGKGPEWVSSISGSGSDTLYADS<br>VKGRFTISRDNSKNTLYLQMNSLRPEDTALYYCTIGGSLSRSSQGTLVTVSS |
| Alb223 | 124 | EVQLVESGGGVVQPGGSLRLSCAASGFTFRSFGMSWVRQAPGKGPEWVSSISGSGSDTLYADS<br>VKGRFTISRDNSKNTLYLQMNSLRPEDTALYYCTIGGSLSRSSQGTLVTVSSA |

TABLE 12

Linker sequences ("ID" refers to the SEQ ID NO as used herein)

| Name | ID | Amino acid sequence |
|---|---|---|
| 3A linker (Poly-A) | 102 | AAA |
| 5GS linker | 92 | GGGGS |
| 7GS linker | 93 | SGGSGGS |
| 8GS linker | 125 | GGGGCGGGS |
| 9GS linker | 94 | GGGGSGGGS |
| 10GS linker | 95 | GGGGSGGGGS |
| 15GS linker | 96 | GGGGSGGGGSGGGGS |
| 18GS linker | 97 | GGGGSGGGGSGGGGGGS |
| 20GS linker | 98 | GGGGSGGGGSGGGGSGGGGS |
| 25GS linker | 99 | GGGGSGGGGSGGGGSGGGGSGGGGS |
| 30GS linker | 100 | GGGGSGGGGSGGGGSGGGGSGGGGSGGGGS |
| 35GS linker | 101 | GGGGSGGGGSGGGGSGGGGSGGGGSGGGGSGGGGS |
| 40GS linker | 126 | GGGGSGGGGSGGGGSGGGGSGGGGSGGGGSGGGGSGGGGS |
| G1 hinge | 127 | EPKSCDKTHTCPPCP |
| 9GS-G1 hinge | 128 | GGGGSGGGSEPKSCDKTHTCPPCP |
| Llama upper long hinge region | 129 | EPKTPKPQPAAA |
| G3 hinge | 130 | ELKTPLGDTTHTCPRCPEPKSCDTPPPCPRC<br>PPEPKSCDTPPPCPRCPEPKSCDTPPPCPRCP |

REFERENCES

1. Beishuizen et al., (2001). Macrophage Migration Inhibitory Factor and Hypothalamo-Pituitary-Adrenal Function during Critical Illness. J Clin Endocrinol Metab 86: 2811-2816.
2. Bozza et al. (2004). Macrophage migration inhibitory factor levels correlate with fatal outcome in sepsis. Shock 22(4):309-13.

3. Flaster et al. (2007). The macrophage migration inhibitory factor-glucocorticoid dyad: regulation of inflammation and immunity. Mol Endocrinol 21(6):1267-1280.
4. Calandra & Roger (2003). Macrophage migration inhibitory factor: a regulator of innate immunity. Nat Rev Immunol 3:791-800.
5. Sun et al. (1996). Crystal structure at 2.6-A resolution of human macrophage migration inhibitory factor. Proc Natl Acad Sci USA 93(11):5191-6.
6. Mischke et al., (1998). Cross-linking and mutational analysis of the oligomerization state of the cytokine macrophage migration inhibitory factor (MIF). FEBS Lett 427:85-90.
7. Philo et al. (2004). Re-examining the oligomerization state of macrophage migration inhibitory factor (MIF) in solution. Biophys Chem 108:77-87.
8. Ouertatani-Sakouhi et al. (2010). Identification and characterization of novel classes of macrophage migration inhibitory factor (MIF) inhibitors with distinct mechanisms of action. J Biol Chem 285:26581-98.
9. Weber et al. (2008). Structural determinants of MIF functions in CXCR2-mediated inflammatory and atherogenic leukocyte recruitment. Proc Natl Acad Sci USA 105(42):16278-83.
10. Kleemann, et al. (1998) Disulfide analysis reveals a role for macrophage migration inhibitory factor (MIF) as thiol-protein oxidoreductase J. Mol. Biol. 280:85-102.
11. Rosengren et al. (1996) The immunoregulatory mediator macrophage migration inhibitory factor (MIF) catalyzes a tautomerization reaction. Mol Med 2(1):143-9.
12. Gregory et al. (2006). Macrophage migration inhibitory factor induces macrophage recruitment via CC chemokine ligand 2. J Immunol. 2006 Dec. 1; 177(11):8072-9.
13. Rosengren et al. (1997) The macrophage migration inhibitory factor MIF is a phenylpyruvate tautomerase. FEBS Lett 417(1):85-88.
14. Fingerle-Rowson et al. (2009) A tautomerase-null macrophage migration-inhibitory factor (MIF) gene knock-in mouse model reveals that protein interactions and not enzymatic activity mediate MIF-dependent growth regulation. Mol Cell Biol 29(7):1922-32.
15. David (1966). Delayed hypersensitivity in vitro: its mediation by cell-free substances formed by lymphoid cell-antigen interaction. Proc Natl Acad Sci U.S.A 56: 72-77.
16. Lubetsky et al. (2002). The tautomerase active site of macrophage migration inhibitory factor is a potential target for discovery of novel anti-inflammatory agents. J Biol Chem 277: 24976-82.
17. Cross et al. (2009). Nutrient isothiocyanates covalently modify and inhibit the inflammatory cytokine macrophage migration inhibitory factor (MIF). Biochem J 423: 315-21.
18. Stosic-Grujicic et al. (2009). MIF in autoimmunity and novel therapeutic approaches. Autoimmun. Rev 8:244-249.
19. Greven et al. (2010). Autoimmune diseases: MIF as a therapeutic target. Expert Opin. Ther. Targets 14:253-264.
20. Calandra et al. (2000). Protection from septic shock by neutralization of macrophage migration inhibitory factor. Nat Med 6:164-70.
21. Tarasuk M, et al. (2014). Human single-chain variable fragment antibody inhibits macrophage migration inhibitory factor tautomerase activity. Int J Mol Med 33(3):515-22.
22. Kerschbaumer et al. (2012). Neutralization of macrophage migration inhibitory factor (MIF) by fully human antibodies correlates with their specificity for the β-sheet structure of MIF. J Biol Chem 287:7446-55.
23. Al-Abed et al. (2005). ISO-1 binding to the tautomerase active site of MIF inhibits its pro-inflammatory activity and increases survival in severe sepsis. J Biol Chem 280:36541-4.
24. Conroy et al. (2010). Inflammation and cancer: macrophage migration inhibitory factor (MIF)—the potential missing link. QJM 103:831-836
25. Saerens et al. (2004). Single domain antibodies derived from dromedary lymph node and peripheral blood lymphocytes sensing conformational variants of prostate-specific antigen. J Biol Chem 279:51965-72.
26. Conrath et al. (2001). β-Lactamase inhibitors derived from single-domain antibody fragments elicited in the Camelidae. Antimicrob Agents Chemother 45:2807-2812.
27. Karlsson et al. (2006) Analyzing a kinetic titration series using affinity biosensors. Anal Biochem 349:136-47.
28. Caljon et al. (2012). Affinity is an important determinant of the anti-trypanosome activity of nanobodies. PLoS Negl Trop Dis 6(11):e1902.
29. Dios et al. (2002). Inhibition of MIF bioactivity by rational design of pharmacological inhibitors of MIF tautomerase activity. J Med Chem 45:2410-6.
30. Orr et al. (2003). Rapid method for measuring ScFv thermal stability by yeast surface display. Biotechnol Prog 19:631-8.
31. Wörn & Plückthun (2001). Stability engineering of antibody single-chain Fv fragments. J Mol Biol 305:989-1010.
32. O'Reilly et al. (2016). Targeting MIF in Cancer: Therapeutic Strategies, Current Developments, and Future Opportunities. Med Res Rev 36:440-60.
33. Calandra & Roger (2003). Macrophage migration inhibitory factor: a regulator of innate immunity. Nat Rev Immunol 3(October):791-800.
34. Bozza et al. (2012). Macrophage migration inhibitory factor in protozoan infections. J Parasitol Res 2012: 413052.
35. Morand et al. (2006). MIF: a new cytokine link between rheumatoid arthritis and atherosclerosis. Nat Rev Drug Discov 5:399-410.
36. Calandra et al. (1995). MIF as a glucocorticoid-induced modulator of cytokine production. Nature 377:68-71.
37. Piette et al. (2009). The dexamethasone-induced inhibition of proliferation, migration, and invasion in glioma cell lines is antagonized by macrophage migration inhibitory factor (MIF) and can be enhanced by specific MIF inhibitors. J Biol Chem 284:32483-92.
38. Zhang et al. (2004). Pentamerization of single-domain antibodies from phage libraries: a novel strategy for the rapid generation of high-avidity antibody reagents. J Mol Biol 335:49-56.
39. Coppieters et al. (2006). Formatted anti-tumor necrosis factor alpha VHH proteins derived from camelids show superior potency and targeting to inflamed joints in a murine model of collagen-induced arthritis. Arthritis Rheum 54:1856-66.
40. Vosjan et al. (2012). Nanobodies targeting the hepatocyte growth factor: potential new drugs for molecular cancer therapy. Mol Cancer Ther 11:1017-25.
41. Maussang et al. (2013) Llama-derived single variable domains (nanobodies) directed against chemokine receptor CXCR7 reduce head and neck cancer cell growth in vivo. J Biol Chem 288:29562-29572.
42. Le Roy et al. (1999). Monoclonal antibodies to murine lipopolysaccharide (LPS)-binding protein (LBP) protect mice from lethal endotoxemia by blocking either the binding of LPS to LBP or the presentation of LPS/LBP complexes to CD14. J Immunol 162:7454-60.
43. Martin et al. (2015). Phase I study of the anti-CD74 monoclonal antibody milatuzumab (hLL1) in patients with previously treated B-cell lymphomas. *Leuk Lymphoma* 56:3065-70. doi:10.3109/10428194.2015.1028052.
44. Flieger et al. (2003). Regulated secretion of macrophage migration inhibitory factor is mediated by a non-classical pathway involving an ABC transporter. *FEBS Lett* 551:78-86.
45. Leng et al. (2003) MIF signal transduction initiated by binding to CD74. *J Exp Med* 197:1467-76. doi: 10.1084/jem.20030286
46. Kudrin et al., (2006) Human macrophage migration inhibitory factor: a proven immuno-modulatory cytokine?*J Biol Chem* 281:29641-51. doi:10.1074/jbc.M601103200
47. Tilstam et al. (2017) MIF family cytokines in cardiovascular diseases and prospects for precision-based therapeutics. Expert Opin Ther Targets 21:671-683. doi: 10.1080/14728222. 2017.1336227
48. Pruitt et al. (2012) The Reference Sequence (RefSeq) Database.
49. Leng et al. (2011) A small-molecule macrophage migration inhibitory factor antagonist protects against glomerulonephritis in lupus-prone NZB/NZW F1 and MRL/lpr mice. *J Immunol* 186:527-538. doi:10.4049/jimmunol.1001767
50. Meza-Romero et al. (2016) Predicted structure of MIF/CD74 and RTL1000/CD74 complexes. *Metab Brain Dis* 31:249-255. doi:10.1007/s11011-016-9798-x
51. Harmsen et al. (2007) Properties, production, and applications of camelid single-domain antibody fragments. *Appl Microbiol Biotechnol* 77:13-22. doi:10.1007/s00253-007-1142-2
52. Van Bockstaele et al. (2009) The development of nanobodies for therapeutic applications. *Curr Opin Investig Drugs* 10:1212-24.
53. Hoefman et al. (2015) Pre-Clinical Intravenous Serum Pharmacokinetics of Albumin Binding and Non-Half-Life Extended Nanobodies®. *Antibodies* 4:141-156. doi: 10.3390/antib4030141
54. Chagnon et al. (2005) Endotoxin-induced myocardial dysfunction: effects of macrophage migration inhibitory factor neutralization. *Circ Res* 96:1095-102. doi:10.1161/01.RES. 0000168327. 22888.4d
55. Vujicic et al. (2014) Novel inhibitors of macrophage migration inhibitory factor prevent cytokine-induced beta cell death. *Eur J Pharmacol* 740:683-9. doi:10.1016/j.ejphar.2014.06.009
56. Tsai & Lin (2014) Virtual Screening of Some Active Human Macrophage Migration Inhibitory Factor Antagonists. *J Biomol Screen* 19:1116-23. doi:10.1177/1087057114523317
57. Zhang et al. (2011) Characterization, epitope identification and mechanisms of the anti-septic capacity of monoclonal antibodies against macrophage migration inhibitory factor. *Int Immunopharmacol* 11:1333-40. doi: 10.1016/j.intimp.2011.04.017
58. Vincke et al (2009) General strategy to humanize a camelid single-domain antibody and identification of a universal humanized nanobody scaffold. *J Biol Chem* 284:3273-3284. doi:10.1074/jbc.M806889200
59. Rajasekaran et al. (2016) Macrophage Migration Inhibitory Factor-CXCR4 Receptor Interactions: evidence for partial allosteric agonism in comparison with CXCL12 chemokine. *J Biol Chem.* 291:15881-95. doi: 10.1074/jbc.M116.717751. Epub 2016 May 19.
60. Bloom et al. (2016) MIF, a controversial cytokine: a review of structural features, challenges, and opportunities for drug development. *Expert Opin Ther Targets.* 20:1463-1475. Epub 2016 Nov. 1
61. Al-Abed & VanPatten (2011) MIF as a disease target: ISO-1 as a proof-of-concept therapeutic. *Future Med Chem* 3:45-63. doi:10.4155/fmc.10.281
62. Tohyama et al. (2008) A novel DNA vaccine-targeting macrophage migration inhibitory factor improves the survival of mice with sepsis. Gene Ther 15:1513-1522. doi:10.1038/gt.2008.112
63. Simons et al. (2011) Hypoxia-induced endothelial secretion of macrophage migration inhibitory factor and role in endothelial progenitor cell recruitment. *J Cell Mol Med.* 15:668-78. doi: 10.1111/j.1582-4934.2010.01041.x.
64. Strüßmann et al. (2013) Platelets are a previously unrecognised source of MIF. *Thromb Haemost.* 110:1004-13. doi: 10.1160/TH13-01-0049. Epub 2013 Jul. 11.
65. Wirtz et al. (2015) Platelet-derived MIF: a novel platelet chemokine with distinct recruitment properties. *Atherosclerosis.* 239:1-10. doi: 10.1016/j.atherosclerosis.2014.12.039. Epub2014-12-24
66. Fingerle-Rowson et al. (2003) The p53-dependent effects of macrophage migration inhibitory factor revealed by gene targeting. *Proc Natl Acad Sci USA* 100:9354-9359. doi:10.1073/pnas.1533295100

The invention claimed is:

1. A Macrophage Migration Inhibitory Factor (MIF) binder or MIF binding fragment thereof:
wherein the MIF binder comprises a sequence selected from the group consisting of SEQ ID Nos: 1-8 and SEQ ID Nos:10-11; or
wherein the MIF binder or MIF binding fragment thereof comprises 3 complementarity determining regions (CDR1 to CDR3, respectively), in which:
(i) CDR1 is SEQ ID NO:23, CDR2 is SEQ ID NO:45, and CDR3 is SEQ ID NO:67; or
(ii) CDR1 is SEQ ID NO:24, CDR2 is SEQ ID NO:46, and CDR3 is SEQ ID NO:68; or
(iii) CDR1 is SEQ ID NO:25, CDR2 is SEQ ID NO:47, and CDR3 is SEQ ID NO:69; or
(iv) CDR1 is SEQ ID NO:26, CDR2 is SEQ ID NO:48, and CDR3 is SEQ ID NO:70; or
(v) CDR1 is SEQ ID NO:27, CDR2 is SEQ ID NO:49, and CDR3 is SEQ ID NO:71; or
(vi) CDR1 is SEQ ID NO:28, CDR2 is SEQ ID NO:50, and CDR3 is SEQ ID NO:72; or
(vii) CDR1 is SEQ ID NO:29, CDR2 is SEQ ID NO:51, and CDR3 is SEQ ID NO:72 SEQ ID NO:73; or
(viii) CDR1 is SEQ ID NO:32, CDR2 is SEQ ID NO:54, and CDR3 is SEQ ID NO:76; or
(ix) CDR1 is SEQ ID NO:33, CDR2 is SEQ ID NO:55, and CDR3 is SEQ ID NO:77.

2. The MIF binder or MIF binding fragment thereof of claim 1, wherein the MIF binder or MIF binding fragment thereof specifically binds to SEQ ID NO: 89 or SEQ ID NO: 91.

3. The MIF binder or MIF binding fragment thereof of claim 2,
wherein the MIF binder or MIF binding fragment thereof has an on rate constant (Kon) for binding to SEQ ID NO: 89 or SEQ ID NO: 91 selected from the group consisting of at least about $10^2 M^{-1} s^{-1}$, at least about $10^3 M^{-1} s^{-1}$, at least about $10^4 M^{-1} s^{-1}$, at least about $10^5 M^{-1} s^{-1}$, at least about $10^6 M^{-1} s^{-1}$, $10^7 M^{-1} s^{-1}$, at least about $10^8 M^{-1} s^{-1}$, at least about $10^9 M^{-1} s^{-1}$, and at least about $10^{10} M^{-1} s^{-1}$; and/or
wherein the MIF binder or MIF binding fragment thereof has an off rate constant (Koff) for binding to SEQ ID NO: 89 or SEQ ID NO: 91 selected from the group consisting of at most about $10^{-3}$ s$^{-1}$, at most about $10^{-4}$ s$^{-1}$, at most about $10^{-5}$ s$^{-1}$, at most about $10^{-6}$ s$^{-1}$, at most about $10^{-7}$ s$^{-1}$, at most about $10^{-8}$ s$^{-1}$, at most about $10^{-9}$ s$^{-1}$, and at most about $10^{-10}$ s$^{-1}$; and/or wherein MIF binder or MIF binding fragment thereof binds to SEQ ID NO: 89 or SEQ ID NO: 91 with an average KD value of between 100 nM and 10 pM.

4. The MIF binder or MIF binding fragment thereof of claim 1, wherein the MIF binder or MIF binding fragment thereof is an immunoglobulin single variable domain (ISVD) or a MIF-binding fragment thereof.

5. The MIF binder or MIF binding fragment thereof of claim 1, wherein CDR1 is SEQ ID NO: 23, CDR2 is SEQ ID NO: 45, and CDR3 is SEQ ID NO: 67.

6. A polypeptide comprising at least one MIF binder or MIF binding fragment of claim 1.

7. The polypeptide of claim 6, wherein the polypeptide further comprises a serum protein binding moiety or serum protein.

8. The polypeptide of claim 7, wherein the serum protein binding moiety or serum protein is selected from the group consisting of SEQ ID NOs: 119-122.

9. The polypeptide of claim 6, wherein the polypeptide further comprises one or more other groups, residues, moieties or binding units selected from the group consisting of a polyethylene glycol molecule, serum proteins or fragments thereof, binding units that can bind to serum proteins, an Fc portion, and small proteins or peptides that can bind to serum proteins.

10. The MIF binder or MIF binding fragment thereof of claim 1, wherein wherein CDR1 is SEQ ID NO:23, CDR2 is SEQ ID NO:45, and CDR3 is SEQ ID NO:67; or wherein CDR1 is SEQ ID NO:25, CDR2 is SEQ ID NO:47, and CDR3 is SEQ ID NO:69; or wherein CDR1 is SEQ ID NO:28, CDR2 is SEQ ID NO:50, and CDR3 is SEQ ID NO:72.

11. The MIF binder or MIF binding fragment thereof of claim 10, wherein the MIF binder or MIF binding fragment thereof:

inhibits an inflammatory immune response by more than about 10%; and/or inhibits tautomerase activity by more than about 10%; and/or inhibits TNF-induction by more than about 10%; and/or inhibits TNF-secretion by more than about 10%; and or inhibits a MIF activity by more than about 10%; and/or inhibits inflammation by more than about 10%.

* * * * *

UNITED STATES PATENT AND TRADEMARK OFFICE
CERTIFICATE OF CORRECTION

Page 1 of 1

PATENT NO. : 11,098,113 B2
APPLICATION NO. : 16/333730
DATED : August 24, 2021
INVENTOR(S) : Peter Vanlandschoot et al.

It is certified that error appears in the above-identified patent and that said Letters Patent is hereby corrected as shown below:

In the Claims

In Column 144, Line 47, Claim 1: please replace "and CDR3 is SEQ ID N0:72 SEQ ID N0:73; or" with --and CDR3 is SEQ ID NO:73; or--

Signed and Sealed this
Fifth Day of October, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 130

<210> SEQ ID NO 1
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 1

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Leu Ser Asn Ser
            20                  25                  30

```
Ile Met Gly Trp Phe Arg Gln Ala Pro Gly Lys Glu Arg Glu Phe Val
            35                  40                  45

Ala Asn Ile Asn Trp Ser Gly Thr Ser Arg Leu Tyr Ala Asp Ser Val
 50                      55                  60

Lys Gly Arg Phe Thr Ile Ser Arg Asp Asn Thr Lys Ser Thr Val Tyr
 65                  70                  75                  80

Leu Gln Met Asn Ser Leu Lys Pro Glu Asp Thr Ala Ile Tyr Tyr Cys
                 85                  90                  95

Ala Ala Arg Ser Ser Thr Met Ser Ala Thr Asp Tyr Trp Gly Gln Gly
                100                 105                 110

Thr Gln Val Thr Val Ser Ser
            115
```

<210> SEQ ID NO 2
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 2

```
Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Ile Ser Ser Tyr
             20                  25                  30

Ile Val Gly Trp Phe Arg Gln Ala Pro Gly Lys Glu Arg Glu Phe Val
            35                  40                  45

Ala Asn Ile Gly Trp Ser Gly Ser Met Pro Leu Tyr Ala Asp Ser Val
 50                      55                  60

Lys Gly Arg Phe Thr Ile Phe Arg Asp Asn Ala Lys Asn Thr Val Tyr
 65                  70                  75                  80

Leu Glu Met Asn Lys Leu Lys Pro Glu Asp Thr Ala Val Tyr Tyr Cys
                 85                  90                  95

Ala Ala Arg Gly Ala Gly Gln Leu Thr Asn Asp Tyr Trp Gly Gln Gly
                100                 105                 110

Thr Gln Val Thr Val Ser Ser
            115
```

<210> SEQ ID NO 3
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 3

```
Glu Val Gln Leu Val Glu Ser Gly Gly Gly Leu Val His Ala Gly Gly
 1               5                  10                  15

Ser Leu Arg Leu Ser Cys Ala Ser Gly Arg Thr Phe Ser Ser Tyr
             20                  25                  30

Phe Met Gly Trp Phe Arg Gln Ala Pro Gly Lys Ala Arg Glu Phe Val
            35                  40                  45

Ala Asn Ile Asn Phe Ser Gly Thr Thr Val Tyr Ala Ser Ser Val
 50                      55                  60

Lys Gly Arg Phe Thr Ile Ser Arg Asp Asn Ser Lys Asn Thr Val Tyr
 65                  70                  75                  80

Leu Gln Met Asn Ser Val Lys Pro Glu Asp Thr Ala Val Tyr Tyr Cys
                 85                  90                  95
```

```
Val Ala Arg Gly Leu Thr Gln Asp Tyr Asp Tyr Trp Gly Gln Gly Thr
            100                 105                 110

Gln Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 4

Glu Val Gln Leu Val Glu Ser Gly Gly Gly Leu Val His Ala Gly Gly
1               5                   10                  15

Ser Leu Arg Leu Ser Cys Ala Ala Ser Gly Arg Thr Ser Ser Thr Tyr
            20                  25                  30

Phe Met Gly Trp Phe Arg Gln Ala Pro Gly Lys Ala Arg Glu Phe Val
        35                  40                  45

Ala Asn Ile Asn Phe Ser Gly Gly Thr Thr Val Tyr Ala Ser Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Val Lys Pro Glu Asp Thr Ala Val Tyr Tyr Cys
                85                  90                  95

Ser Ala Arg Gly Leu Asn Gln Glu Tyr Asp Phe Trp Gly Gln Gly Thr
            100                 105                 110

Gln Val Thr Val Ser Ser
        115

<210> SEQ ID NO 5
<211> LENGTH: 112
<212> TYPE: PRT
<213> ORGANISM: Artificial Sequence
<220> FEATURE:
<223> OTHER INFORMATION: Nanobody Sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Arg Thr Tyr
            20                  25                  30

Ala Met Ser Trp Val Arg Gln Ala Pro Gly Lys Gly Ser Glu Trp Val
        35                  40                  45

Ser Thr Ile Asn Asn Gly Gly Gly Val Thr Gly Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Gly Thr Ser Arg Gly Gln Gly Thr Gln Val Thr Val Ser Ser
            100                 105                 110

<210> SEQ ID NO 6
<211> LENGTH: 118
<212> TYPE: PRT
<213> ORGANISM: Artificial Sequence
<220> FEATURE:
<223> OTHER INFORMATION: Nanobody Sequence
```

<400> SEQUENCE: 6

Glu Val Gln Leu Val Glu Ser Gly Gly Gly Leu Val Gln Asp Gly Gly
1               5                   10                  15

Ser Leu Arg Leu Ser Cys Ala Ala Ser Gly Arg Thr Ala Ser Ile Gln
            20                  25                  30

Val Met Gly Trp Phe Arg Gln Ala Pro Gly Lys Glu Arg Glu Phe Val
        35                  40                  45

Gly Asn Ile Gly Trp Asn Tyr Gly Leu Thr Leu Tyr Ala Asp Pro Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Arg Ile Gly Thr Ile Thr Tyr Asp Tyr Trp Gly Gln Gly Thr
            100                 105                 110

Gln Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 7

Glu Val Gln Leu Val Glu Ser Gly Gly Gly Leu Val Gln Asp Gly Gly
1               5                   10                  15

Ser Leu Arg Leu Ser Cys Ala Ala Ser Gly Arg Thr Ala Ser Ile His
            20                  25                  30

Thr Met Gly Trp Phe Arg Gln Ala Pro Gly Gln Glu Arg Gly Phe Val
        35                  40                  45

Gly Asn Ile Gly Trp Asn Tyr Gly Leu Thr Leu Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Arg Ile Gly Thr Thr Pro Tyr Asp Tyr Trp Gly Gln Gly Thr
            100                 105                 110

Gln Val Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 8

Lys Val Gln Leu Val Glu Ser Gly Gly Gly Leu Val Gln Asp Gly Gly
1               5                   10                  15

Ser Leu Arg Leu Ser Cys Ala Ala Ser Gly Arg Thr Ala Ser Ile Gln
            20                  25                  30

Val Met Gly Trp Phe Arg Gln Ala Pro Gly Lys Glu Arg Glu Phe Val
        35                  40                  45

```
Gly Asn Ile Gly Trp Asn Tyr Gly Leu Thr Leu Tyr Pro Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Ala Arg Ile Gly Thr Thr Thr Tyr Asp Tyr Trp Gly Gln Gly Thr
                100                 105                 110

Gln Val Thr Val Ser Ser
                115

<210> SEQ ID NO 9
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 9

Glu Val Gln Leu Val Glu Ser Gly Gly Gly Leu Val Gln Asp Gly Gly
 1                   5                  10                  15

Ser Leu Arg Leu Ser Cys Ala Ala Ser Gly Arg Thr Ala Ser Ile Gln
                 20                  25                  30

Val Met Gly Trp Phe Arg Gln Ala Pro Gly Lys Glu Arg Glu Phe Val
             35                  40                  45

Gly Asn Ile Gly Trp Asn Tyr Gly Leu Thr Leu Tyr Pro Asp Ser Val
        50                  55                  60

Lys Gly Arg Phe Thr Ile Ser Arg Gly Asn Ala Lys Asn Ala Val Tyr
 65                  70                  75                  80

Leu Gln Met Asn Asn Leu Lys Pro Glu Asp Thr Ala Val Tyr Tyr Cys
                85                  90                  95

Ala Ala Arg Ile Gly Thr Thr Thr Tyr Asp Tyr Trp Gly Gln Gly Thr
                100                 105                 110

Gln Val Thr Val Ser Ser
                115

<210> SEQ ID NO 10
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 10

Glu Val Gln Leu Val Glu Ser Gly Gly Gly Leu Val Gln Ala Gly Gly
 1                   5                  10                  15

Ser Leu Arg Leu Ser Cys Ala Ala Ser Gly Arg Thr Ser Ser Ile Val
                 20                  25                  30

Ala Ile Gly Trp Phe Arg Gln Ala Pro Gly Lys Glu Arg Glu Phe Val
             35                  40                  45

Ser Asn Ile Gly Trp Lys Phe Gly Ser Thr Val Tyr Val Asp Ser Val
        50                  55                  60

Lys Gly Arg Phe Thr Ile Ser Lys Asp Asn Ala Lys Asn Thr Val Tyr
 65                  70                  75                  80

Leu Gln Met Asn Ser Leu Lys Pro Glu Asp Thr Ala Val Tyr Arg Cys
                85                  90                  95

Ala Ala Arg Ser Asp Gly Arg Val Tyr Asp Ser Trp Gly Gln Gly Thr
```

Gln Val Thr Val Ser Ser
        115

<210> SEQ ID NO 11
<211> LENGTH: 120
<212> TYPE: PRT
<213> ORGANISM: Artificial Sequence
<220> FEATURE:
<223> OTHER INFORMATION: Nanobody Sequence

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Asn Tyr
            20                  25                  30

Ile Met Gly Trp Phe Arg Gln Ala Pro Gly Lys Glu Arg Glu Phe Val
        35                  40                  45

Ala Asn Ile Ser Trp Asn Tyr Gly Thr Thr Phe Tyr Ala Asp Ser Val
    50                  55                  60

Lys Gly Arg Phe Thr Ile Ser Gly Asp Ser Ala Lys Asn Thr Val Tyr
65                  70                  75                  80

Leu Gln Met Thr Ser Leu Lys Pro Glu Asp Thr Ala Val Tyr Tyr Cys
                85                  90                  95

Ala Ala Arg Pro Val Arg Gly Gly Arg Asn Phe Asp Tyr Trp Gly Gln
            100                 105                 110

Gly Thr Gln Val Thr Val Ser Ser
        115                 120

<210> SEQ ID NO 12
<211> LENGTH: 25
<212> TYPE: PRT
<213> ORGANISM: Artificial Sequence
<220> FEATURE:
<223> OTHER INFORMATION: FR1

<400> SEQUENCE: 12

Glu Val Gln Leu Val Glu Ser Gly Gly Gly Ser Val Gln Ala Gly Asp
1               5                   10                  15

Ser Leu Arg Leu Ser Cys Ala Ala Ser
            20                  25

<210> SEQ ID NO 13
<211> LENGTH: 25
<212> TYPE: PRT
<213> ORGANISM: Artificial Sequence
<220> FEATURE:
<223> OTHER INFORMATION: FR1

<400> SEQUENCE: 13

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 14
<211> LENGTH: 25
<212> TYPE: PRT
<213> ORGANISM: Artificial Sequence
<220> FEATURE:
<223> OTHER INFORMATION: FR1

-continued

```
<400> SEQUENCE: 14

Glu Val Gln Leu Val Glu Ser Gly Gly Gly Leu Val His Ala Gly Gly
1               5                   10                  15

Ser Leu Arg Leu Ser Cys Ala Ala Ser
            20                  25

<210> SEQ ID NO 15
<211> LENGTH: 25
<212> TYPE: PRT
<213> ORGANISM: Artificial Sequence
<220> FEATURE:
<223> OTHER INFORMATION: FR1

<400> SEQUENCE: 15

Glu Val Gln Leu Val Glu Ser Gly Gly Gly Leu Val His Ala Gly Gly
1               5                   10                  15

Ser Leu Arg Leu Ser Cys Ala Ala Ser
            20                  25

<210> SEQ ID NO 16
<211> LENGTH: 25
<212> TYPE: PRT
<213> ORGANISM: Artificial Sequence
<220> FEATURE:
<223> OTHER INFORMATION: FR1

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: FR1

<400> SEQUENCE: 17

Glu Val Gln Leu Val Glu Ser Gly Gly Gly Leu Val Gln Asp Gly Gly
1               5                   10                  15

Ser Leu Arg Leu Ser Cys Ala Ala Ser
            20                  25

<210> SEQ ID NO 18
<211> LENGTH: 25
<212> TYPE: PRT
<213> ORGANISM: Artificial Sequence
<220> FEATURE:
<223> OTHER INFORMATION: FR1

<400> SEQUENCE: 18

Glu Val Gln Leu Val Glu Ser Gly Gly Gly Leu Val Gln Asp Gly Gly
1               5                   10                  15

Ser Leu Arg Leu Ser Cys Ala Ala Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: FR1
```

<400> SEQUENCE: 19

Lys Val Gln Leu Val Glu Ser Gly Gly Gly Leu Val Gln Asp Gly Gly
1               5                   10                  15

Ser Leu Arg Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: FR1

<400> SEQUENCE: 20

Glu Val Gln Leu Val Glu Ser Gly Gly Gly Leu Val Gln Asp Gly Gly
1               5                   10                  15

Ser Leu Arg Leu Ser Cys Ala Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: FR1

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: FR1

<400> SEQUENCE: 22

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 23
<211> LENGTH: 8
<212> TYPE: PRT
<213> ORGANISM: Artificial Sequence
<220> FEATURE:
<223> OTHER INFORMATION: CDR1

<400> SEQUENCE: 23

Gly Arg Thr Leu Ser Asn Ser Ile
1               5

<210> SEQ ID NO 24
<211> LENGTH: 8
<212> TYPE: PRT
<213> ORGANISM: Artificial Sequence
<220> FEATURE:
<223> OTHER INFORMATION: CDR1

<400> SEQUENCE: 24

```
Gly Arg Thr Ile Ser Ser Tyr Ile
1               5
```

<210> SEQ ID NO 25
<211> LENGTH: 8
<212> TYPE: PRT
<213> ORGANISM: Artificial Sequence
<220> FEATURE:
<223> OTHER INFORMATION: CDR1

<400> SEQUENCE: 25

```
Gly Arg Thr Phe Ser Ser Tyr Phe
1               5
```

<210> SEQ ID NO 26
<211> LENGTH: 8
<212> TYPE: PRT
<213> ORGANISM: Artificial Sequence
<220> FEATURE:
<223> OTHER INFORMATION: CDR1

<400> SEQUENCE: 26

```
Gly Arg Thr Ser Ser Thr Tyr Phe
1               5
```

<210> SEQ ID NO 27
<211> LENGTH: 8
<212> TYPE: PRT
<213> ORGANISM: Artificial Sequence
<220> FEATURE:
<223> OTHER INFORMATION: CDR1

<400> SEQUENCE: 27

```
Gly Phe Thr Phe Arg Thr Tyr Ala
1               5
```

<210> SEQ ID NO 28
<211> LENGTH: 8
<212> TYPE: PRT
<213> ORGANISM: Artificial Sequence
<220> FEATURE:
<223> OTHER INFORMATION: CDR1

<400> SEQUENCE: 28

```
Gly Arg Thr Ala Ser Ile Gln Val
1               5
```

<210> SEQ ID NO 29
<211> LENGTH: 8
<212> TYPE: PRT
<213> ORGANISM: Artificial Sequence
<220> FEATURE:
<223> OTHER INFORMATION: CDR1

<400> SEQUENCE: 29

```
Gly Arg Thr Ala Ser Ile His Thr
1               5
```

<210> SEQ ID NO 30
<211> LENGTH: 8
<212> TYPE: PRT
<213> ORGANISM: Artificial Sequence
<220> FEATURE:
<223> OTHER INFORMATION: CDR1

<400> SEQUENCE: 30

```
Gly Arg Thr Ala Ser Ile Gln Val
1               5

<210> SEQ ID NO 31
<211> LENGTH: 8
<212> TYPE: PRT
<213> ORGANISM: Artificial Sequence
<220> FEATURE:
<223> OTHER INFORMATION: CDR1

<400> SEQUENCE: 31

Gly Arg Thr Ala Ser Ile Gln Val
1               5

<210> SEQ ID NO 32
<211> LENGTH: 8
<212> TYPE: PRT
<213> ORGANISM: Artificial Sequence
<220> FEATURE:
<223> OTHER INFORMATION: CDR1

<400> SEQUENCE: 32

Gly Arg Thr Ser Ser Ile Val Ala
1               5

<210> SEQ ID NO 33
<211> LENGTH: 8
<212> TYPE: PRT
<213> ORGANISM: Artificial Sequence
<220> FEATURE:
<223> OTHER INFORMATION: CDR1

<400> SEQUENCE: 33

Gly Arg Ser Phe Ser Asn Tyr Ile
1               5

<210> SEQ ID NO 34
<211> LENGTH: 17
<212> TYPE: PRT
<213> ORGANISM: Artificial Sequence
<220> FEATURE:
<223> OTHER INFORMATION: FR2

<400> SEQUENCE: 34

Met Gly Trp Phe Arg Gln Ala Pro Gly Lys Glu Arg Glu Phe Val Ala
1               5                   10                  15

Asn

<210> SEQ ID NO 35
<211> LENGTH: 17
<212> TYPE: PRT
<213> ORGANISM: Artificial Sequence
<220> FEATURE:
<223> OTHER INFORMATION: FR2

<400> SEQUENCE: 35

Val Gly Trp Phe Arg Gln Ala Pro Gly Lys Glu Arg Glu Phe Val Ala
1               5                   10                  15

Asn

<210> SEQ ID NO 36
<211> LENGTH: 17
<212> TYPE: PRT
<213> ORGANISM: Artificial Sequence
<220> FEATURE:
<223> OTHER INFORMATION: FR2
```

<400> SEQUENCE: 36

Met Gly Trp Phe Arg Gln Ala Pro Gly Lys Ala Arg Glu Phe Val Ala
1               5                   10                  15

Asn

<210> SEQ ID NO 37
<211> LENGTH: 17
<212> TYPE: PRT
<213> ORGANISM: Artificial Sequence
<220> FEATURE:
<223> OTHER INFORMATION: FR2

<400> SEQUENCE: 37

Met Gly Trp Phe Arg Gln Ala Pro Gly Lys Ala Arg Glu Phe Val Ala
1               5                   10                  15

Asn

<210> SEQ ID NO 38
<211> LENGTH: 17
<212> TYPE: PRT
<213> ORGANISM: Artificial Sequence
<220> FEATURE:
<223> OTHER INFORMATION: FR2

<400> SEQUENCE: 38

Met Ser Trp Val Arg Gln Ala Pro Gly Lys Gly Ser Glu Trp Val Ser
1               5                   10                  15

Thr

<210> SEQ ID NO 39
<211> LENGTH: 17
<212> TYPE: PRT
<213> ORGANISM: Artificial Sequence
<220> FEATURE:
<223> OTHER INFORMATION: FR2

<400> SEQUENCE: 39

Met Gly Trp Phe Arg Gln Ala Pro Gly Lys Glu Arg Glu Phe Val Gly
1               5                   10                  15

Asn

<210> SEQ ID NO 40
<211> LENGTH: 17
<212> TYPE: PRT
<213> ORGANISM: Artificial Sequence
<220> FEATURE:
<223> OTHER INFORMATION: FR2

<400> SEQUENCE: 40

Met Gly Trp Phe Arg Gln Ala Pro Gly Gln Glu Arg Gly Phe Val Gly
1               5                   10                  15

Asn

<210> SEQ ID NO 41
<211> LENGTH: 17
<212> TYPE: PRT
<213> ORGANISM: Artificial Sequence
<220> FEATURE:
<223> OTHER INFORMATION: FR2

<400> SEQUENCE: 41

Met Gly Trp Phe Arg Gln Ala Pro Gly Lys Glu Arg Glu Phe Val Gly
1               5                   10                  15

```
1               5                  10                 15

Asn

<210> SEQ ID NO 42
<211> LENGTH: 17
<212> TYPE: PRT
<213> ORGANISM: Artificial Sequence
<220> FEATURE:
<223> OTHER INFORMATION: FR2

<400> SEQUENCE: 42

Met Gly Trp Phe Arg Gln Ala Pro Gly Lys Glu Arg Glu Phe Val Gly
1               5                  10                 15

Asn

<210> SEQ ID NO 43
<211> LENGTH: 17
<212> TYPE: PRT
<213> ORGANISM: Artificial Sequence
<220> FEATURE:
<223> OTHER INFORMATION: FR2

<400> SEQUENCE: 43

Ile Gly Trp Phe Arg Gln Ala Pro Gly Lys Glu Arg Glu Phe Val Ser
1               5                  10                 15

Asn

<210> SEQ ID NO 44
<211> LENGTH: 17
<212> TYPE: PRT
<213> ORGANISM: Artificial Sequence
<220> FEATURE:
<223> OTHER INFORMATION: FR2

<400> SEQUENCE: 44

Met Gly Trp Phe Arg Gln Ala Pro Gly Lys Glu Arg Glu Phe Val Ala
1               5                  10                 15

Asn

<210> SEQ ID NO 45
<211> LENGTH: 8
<212> TYPE: PRT
<213> ORGANISM: Artificial Sequence
<220> FEATURE:
<223> OTHER INFORMATION: CDR2

<400> SEQUENCE: 45

Ile Asn Trp Ser Gly Thr Ser Arg
1               5

<210> SEQ ID NO 46
<211> LENGTH: 8
<212> TYPE: PRT
<213> ORGANISM: Artificial Sequence
<220> FEATURE:
<223> OTHER INFORMATION: CDR2

<400> SEQUENCE: 46

Ile Gly Trp Ser Gly Ser Met Pro
1               5

<210> SEQ ID NO 47
<211> LENGTH: 8
<212> TYPE: PRT
```

```
<213> ORGANISM: Artificial Sequence
<220> FEATURE:
<223> OTHER INFORMATION: CDR2

<400> SEQUENCE: 47

Ile Asn Phe Ser Gly Gly Thr Thr
1               5

<210> SEQ ID NO 48
<211> LENGTH: 8
<212> TYPE: PRT
<213> ORGANISM: Artificial Sequence
<220> FEATURE:
<223> OTHER INFORMATION: CDR2

<400> SEQUENCE: 48

Ile Asn Phe Ser Gly Gly Thr Thr
1               5

<210> SEQ ID NO 49
<211> LENGTH: 8
<212> TYPE: PRT
<213> ORGANISM: Artificial Sequence
<220> FEATURE:
<223> OTHER INFORMATION: CDR2

<400> SEQUENCE: 49

Ile Asn Asn Gly Gly Gly Val Thr
1               5

<210> SEQ ID NO 50
<211> LENGTH: 8
<212> TYPE: PRT
<213> ORGANISM: Artificial Sequence
<220> FEATURE:
<223> OTHER INFORMATION: CDR2

<400> SEQUENCE: 50

Ile Gly Trp Asn Tyr Gly Leu Thr
1               5

<210> SEQ ID NO 51
<211> LENGTH: 8
<212> TYPE: PRT
<213> ORGANISM: Artificial Sequence
<220> FEATURE:
<223> OTHER INFORMATION: CDR2

<400> SEQUENCE: 51

Ile Gly Trp Asn Tyr Gly Leu Thr
1               5

<210> SEQ ID NO 52
<211> LENGTH: 8
<212> TYPE: PRT
<213> ORGANISM: Artificial Sequence
<220> FEATURE:
<223> OTHER INFORMATION: CDR2

<400> SEQUENCE: 52

Ile Gly Trp Asn Tyr Gly Leu Thr
1               5

<210> SEQ ID NO 53
<211> LENGTH: 8
<212> TYPE: PRT
<213> ORGANISM: Artificial Sequence
```

```
<220> FEATURE:
<223> OTHER INFORMATION: CDR2

<400> SEQUENCE: 53

Ile Gly Trp Asn Tyr Gly Leu Thr
1               5

<210> SEQ ID NO 54
<211> LENGTH: 8
<212> TYPE: PRT
<213> ORGANISM: Artificial Sequence
<220> FEATURE:
<223> OTHER INFORMATION: CDR2

<400> SEQUENCE: 54

Ile Gly Trp Lys Phe Gly Ser Thr
1               5

<210> SEQ ID NO 55
<211> LENGTH: 8
<212> TYPE: PRT
<213> ORGANISM: Artificial Sequence
<220> FEATURE:
<223> OTHER INFORMATION: CDR2

<400> SEQUENCE: 55

Ile Ser Trp Asn Tyr Gly Thr Thr
1               5

<210> SEQ ID NO 56
<211> LENGTH: 38
<212> TYPE: PRT
<213> ORGANISM: Artificial Sequence
<220> FEATURE:
<223> OTHER INFORMATION: FR3

<400> SEQUENCE: 56

Leu Tyr Ala Asp Ser Val Lys Gly Arg Phe Thr Ile Ser Arg Asp Asn
1               5                   10                  15

Thr Lys Ser Thr Val Tyr Leu Gln Met Asn Ser Leu Lys Pro Glu Asp
            20                  25                  30

Thr Ala Ile Tyr Tyr Cys
        35

<210> SEQ ID NO 57
<211> LENGTH: 38
<212> TYPE: PRT
<213> ORGANISM: Artificial Sequence
<220> FEATURE:
<223> OTHER INFORMATION: FR3

<400> SEQUENCE: 57

Leu Tyr Ala Asp Ser Val Lys Gly Arg Phe Thr Ile Phe Arg Asp Asn
1               5                   10                  15

Ala Lys Asn Thr Val Tyr Leu Glu Met Asn Lys Leu Lys Pro Glu Asp
            20                  25                  30

Thr Ala Val Tyr Tyr Cys
        35

<210> SEQ ID NO 58
<211> LENGTH: 38
<212> TYPE: PRT
<213> ORGANISM: Artificial Sequence
<220> FEATURE:
<223> OTHER INFORMATION: FR3
```

<400> SEQUENCE: 58

Val Tyr Ala Ser Ser Val Lys Gly Arg Phe Thr Ile Ser Arg Asp Asn
1               5                   10                  15

Ser Lys Asn Thr Val Tyr Leu Gln Met Asn Ser Val Lys Pro Glu Asp
            20                  25                  30

Thr Ala Val Tyr Tyr Cys
            35

<210> SEQ ID NO 59
<211> LENGTH: 38
<212> TYPE: PRT
<213> ORGANISM: Artificial Sequence
<220> FEATURE:
<223> OTHER INFORMATION: FR3

<400> SEQUENCE: 59

Val Tyr Ala Ser Ser Val Lys Gly Arg Phe Thr Ile Ser Arg Asp Asn
1               5                   10                  15

Ser Lys Asn Thr Val Tyr Leu Gln Leu Asn Ser Val Lys Pro Glu Asp
            20                  25                  30

Thr Ala Val Tyr Tyr Cys
            35

<210> SEQ ID NO 60
<211> LENGTH: 38
<212> TYPE: PRT
<213> ORGANISM: Artificial Sequence
<220> FEATURE:
<223> OTHER INFORMATION: FR3

<400> SEQUENCE: 60

Gly Tyr Ala Asp Ser Val Glu Gly Arg Phe Thr Ile Ser Arg Asp Asn
1               5                   10                  15

Ala Lys Asn Thr Leu Tyr Leu Gln Met Asn Ser Leu Lys Pro Glu Asp
            20                  25                  30

Thr Ala Val Tyr Tyr Cys
            35

<210> SEQ ID NO 61
<211> LENGTH: 38
<212> TYPE: PRT
<213> ORGANISM: Artificial Sequence
<220> FEATURE:
<223> OTHER INFORMATION: FR3

<400> SEQUENCE: 61

Leu Tyr Ala Asp Pro Val Lys Gly Arg Phe Thr Ile Ser Arg Asp Asn
1               5                   10                  15

Ala Lys Asn Thr Val Tyr Leu Gln Met Asn Asn Leu Lys Pro Glu Asp
            20                  25                  30

Thr Ala Val Tyr Tyr Cys
            35

<210> SEQ ID NO 62
<211> LENGTH: 38
<212> TYPE: PRT
<213> ORGANISM: Artificial Sequence
<220> FEATURE:
<223> OTHER INFORMATION: FR3

<400> SEQUENCE: 62

Leu Tyr Ala Asp Ser Val Lys Gly Arg Phe Thr Ile Ser Arg Asp Asn
1               5                   10                  15

Ala Lys Asn Thr Val Tyr Leu Gln Met Asn Asn Leu Lys Pro Glu Asp
            20                  25                  30

Thr Ala Val Tyr Tyr Cys
        35

<210> SEQ ID NO 63
<211> LENGTH: 38
<212> TYPE: PRT
<213> ORGANISM: Artificial Sequence
<220> FEATURE:
<223> OTHER INFORMATION: FR3

<400> SEQUENCE: 63

Leu Tyr Pro Asp Ser Val Lys Gly Arg Phe Thr Ile Ser Arg Asp Asn
1               5                   10                  15

Ala Lys Asn Thr Val Tyr Leu Gln Met Asn Asn Leu Lys Pro Glu Asp
            20                  25                  30

Thr Ala Val Tyr Tyr Cys
        35

<210> SEQ ID NO 64
<211> LENGTH: 38
<212> TYPE: PRT
<213> ORGANISM: Artificial Sequence
<220> FEATURE:
<223> OTHER INFORMATION: FR3

<400> SEQUENCE: 64

Leu Tyr Pro Asp Ser Val Lys Gly Arg Phe Thr Ile Ser Arg Gly Asn
1               5                   10                  15

Ala Lys Asn Ala Val Tyr Leu Gln Met Asn Asn Leu Lys Pro Glu Asp
            20                  25                  30

Thr Ala Val Tyr Tyr Cys
        35

<210> SEQ ID NO 65
<211> LENGTH: 38
<212> TYPE: PRT
<213> ORGANISM: Artificial Sequence
<220> FEATURE:
<223> OTHER INFORMATION: FR3

<400> SEQUENCE: 65

Val Tyr Val Asp Ser Val Lys Gly Arg Phe Thr Ile Ser Lys Asp Asn
1               5                   10                  15

Ala Lys Asn Thr Val Tyr Leu Gln Met Asn Ser Leu Lys Pro Glu Asp
            20                  25                  30

Thr Ala Val Tyr Arg Cys
        35

<210> SEQ ID NO 66
<211> LENGTH: 38
<212> TYPE: PRT
<213> ORGANISM: Artificial Sequence
<220> FEATURE:
<223> OTHER INFORMATION: FR3

<400> SEQUENCE: 66

Phe Tyr Ala Asp Ser Val Lys Gly Arg Phe Thr Ile Ser Gly Asp Ser
1               5                   10                  15

Ala Lys Asn Thr Val Tyr Leu Gln Met Thr Ser Leu Lys Pro Glu Asp
            20                  25                  30

Thr Ala Val Tyr Tyr Cys
        35

<210> SEQ ID NO 67
<211> LENGTH: 12
<212> TYPE: PRT
<213> ORGANISM: Artificial Sequence
<220> FEATURE:
<223> OTHER INFORMATION: CDR3

<400> SEQUENCE: 67

Ala Ala Arg Ser Ser Thr Met Ser Ala Thr Asp Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: CDR3

<400> SEQUENCE: 68

Ala Ala Arg Gly Ala Gly Gln Leu Thr Asn Asp Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: CDR3

<400> SEQUENCE: 69

Val Ala Arg Gly Leu Thr Gln Asp Tyr Asp Tyr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: CDR3

<400> SEQUENCE: 70

Ser Ala Arg Gly Leu Asn Gln Glu Tyr Asp Phe
1               5                   10

<210> SEQ ID NO 71
<211> LENGTH: 5
<212> TYPE: PRT
<213> ORGANISM: Artificial Sequence
<220> FEATURE:
<223> OTHER INFORMATION: CDR3

<400> SEQUENCE: 71

Ala Lys Gly Thr Ser
1               5

<210> SEQ ID NO 72
<211> LENGTH: 11
<212> TYPE: PRT
<213> ORGANISM: Artificial Sequence
<220> FEATURE:
<223> OTHER INFORMATION: CDR3

<400> SEQUENCE: 72

Ala Ala Arg Ile Gly Thr Ile Thr Tyr Asp Tyr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: CDR3

<400> SEQUENCE: 73

Ala Ala Arg Ile Gly Thr Thr Pro Tyr Asp Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: CDR3

<400> SEQUENCE: 74

Ala Ala Arg Ile Gly Thr Thr Thr Tyr Asp Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: CDR3

<400> SEQUENCE: 75

Ala Ala Arg Ile Gly Thr Thr Thr Tyr Asp Tyr
1               5                   10

<210> SEQ ID NO 76
<211> LENGTH: 11
<212> TYPE: PRT
<213> ORGANISM: Artificial Sequence
<220> FEATURE:
<223> OTHER INFORMATION: CDR3

<400> SEQUENCE: 76

Ala Ala Arg Ser Asp Gly Arg Val Tyr Asp Ser
1               5                   10

<210> SEQ ID NO 77
<211> LENGTH: 13
<212> TYPE: PRT
<213> ORGANISM: Artificial Sequence
<220> FEATURE:
<223> OTHER INFORMATION: CDR3

<400> SEQUENCE: 77

Ala Ala Arg Pro Val Arg Gly Gly Arg Asn Phe Asp Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: FR4

<400> SEQUENCE: 78

```
<210> SEQ ID NO 79
<211> LENGTH: 11
<212> TYPE: PRT
<213> ORGANISM: Artificial Sequence
<220> FEATURE:
<223> OTHER INFORMATION: FR4

<400> SEQUENCE: 79

Trp Gly Gln Gly Thr Gln Val Thr Val Ser Ser
1               5                   10

<210> SEQ ID NO 80
<211> LENGTH: 11
<212> TYPE: PRT
<213> ORGANISM: Artificial Sequence
<220> FEATURE:
<223> OTHER INFORMATION: FR4

<400> SEQUENCE: 80

Trp Gly Gln Gly Thr Gln Val Thr Val Ser Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: FR4

<400> SEQUENCE: 81

Trp Gly Gln Gly Thr Gln Val Thr Val Ser Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: FR4

<400> SEQUENCE: 82

Arg Gly Gln Gly Thr Gln Val Thr Val Ser Ser
1               5                   10

<210> SEQ ID NO 83
<211> LENGTH: 11
<212> TYPE: PRT
<213> ORGANISM: Artificial Sequence
<220> FEATURE:
<223> OTHER INFORMATION: FR4

<400> SEQUENCE: 83

Trp Gly Gln Gly Thr Gln Val Thr Val Ser Ser
1               5                   10

<210> SEQ ID NO 84
<211> LENGTH: 11
<212> TYPE: PRT
<213> ORGANISM: Artificial Sequence
<220> FEATURE:
<223> OTHER INFORMATION: FR4

<400> SEQUENCE: 84
```

Trp Gly Gln Gly Thr Gln Val Thr Val Ser Ser
1               5                   10

-continued

Trp Gly Gln Gly Thr Gln Val Thr Val Ser Ser
1               5                   10

<210> SEQ ID NO 85
<211> LENGTH: 11
<212> TYPE: PRT
<213> ORGANISM: Artificial Sequence
<220> FEATURE:
<223> OTHER INFORMATION: FR4

<400> SEQUENCE: 85

Trp Gly Gln Gly Thr Gln Val Thr Val Ser Ser
1               5                   10

<210> SEQ ID NO 86
<211> LENGTH: 11
<212> TYPE: PRT
<213> ORGANISM: Artificial Sequence
<220> FEATURE:
<223> OTHER INFORMATION: FR4

<400> SEQUENCE: 86

Trp Gly Gln Gly Thr Gln Val Thr Val Ser Ser
1               5                   10

<210> SEQ ID NO 87
<211> LENGTH: 11
<212> TYPE: PRT
<213> ORGANISM: Artificial Sequence
<220> FEATURE:
<223> OTHER INFORMATION: FR4

<400> SEQUENCE: 87

Trp Gly Gln Gly Thr Gln Val Thr Val Ser Ser
1               5                   10

<210> SEQ ID NO 88
<211> LENGTH: 11
<212> TYPE: PRT
<213> ORGANISM: Artificial Sequence
<220> FEATURE:
<223> OTHER INFORMATION: FR4

<400> SEQUENCE: 88

Trp Gly Gln Gly Thr Gln Val Thr Val Ser Ser
1               5                   10

<210> SEQ ID NO 89
<211> LENGTH: 115
<212> TYPE: PRT
<213> ORGANISM: Homo sapiens

<400> SEQUENCE: 89

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr

```
                      85                  90                  95

Ile Asn Tyr Tyr Asp Met Asn Ala Ala Asn Val Gly Trp Asn Asn Ser
                100                 105                 110

Thr Phe Ala
        115

<210> SEQ ID NO 90
<211> LENGTH: 115
<212> TYPE: PRT
<213> ORGANISM: Macaca mulatta

<400> SEQUENCE: 90

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
                100                 105                 110

Thr Phe Ala
        115

<210> SEQ ID NO 91
<211> LENGTH: 115
<212> TYPE: PRT
<213> ORGANISM: Mus musculus

<400> SEQUENCE: 91

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Thr Asn Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Asp Arg Val Tyr
                85                  90                  95

Ile Asn Tyr Tyr Asp Met Asn Ala Ala Asn Val Gly Trp Asn Gly Ser
                100                 105                 110

Thr Phe Ala
        115

<210> SEQ ID NO 92
<211> LENGTH: 5
<212> TYPE: PRT
<213> ORGANISM: Artificial Sequence
<220> FEATURE:
<223> OTHER INFORMATION: Linker Sequences
```

<400> SEQUENCE: 92

Gly Gly Gly Gly Ser
1               5

<210> SEQ ID NO 93
<211> LENGTH: 7
<212> TYPE: PRT
<213> ORGANISM: Artificial Sequence
<220> FEATURE:
<223> OTHER INFORMATION: Linker Sequences

<400> SEQUENCE: 93

Ser Gly Gly Ser Gly Gly Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Linker Sequences

<400> SEQUENCE: 94

Gly Gly Gly Gly Ser Gly Gly Gly Ser
1               5

<210> SEQ ID NO 95
<211> LENGTH: 10
<212> TYPE: PRT
<213> ORGANISM: Artificial Sequence
<220> FEATURE:
<223> OTHER INFORMATION: Linker Sequences

<400> SEQUENCE: 95

Gly Gly Gly Gly Ser Gly Gly Gly Gly Ser
1               5                   10

<210> SEQ ID NO 96
<211> LENGTH: 15
<212> TYPE: PRT
<213> ORGANISM: Artificial Sequence
<220> FEATURE:
<223> OTHER INFORMATION: Linker Sequences

<400> SEQUENCE: 96

Gly Gly Gly Gly Ser Gly Gly Gly Ser Gly Gly Gly Gly Ser
1               5                   10                  15

<210> SEQ ID NO 97
<211> LENGTH: 18
<212> TYPE: PRT
<213> ORGANISM: Artificial Sequence
<220> FEATURE:
<223> OTHER INFORMATION: Linker Sequences

<400> SEQUENCE: 97

Gly Gly Gly Gly Ser Gly Gly Gly Gly Ser Gly Gly Gly Gly Gly
1               5                   10                  15

Gly Ser

<210> SEQ ID NO 98
<211> LENGTH: 20
<212> TYPE: PRT
<213> ORGANISM: Artificial Sequence
<220> FEATURE:

<223> OTHER INFORMATION: Linker Sequences

<400> SEQUENCE: 98

Gly Gly Gly Gly Ser Gly Gly Gly Gly Ser Gly Gly Gly Ser Gly
1               5                   10                  15

Gly Gly Gly Ser
            20

<210> SEQ ID NO 99
<211> LENGTH: 25
<212> TYPE: PRT
<213> ORGANISM: Artificial Sequence
<220> FEATURE:
<223> OTHER INFORMATION: Linker Sequences

<400> SEQUENCE: 99

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25

<210> SEQ ID NO 100
<211> LENGTH: 30
<212> TYPE: PRT
<213> ORGANISM: Artificial Sequence
<220> FEATURE:
<223> OTHER INFORMATION: Linker Sequences

<400> SEQUENCE: 100

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 101
<211> LENGTH: 35
<212> TYPE: PRT
<213> ORGANISM: Artificial Sequence
<220> FEATURE:
<223> OTHER INFORMATION: Linker Sequences

<400> SEQUENCE: 101

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser
        35

<210> SEQ ID NO 102
<211> LENGTH: 3
<212> TYPE: PRT
<213> ORGANISM: Artificial Sequence
<220> FEATURE:
<223> OTHER INFORMATION: Linker Sequences

<400> SEQUENCE: 102

Ala Ala Ala
1

<210> SEQ ID NO 103
<211> LENGTH: 115
<212> TYPE: PRT
<213> ORGANISM: Artificial Sequence
<220> FEATURE:
<223> OTHER INFORMATION: Nanobody binds Albumin

<400> SEQUENCE: 103

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 104
<211> LENGTH: 115
<212> TYPE: PRT
<213> ORGANISM: Artificial Sequence
<220> FEATURE:
<223> OTHER INFORMATION: Nanobody binds Albumin

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 105
<211> LENGTH: 116
<212> TYPE: PRT
<213> ORGANISM: Artificial Sequence
<220> FEATURE:
<223> OTHER INFORMATION: Nanobody binds Albumin

<400> SEQUENCE: 105

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

```
Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
                100                 105                 110

Val Ser Ser Ala
            115

<210> SEQ ID NO 106
<211> LENGTH: 116
<212> TYPE: PRT
<213> ORGANISM: Artificial Sequence
<220> FEATURE:
<223> OTHER INFORMATION: Nanobody binds Albumin

<400> SEQUENCE: 106

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
                100                 105                 110

Val Ser Ser Ala
            115

<210> SEQ ID NO 107
<211> LENGTH: 115
<212> TYPE: PRT
<213> ORGANISM: Artificial Sequence
<220> FEATURE:
<223> OTHER INFORMATION: Nanobody binds Albumin

<400> SEQUENCE: 107

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95
```

```
Thr Ile Gly Gly Ser Leu Ser Arg Ser Ser Gln Gly Thr Leu Val Thr
            100                 105                 110

Val Ser Ser
        115

<210> SEQ ID NO 108
<211> LENGTH: 116
<212> TYPE: PRT
<213> ORGANISM: Artificial Sequence
<220> FEATURE:
<223> OTHER INFORMATION: Nanobody binds Albumin

<400> SEQUENCE: 108

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 109
<211> LENGTH: 115
<212> TYPE: PRT
<213> ORGANISM: Artificial Sequence
<220> FEATURE:
<223> OTHER INFORMATION: Nanobody binds Albumin

<400> SEQUENCE: 109

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 110
<211> LENGTH: 116
<212> TYPE: PRT
```

```
<213> ORGANISM: Artificial Sequence
<220> FEATURE:
<223> OTHER INFORMATION: Nanobody binds Albumin

<400> SEQUENCE: 110

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 111
<211> LENGTH: 117
<212> TYPE: PRT
<213> ORGANISM: Artificial Sequence
<220> FEATURE:
<223> OTHER INFORMATION: Nanobody binds Albumin

<400> SEQUENCE: 111

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 112
<211> LENGTH: 118
<212> TYPE: PRT
<213> ORGANISM: Artificial Sequence
<220> FEATURE:
<223> OTHER INFORMATION: Nanobody binds Albumin

<400> SEQUENCE: 112

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30
```

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Ala Ala Ala
            115

<210> SEQ ID NO 113
<211> LENGTH: 116
<212> TYPE: PRT
<213> ORGANISM: Artificial Sequence
<220> FEATURE:
<223> OTHER INFORMATION: Nanobody binds Albumin

<400> SEQUENCE: 113

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Gly
            115

<210> SEQ ID NO 114
<211> LENGTH: 117
<212> TYPE: PRT
<213> ORGANISM: Artificial Sequence
<220> FEATURE:
<223> OTHER INFORMATION: Nanobody binds Albumin

<400> SEQUENCE: 114

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys

```
                    85                  90                  95
Thr Ile Gly Gly Ser Leu Ser Arg Ser Ser Gln Gly Thr Leu Val Thr
                100                 105                 110

Val Ser Ser Gly Gly
        115

<210> SEQ ID NO 115
<211> LENGTH: 118
<212> TYPE: PRT
<213> ORGANISM: Artificial Sequence
<220> FEATURE:
<223> OTHER INFORMATION: Nanobody binds Albumin

<400> SEQUENCE: 115

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
                100                 105                 110

Val Ser Ser Gly Gly
        115

<210> SEQ ID NO 116
<211> LENGTH: 5
<212> TYPE: PRT
<213> ORGANISM: Artificial Sequence
<220> FEATURE:
<223> OTHER INFORMATION: CDR1

<400> SEQUENCE: 116

Ser Phe Gly Met Ser
1               5

<210> SEQ ID NO 117
<211> LENGTH: 17
<212> TYPE: PRT
<213> ORGANISM: Artificial Sequence
<220> FEATURE:
<223> OTHER INFORMATION: CDR2

<400> SEQUENCE: 117

Ser Ile Ser Gly Ser Gly Ser Asp Thr Leu Tyr Ala Asp Ser Val Lys
1               5                   10                  15

Gly

<210> SEQ ID NO 118
<211> LENGTH: 6
<212> TYPE: PRT
<213> ORGANISM: Artificial Sequence
<220> FEATURE:
<223> OTHER INFORMATION: CDR3

<400> SEQUENCE: 118
```

```
Gly Gly Ser Leu Ser Arg
1               5

<210> SEQ ID NO 119
<211> LENGTH: 243
<212> TYPE: PRT
<213> ORGANISM: Artificial Sequence
<220> FEATURE:
<223> OTHER INFORMATION: Fusion protein

<400> SEQUENCE: 119

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Leu Ser Asn Ser
            20                  25                  30

Ile Met Gly Trp Phe Arg Gln Ala Pro Gly Lys Glu Arg Glu Phe Val
        35                  40                  45

Ala Asn Ile Asn Trp Ser Gly Thr Ser Arg Leu Tyr Ala Asp Ser Val
    50                  55                  60

Lys Gly Arg Phe Thr Ile Ser Arg Asp Asn Thr Lys Ser Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Ser Thr Met Ser Ala Thr Asp Tyr Trp Gly Gln Gly
            100                 105                 110

Thr Gln Val Thr Val Ser Ser Gly Gly Gly Ser Gly Gly Gly Ser
            115                 120                 125

Glu Val Gln Leu Val Glu Ser Gly Gly Leu Val Gln Pro Gly Asn
            130                 135                 140

Ser Leu Arg Leu Ser Cys Ala Ala Ser Gly Phe Thr Phe Ser Ser Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Ser Asp Thr Leu Tyr Ala Asp Ser Val
            180                 185                 190

Lys Gly Arg Phe Thr Ile Ser Arg Asp Asn Ala Lys Thr Thr Leu Tyr
            195                 200                 205

Leu Gln Met Asn Ser Leu Arg Pro Glu Asp Thr Ala Val Tyr Tyr Cys
        210                 215                 220

Thr Ile Gly Gly Ser Leu Ser Arg Ser Ser Gln Gly Thr Leu Val Thr
225                 230                 235                 240

Val Ser Ser

<210> SEQ ID NO 120
<211> LENGTH: 247
<212> TYPE: PRT
<213> ORGANISM: Artificial Sequence
<220> FEATURE:
<223> OTHER INFORMATION: Fusion protein

<400> SEQUENCE: 120

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Leu Ser Asn Ser
            20                  25                  30

Ile Met Gly Trp Phe Arg Gln Ala Pro Gly Lys Glu Arg Glu Phe Val
        35                  40                  45
```

```
Ala Asn Ile Asn Trp Ser Gly Thr Ser Arg Leu Tyr Ala Asp Ser Val
             50                  55                  60

Lys Gly Arg Phe Thr Ile Ser Arg Asp Asn Thr Lys Ser Thr Val Tyr
 65                  70                  75                  80

Leu Gln Met Asn Ser Leu Lys Pro Glu Asp Thr Ala Ile Tyr Tyr Cys
                 85                  90                  95

Ala Ala Arg Ser Ser Thr Met Ser Ala Thr Asp Tyr Trp Gly Gln Gly
                100                 105                 110

Thr Gln Val Thr Val Ser Ser Gly Gly Gly Ser Gly Gly Gly Ser
                115                 120                 125

Glu Val Gln Leu Val Glu Ser Gly Gly Gly Ser Val Gln Ala Gly Asp
            130                 135                 140

Ser Leu Arg Leu Ser Cys Ala Ala Ser Gly Arg Thr Leu Ser Asn Ser
145                 150                 155                 160

Ile Met Gly Trp Phe Arg Gln Ala Pro Gly Lys Glu Arg Glu Phe Val
                165                 170                 175

Ala Asn Ile Asn Trp Ser Gly Thr Ser Arg Leu Tyr Ala Asp Ser Val
                180                 185                 190

Lys Gly Arg Phe Thr Ile Ser Arg Asp Asn Thr Lys Ser Thr Val Tyr
                195                 200                 205

Leu Gln Met Asn Ser Leu Lys Pro Glu Asp Thr Ala Ile Tyr Tyr Cys
210                 215                 220

Ala Ala Arg Ser Ser Thr Met Ser Ala Thr Asp Tyr Trp Gly Gln Gly
225                 230                 235                 240

Thr Gln Val Thr Val Ser Ser
                245

<210> SEQ ID NO 121
<211> LENGTH: 371
<212> TYPE: PRT
<213> ORGANISM: Artificial Sequence
<220> FEATURE:
<223> OTHER INFORMATION: Fusion protein

<400> SEQUENCE: 121

Glu Val Gln Leu Val Glu Ser Gly Gly Gly Ser Val Gln Ala Gly Asp
 1               5                  10                  15

Ser Leu Arg Leu Ser Cys Ala Ala Ser Gly Arg Thr Leu Ser Asn Ser
                 20                  25                  30

Ile Met Gly Trp Phe Arg Gln Ala Pro Gly Lys Glu Arg Glu Phe Val
             35                  40                  45

Ala Asn Ile Asn Trp Ser Gly Thr Ser Arg Leu Tyr Ala Asp Ser Val
         50                  55                  60

Lys Gly Arg Phe Thr Ile Ser Arg Asp Asn Thr Lys Ser Thr Val Tyr
 65                  70                  75                  80

Leu Gln Met Asn Ser Leu Lys Pro Glu Asp Thr Ala Ile Tyr Tyr Cys
                 85                  90                  95

Ala Ala Arg Ser Ser Thr Met Ser Ala Thr Asp Tyr Trp Gly Gln Gly
                100                 105                 110

Thr Gln Val Thr Val Ser Ser Gly Gly Gly Gly Ser Gly Gly Gly Ser
            115                 120                 125

Glu Val Gln Leu Val Glu Ser Gly Gly Gly Leu Val Gln Pro Gly Asn
            130                 135                 140

Ser Leu Arg Leu Ser Cys Ala Ala Ser Gly Phe Thr Phe Ser Ser Phe
145                 150                 155                 160
```

```
Gly Met Ser Trp Val Arg Gln Ala Pro Gly Lys Gly Leu Glu Trp Val
            165                 170                 175

Ser Ser Ile Ser Gly Ser Gly Ser Asp Thr Leu Tyr Ala Asp Ser Val
            180                 185                 190

Lys Gly Arg Phe Thr Ile Ser Arg Asp Asn Ala Lys Thr Thr Leu Tyr
            195                 200                 205

Leu Gln Met Asn Ser Leu Arg Pro Glu Asp Thr Ala Val Tyr Tyr Cys
    210                 215                 220

Thr Ile Gly Gly Ser Leu Ser Arg Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Ser Val Gln Ala Gly Asp Ser Leu Arg Leu
            260                 265                 270

Ser Cys Ala Ala Ser Gly Arg Thr Leu Ser Asn Ser Ile Met Gly Trp
    275                 280                 285

Phe Arg Gln Ala Pro Gly Lys Glu Arg Glu Phe Val Ala Asn Ile Asn
    290                 295                 300

Trp Ser Gly Thr Ser Arg Leu Tyr Ala Asp Ser Val Lys Gly Arg Phe
305                 310                 315                 320

Thr Ile Ser Arg Asp Asn Thr Lys Ser Thr Val Tyr Leu Gln Met Asn
                325                 330                 335

Ser Leu Lys Pro Glu Asp Thr Ala Ile Tyr Tyr Cys Ala Ala Arg Ser
            340                 345                 350

Ser Thr Met Ser Ala Thr Asp Tyr Trp Gly Gln Gly Thr Gln Val Thr
            355                 360                 365

Val Ser Ser
    370

<210> SEQ ID NO 122
<211> LENGTH: 371
<212> TYPE: PRT
<213> ORGANISM: Artificial Sequence
<220> FEATURE:
<223> OTHER INFORMATION: Fusion protein

<400> SEQUENCE: 122

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Leu Ser Asn Ser
            20                  25                  30

Ile Met Gly Trp Phe Arg Gln Ala Pro Gly Lys Glu Arg Glu Phe Val
        35                  40                  45

Ala Asn Ile Asn Trp Ser Gly Thr Ser Arg Leu Tyr Ala Asp Ser Val
    50                  55                  60

Lys Gly Arg Phe Thr Ile Ser Arg Asp Asn Thr Lys Ser Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Ser Thr Met Ser Ala Thr Asp Tyr Trp Gly Gln Gly
            100                 105                 110

Thr Gln Val Thr Val Ser Ser Gly Gly Gly Gly Ser Gly Gly Gly Ser
        115                 120                 125

Glu Val Gln Leu Val Glu Ser Gly Gly Gly Ser Val Gln Ala Gly Asp
    130                 135                 140
```

```
Ser Leu Arg Leu Ser Cys Ala Ala Ser Gly Arg Thr Leu Ser Asn Ser
145                 150                 155                 160

Ile Met Gly Trp Phe Arg Gln Ala Pro Gly Lys Glu Arg Glu Phe Val
                165                 170                 175

Ala Asn Ile Asn Trp Ser Gly Thr Ser Arg Leu Tyr Ala Asp Ser Val
            180                 185                 190

Lys Gly Arg Phe Thr Ile Ser Arg Asp Asn Thr Lys Ser Thr Val Tyr
        195                 200                 205

Leu Gln Met Asn Ser Leu Lys Pro Glu Asp Thr Ala Ile Tyr Tyr Cys
    210                 215                 220

Ala Ala Arg Ser Ser Thr Met Ser Ala Thr Asp Tyr Trp Gly Gln Gly
225                 230                 235                 240

Thr Gln Val Thr Val Ser Ser Gly Gly Gly Ser Gly Gly Gly Ser
                245                 250                 255

Glu Val Gln Leu Val Glu Ser Gly Gly Gly Leu Val Gln Pro Gly Asn
                260                 265                 270

Ser Leu Arg Leu Ser Cys Ala Ala Ser Gly Phe Thr Phe Ser Ser Phe
            275                 280                 285

Gly Met Ser Trp Val Arg Gln Ala Pro Gly Lys Gly Leu Glu Trp Val
        290                 295                 300

Ser Ser Ile Ser Gly Ser Gly Ser Asp Thr Leu Tyr Ala Asp Ser Val
305                 310                 315                 320

Lys Gly Arg Phe Thr Ile Ser Arg Asp Asn Ala Lys Thr Thr Leu Tyr
                325                 330                 335

Leu Gln Met Asn Ser Leu Arg Pro Glu Asp Thr Ala Val Tyr Tyr Cys
            340                 345                 350

Thr Ile Gly Gly Ser Leu Ser Arg Ser Ser Gln Gly Thr Leu Val Thr
        355                 360                 365

Val Ser Ser
    370

<210> SEQ ID NO 123
<211> LENGTH: 115
<212> TYPE: PRT
<213> ORGANISM: Artificial Sequence
<220> FEATURE:
<223> OTHER INFORMATION: Nanobody binds Albumin

<400> SEQUENCE: 123

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
    115
```

<210> SEQ ID NO 124
<211> LENGTH: 116
<212> TYPE: PRT
<213> ORGANISM: Artificial Sequence
<220> FEATURE:
<223> OTHER INFORMATION: Nanobody binds Albumin

<400> SEQUENCE: 124

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 125
<211> LENGTH: 9
<212> TYPE: PRT
<213> ORGANISM: Artificial Sequence
<220> FEATURE:
<223> OTHER INFORMATION: Linker Sequence

<400> SEQUENCE: 125

Gly Gly Gly Gly Cys Gly Gly Gly Ser
1               5

<210> SEQ ID NO 126
<211> LENGTH: 40
<212> TYPE: PRT
<213> ORGANISM: Artificial Sequence
<220> FEATURE:
<223> OTHER INFORMATION: Linker Sequence

<400> SEQUENCE: 126

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 127
<211> LENGTH: 15
<212> TYPE: PRT
<213> ORGANISM: Artificial Sequence
<220> FEATURE:
<223> OTHER INFORMATION: Linker Sequence

<400> SEQUENCE: 127

Glu Pro Lys Ser Cys Asp Lys Thr His Thr Cys Pro Pro Cys Pro
1               5                   10                  15

<210> SEQ ID NO 128
<211> LENGTH: 24
<212> TYPE: PRT
<213> ORGANISM: Artificial Sequence
<220> FEATURE:
<223> OTHER INFORMATION: Linker Sequence

<400> SEQUENCE: 128

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 129
<211> LENGTH: 12
<212> TYPE: PRT
<213> ORGANISM: Artificial Sequence
<220> FEATURE:
<223> OTHER INFORMATION: Linker Sequence

<400> SEQUENCE: 129

Glu Pro Lys Thr Pro Lys Pro Gln Pro Ala Ala Ala
1               5                   10

<210> SEQ ID NO 130
<211> LENGTH: 62
<212> TYPE: PRT
<213> ORGANISM: Artificial Sequence
<220> FEATURE:
<223> OTHER INFORMATION: Linker Sequence

<400> SEQUENCE: 130

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60